US009855254B2

(12) United States Patent
Forbes et al.

(10) Patent No.: US 9,855,254 B2
(45) Date of Patent: *Jan. 2, 2018

(54) METHODS OF TREATING HEPATIC ENCEPHALOPATHY

(71) Applicant: Salix Pharmaceuticals, Ltd, Bridgewater, NJ (US)

(72) Inventors: William Forbes, Raleigh, NC (US); Kunal Merchant, Durham, NC (US); Enoch Bortey, Chapel Hill, NC (US); Audrey Shaw, Durham, NC (US)

(73) Assignee: Salix Pharmaceuticals, Ltd., Bridgewater, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/212,720

(22) Filed: Jul. 18, 2016

(65) Prior Publication Data

US 2017/0042864 A1 Feb. 16, 2017

Related U.S. Application Data

(63) Continuation of application No. 13/914,074, filed on Jun. 10, 2013, now Pat. No. 9,421,195, which is a continuation of application No. 12/964,847, filed on Dec. 10, 2010, now abandoned, which is a continuation of application No. 12/792,658, filed on Jun. 2, 2010, now abandoned, and a continuation-in-part of application No. 12/572,344, filed on Oct. 2, 2009, now abandoned.

(60) Provisional application No. 61/316,796, filed on Mar. 23, 2010, provisional application No. 61/307,417, filed on Feb. 23, 2010, provisional application No. 61/306,935, filed on Feb. 22, 2010, provisional application No. 61/305,854, filed on Feb. 18, 2010, provisional application No. 61/262,525, filed on Nov. 18, 2009, provisional application No. 61/102,349, filed on Oct. 2, 2008, provisional application No. 61/183,513, filed on Jun. 2, 2009.

(51) Int. Cl.
*A61K 31/40* (2006.01)
*A61K 31/437* (2006.01)
*A61K 31/7016* (2006.01)
*A61K 45/06* (2006.01)
*G06Q 50/22* (2012.01)

(52) U.S. Cl.
CPC ........ *A61K 31/437* (2013.01); *A61K 31/7016* (2013.01); *A61K 45/06* (2013.01); *G06Q 50/22* (2013.01)

(58) Field of Classification Search
None
See application file for complete search history.

(56) References Cited

U.S. PATENT DOCUMENTS

| 4,343,785 A | 8/1982 | Schmolka |
| 4,557,866 A | 12/1985 | Cannata et al. |
| 2002/0028764 A1 | 3/2002 | Grofte et al. |
| 2004/0106590 A1 | 6/2004 | Eisenstein |
| 2004/0229948 A1 | 11/2004 | Summar et al. |
| 2008/0119554 A1 | 5/2008 | Jalan et al. |
| 2008/0132530 A1 | 6/2008 | Viscomi et al. |
| 2008/0262012 A1 | 10/2008 | Viscomi et al. |
| 2009/0028940 A1 | 1/2009 | Jahagirdar et al. |
| 2009/0088423 A1 | 4/2009 | Sayada |
| 2009/0130201 A1 | 5/2009 | Viscomi et al. |
| 2009/0149453 A1 | 6/2009 | Sayada |
| 2010/0136125 A1 | 6/2010 | Jacobus et al. |
| 2010/0174064 A1 | 7/2010 | Gushurst et al. |
| 2010/0239664 A1 | 9/2010 | Gushurst et al. |

FOREIGN PATENT DOCUMENTS

| EP | 0 616 808 | * 9/1996 | ............ A61K 31/44 |
| EP | 2011486 A1 | 1/2009 | |
| WO | 03047577 A2 | 6/2003 | |
| WO | 2009108730 A2 | 9/2009 | |
| WO | 2009108814 A1 | 9/2009 | |
| WO | 2010040020 A1 | 4/2010 | |

OTHER PUBLICATIONS

Leevy et al (Dig Dis Sci 52:737-741, published Jan. 24, 2007).*
Vilstrup et al (HE in Chronic Liver Disease, 2014 Practice Guideline by AASLD and EASL, 2014).*
Lewis et al (Q J Med 96:623-633, 2003).*
Prescribing Information for Rifaximin, Spain, Date Unknown, but after Apr. 23, 1985.
Prescribing Information for Rifaximin, Tunesia, Mar. 2004.
Prescribing Information for Rifaximin, Turkey Sep. 2007.
Prescribing Information for Rifaximin, United States, Mar. 2010.
Prescribing Information for Rifaximin, Venezeula Sep. 2008.
Puxeddu et al., Rifaximin in the treatment of chronic hepatic encephalopathy, Current Medical Research and Opinion, vol. 13, No. 5, pp. 274-281,1995.
Rifaximin Demonstrates Highly Statistically Significant Results in Prevention of Hepatic Encephalopathy in Pivotal Phase 3 Study, published on Oct. 6, 2008 on website http://www.salix.com/news-media/news/previous-years-news/rifaximin-demonstrates-highly-statistically-significant-results-in-prevention-of-hepatic-encephalopathy-in-pivotal-phase-3-study.aspx.
Rifaximin Tablet Label, Jul. 2006.
Riggio et al (World J Gastrointest Pharmacol Ther 1:54-63, 2010).
Riggio, O. et al. (2005) J. Hepatol. 42:6740679.

(Continued)

*Primary Examiner* — Craig Ricci
(74) *Attorney, Agent, or Firm* — McCarter & English, LLP; Jonathan M. Sparks; Michael J. DeGrazia

(57) ABSTRACT

The application describes treatment of hepatic encephalopathy using gastrointestinal specific antibiotics. One example of a gastrointestinal specific antibiotic is rifaximin. The instant application also provides methods for determining if a subject has a neurological condition or hepatic encephalopathy by determining the critical flicker frequency and/or the venous ammonia level of the subject at two or more time points. The invention further provides methods for treating these subjects.

13 Claims, 34 Drawing Sheets

(56) References Cited

OTHER PUBLICATIONS

Romero-Gomez et al., Value of the critical flicker frequency in patients with minimal hepatic encephalopathy, Hepatology, Apr. 2007, 879-885.
Salix Pharmaceutical's Press Release (available online at www.redOorbit.com, Jan. 11, 2006).
Salix Pharmaceuticals Development Update; Xifaxan® Trials Initiated in C. Difficile-Associated Diarrhea, Irritable Bowel Syndrome and Hepatic Encephalopathy, posted on Jan. 11, 2006, Business Wire ("Xifaxan").
Sama, C. et al. (2004) Curr. Ther. Res. 5:413-422.
Scarpignato, C. and Pelosini, I. (2005) Chemotherapy 51(Supp):36-66.
Scarpignato, C. and Pelosini, I. (2006) Digestion 73:13-27 (EPUB: Feb. 8, 2006).
Sharma et al., Critical flicker frequency: Diagnostic tool for minimal hepatic encephalopathy, Journal of Hepatology 47 (2007) 67-63.
Tavares de Melo et al. (2008) Am. J. Health-Syst. Pharm. 65:818-822.
Williams, R. et al. (2000) Eur. J. Gastroenterol. Hepatol. 12:203-208.
Xifaxan Prescribing Information datasheet. Mar. 2008. retrieved from internet at <http://www.salix.com/assets/pdf/prescribe_info/xifaxanpi.pdf>. p. 1, col. 1, para 7.
Yoo et al (Am J Gastroenterol 98: 1395-1399, 2003—Abstract only).
Zeneroli, M. L. et al. (1997) Pharma. Res. 35:557-560.
Zeneroli, M. L. et al. (2005) Chemotherapy 51 (supp):90-95.
Zhao Liyun, "Clinical Study on New Medicine Rifaximin," Hainan Medical Journal, 2005, vol. 16, No. 5.
Adachi et al. Reviews of Anti-Infective Agents 42: 541-547 (2006).
Bass (2005) Hepatology AASLD Abstract No. 533.
Bass N. et al: "93 Rifaximin is Effective in Maintaining Remission in Hepatic Encephalopathy: Results of a Large, Randomized, Placebo-Controlled Trial", Journal of Hepatology, Munksgaard International Publishers, Copenhagen, DK, vol. 50, Apr. 1, 2009, p. S39.
Bass, et al., "Emerging Therapies for the Management of Hepatic Encephalopathy," Seminars in Liver Disease, Thieme Medical Publishers, US, vol. 27, No. Suppl. 2, Aug. 1, 2007, pp. 18-25.
Bass, N., et al,. "Rifaximin is Effective in Maintaining Remission in Hepatic Encephalopathy: Results of a Large, Randomized, Placebo-Controlled Trial," Journal of Hepatology, Apr. 2009, vol. 50, S39, Abstract 93.
Bass, NM (2006) Aliment Pharmacol. Ther 25(Suppl. 1):23-31.
Bustamante et al (J Hepatol 30:890-895, 1999).
Colecchia et al., "Efficacy of long term cyclic administration of the poorly absorbed antibiotic Rifaximin in symptomatic, uncomplicated colonic diverticular disease," World J Gastroenterol 13:264-269 (Jan. 2007).
De Marco et al. (1984) Curr. Ther. Res. 36:668674.
Di Piazza et al. (1991) 23:403-407.
Festi et al. (1993) Curr. Ther. Res. 54:598-609.
Festi, D. et al. (2006) Digestion 73(suppl 1):94-101.
Giacomo et al. (1993) Eur. J. Clin. Res. 4:57-66.
Gillis, J.C. and Brogden, R. N. (1995) Drugs 49:467-484.
Hiroshi Ishii and 3 others, D-009, "A Case of Refractory Hepatic Encephalopathy Successfully Treated with Vancomycin Hydrochloride," Proceedings of the Symposium of the Japanese Society of Social Insurance Medicine, Oct. 1999, 37th., p. 106.
Jane E. Henney, a report from the Commissioner of the United States Food and Drug Administration, Department of Health and Human Services, "Issues Related to Antimicrobial Resistance," Sep. 20, 2000.
Jiang et al. European Journal of Gastroenterology & Hepatology 20:1064-1070 (2008).
Jiang, et al., "Rifaximin: In vitro and in vivo Antibacterial Activity—A Review," Chemotherapy, 51(suppl 1):67-72, 2005.
Kirchels et al., "Critical flicker frequency for quantification of low grade hepatic encephalopathy," Hepatology 35 (2): 357-366 (Feb. 2002)—Abstract only.
Lawrence et al. (2008) Pharmacotherapy 28:1019-1032.
Leevy et al. Hospitalizations During the Use of Rifaximin Versus Lactulose for the Treatment of Hepatic Encephalopathy, Dig. Dis. Sci. (Jan. 24, 2007) 52:737-741.
Lewis & Howdle, "The neurology of liver failure," Q J Med 96:623-633 (2003).
Liu Houyu et al., "Hepatic encephalopathy (II)," Chinese Journal of Gastroenterology, 2003, vol. 8, No. 1.
Loguercio et al., Cyclic treatment of chronic hepatic encephalopathy with rifaximin. Results of a double-blind clinical study. Minerva Gastroenterol. Dietol., Mar. 2003; 49(1): 53-62 (Abstract only) ("Loguercio").
Maclayton, D. O. et al. (2009) Ann. Pharmacother. 43: 77-84) (EPUB:Dec. 17, 2008).
Mas et al., Comparison of rifaximin and lactitol in the treatment of acute hepatic encephalopathy: results of a randomized, double-blind, double-dummy, controlled clinical trial, Journal of Hepatology 38 (2003) 51-58.
Massa et al. (1993) Eur. J. Clin. Res. 4:7-18.
Miglio et al., Rifaximin, a non-absorbable rifamycin, for the treatment of hepatic encephalopathy. A double-blind, randomized trial, Curr Med Res Op 13:593-601, 1997 (Abstract Only).
NCT00298038, A Multi Center, Randomized, Double-Blind, Placebo-Controlled Trial to Evaluate the Efficacy, Safety and Tolerability of Rifaximin 550 Mg BID for 6 Months in Preventing Hepatic Encephalopathy, updated on Feb. 28, 2006.
Neff et al. (2006) Transplantation Proceedings 38:3552-3555.
Ojetti et al. (2009) Expert Opin. Drug Metab. Toxicol. 5: 675-682.
Paik et al. Comparison of rifaximin and lactulose for the treatment of hepatic encephalopathy: a prospective randomized study. Jun. 2005 Yonsei Medical Journal, vol. 46, N 3, p. 399-407; abstract; table 3-4, figure 1, p. 399, col. 2, para 2; p. 402; col. 1, para 1, col. 2, para 4; p. 403, col. 1, para 1.
Pedretti et al. (1991) Ital. J. Gastroenterol. 23:175-78.
Pharmacology/Toxicology Review of Rifaximin by the FDA, Apr. 26, 2004.
Prescribing Information for Rifaximin, Argentina, Date Unknown, but after Apr. 23, 1985.
Prescribing Information for Rifaximin, Austria Nov. 2005.
Prescribing Information for Rifaximin, Bulgaria, Jun. 2007.
Prescribing Information for Rifaximin, China, Oct. 2006.
Prescribing Information for Rifaximin, Czech Republic Mar. 2008.
Prescribing Information for Rifaximin, Greece 2001.
Prescribing Information for Rifaximin, Hungary Apr. 2004.
Prescribing Information for Rifaximin, Italy, Apr. 23, 1985.
Prescribing Information for Rifaximin, Korea, Jan. 2006.
Prescribing Information for Rifaximin, Lebanon, Dec. 2002.
Prescribing Information for Rifaximin, Mexico Jul. 2007.
Prescribing Information for Rifaximin, Poland Apr. 2006.
Prescribing Information for Rifaximin, Portugal Date Unknown, but after Apr. 23, 1985.
Prescribing Information for Rifaximin, Romania, Nov. 2005.
Prescribing Information for Rifaximin, Russia, Date Unknown, but after Apr. 23, 1985.
Prescribing Information for Rifaximin, Slovakia Sep. 2003.

* cited by examiner

Lactulose Daily Use

Kaplan Meier Estimates of Distribution of Time to Breakthrough HE

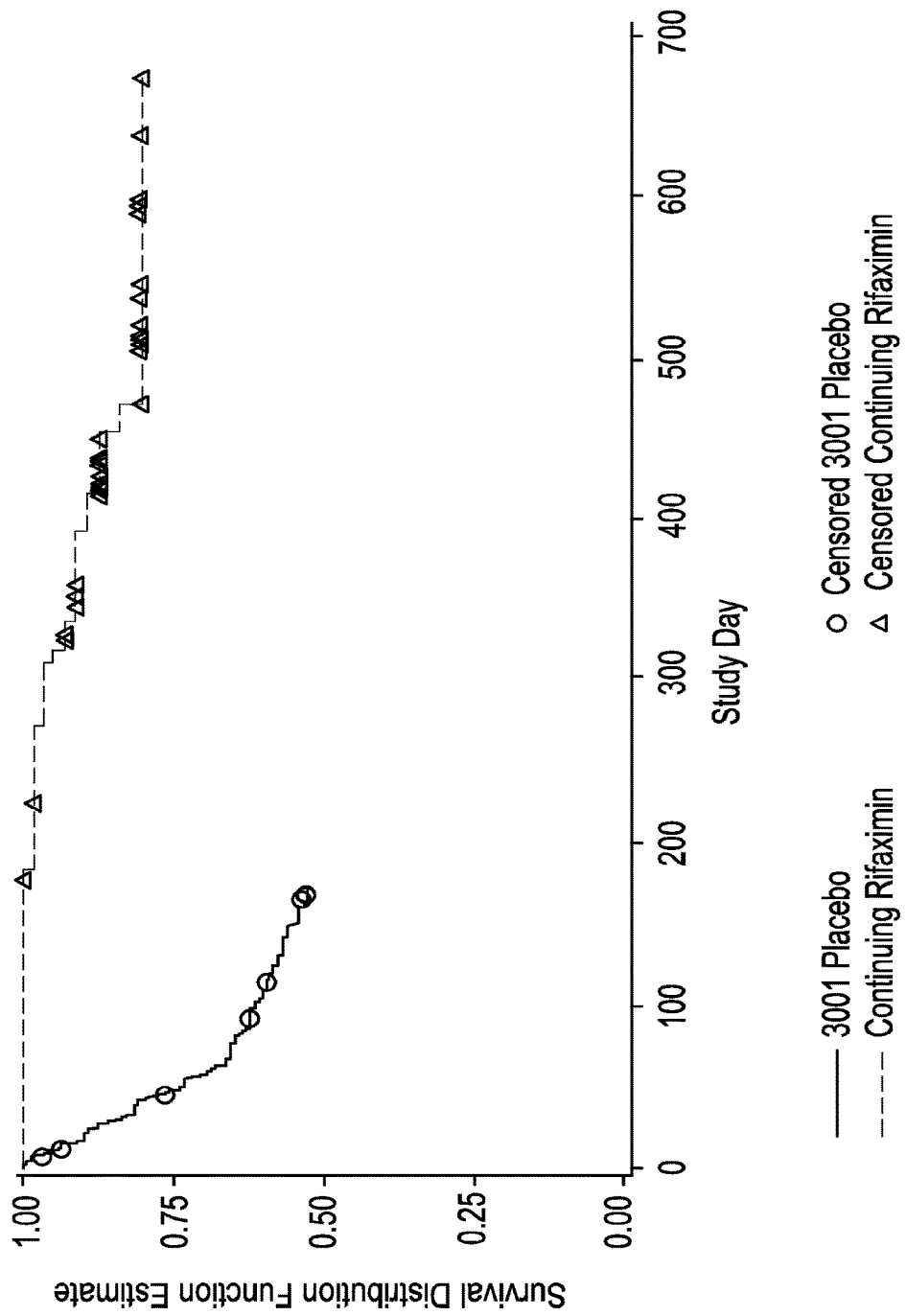

FIG. 16

| Type | HE Associated With | Category | Subcategory |
|---|---|---|---|
| Acute liver failure | Acute liver failure | | |
| Bypass | Portal-systemic Bypass and no intrinsic hepatocellular disease | Episodic<br><br>Persistent | Precipitated<br>Spontaneous<br>Recurrent } Overt<br><br>Mild |
| Cirrhosis | Cirrhosis and portal hypertension or portosystemic shunts | Minimal | Severe<br>Treatment-dependent |

FIG. 17

| | State of consciousness | Intellectual function | Personality/behavior | Neuromotor function |
|---|---|---|---|---|
| Conn = 0 | ○ Alert and oriented X3 | | | |
| Conn score = 1 | -Trivial lack of attention | -Shortened attn. span<br>-Impaired addition | -Euphoria or depression | -Asterixis |
| HESA criteria | ○ Sleep disorder | ○ Impaired complex computations<br>○ Shortened attention span | ○ Euphoria or depression | ○ Tremor<br>○ Impaired construction |
| Conn score = 2 | -Lethargy | -Minimal disorientation to time and place<br>-Impaired subtraction | -Bizarre behavior | -Asterixis |
| HESA criteria | ○ Lethargy | ○ Disorientation to time<br>○ Mental control = 1-4<br>○ Amnesia<br>○ Impaired simple computations | ○ Inappropriate behavior<br>○ Anxiety | ○ Slurred speech<br>○ Hyperactive reflexes |
| Conn score = 3 | -Somnolence / stupor | -Confusion gross disorientation | -Bizarre behavior | -Clonus/Rigidity |
| HESA criteria | ○ Somnolence | ○ Confusion<br>○ Disorientation to place<br>○ Mental control = 0 | ○ Bizarre behavior/anger rage | ○ Clonus/Rigidity |
| Conn score = 4 | -Coma | -N/A | -N/A | -N/A |
| HESA criteria | ○ No eyes opening, No verbal responses, No reaction to simple commands | | | |

Increase from 1993 to 2007

FIG. 22

| Midazolam Parameters | Midazolam Day 1 N = 24 | Day 9 7 days rifaximin N = 24 | Day 16 14 days rifaximin N = 20 |
|---|---|---|---|
| $C_{max}$(ng/mL) | 10.8 (3.56) | 10.1 (2.64) | 10.1 (3.10) |
| $AUC_{0-t}$ (ng·h/mL) | 22.5 (9.19) | 21.0 (7.54) | 20.5 (8.40) |

FIG. 29

Lactulose Use - Did Not Influence
Study Outcome
Study 3001

| Parameter | Placebo<br>N = 159 | Rifaximin<br>N = 140 |
|---|---|---|
| Lactulose at baseline | | |
| Yes, n (%) | 145 (91) | 128 (91) |
| No, n (%) | 14 (9) | 12 (9) |
| Average daily lactulose use<br>(cups/d [15mL/cup]) | | |
| Mean ± SD | 3.51 ± 2.59 | 3.14 ± 2.10 |
| Median (min - max) | 2.8 (0 - 11.8) | 2.8 (0 - 9.0) |

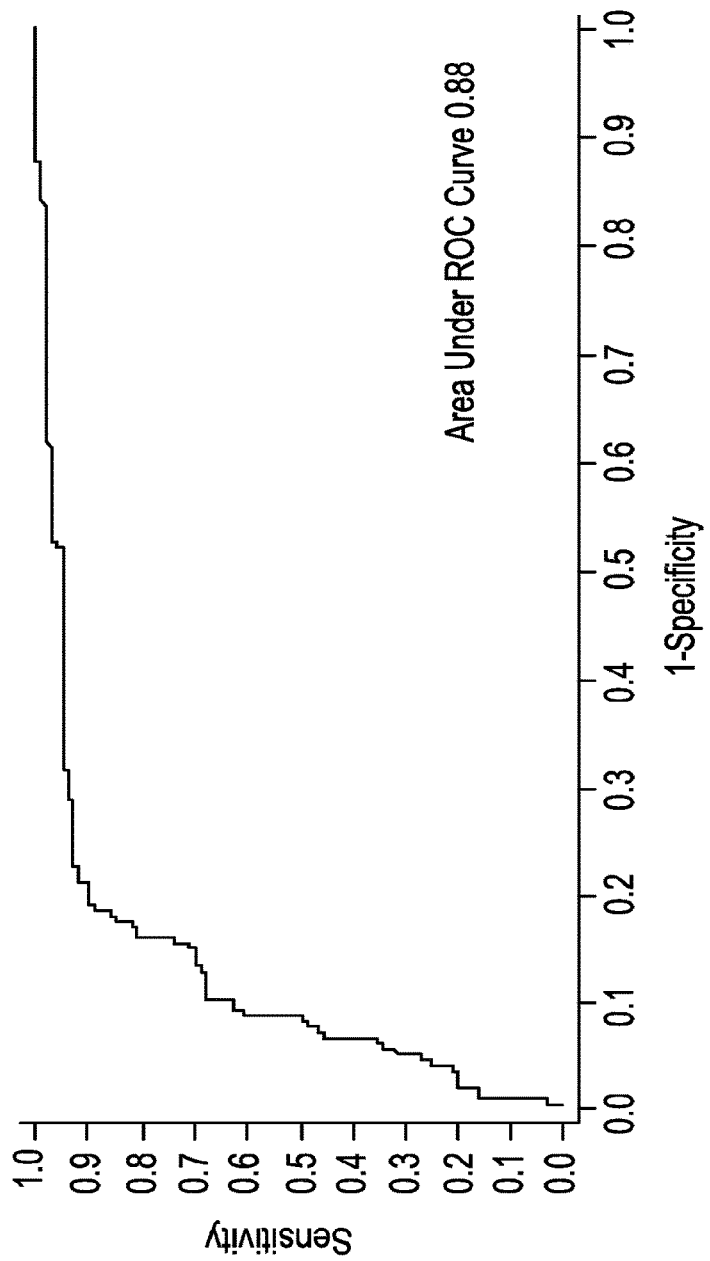

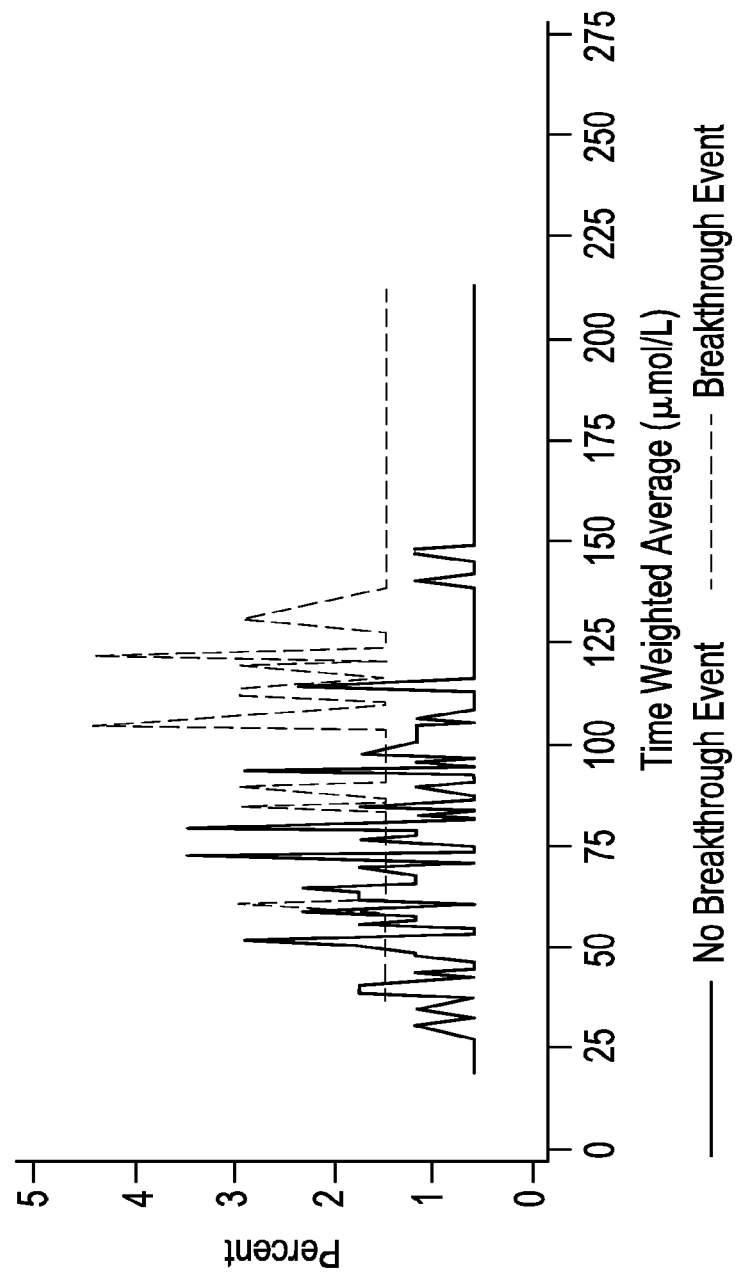

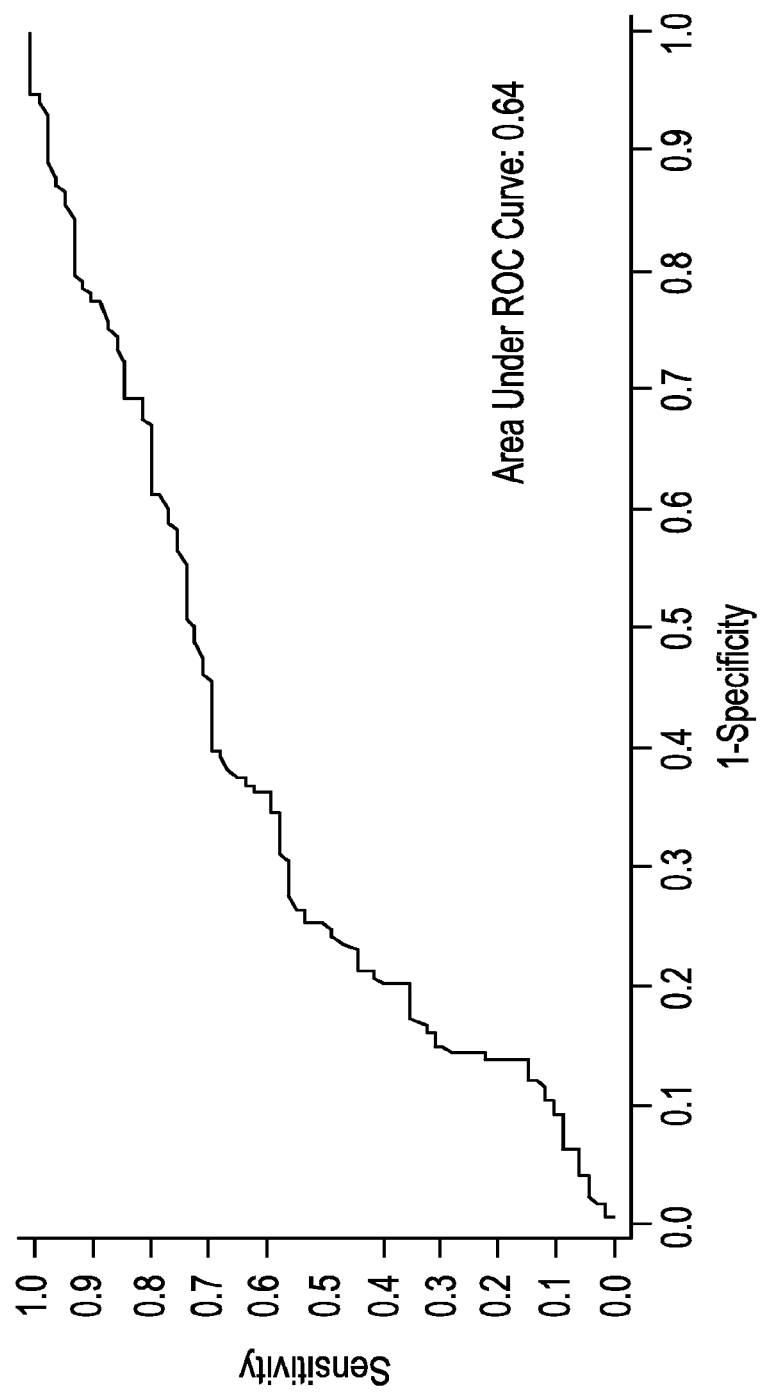

METHODS OF TREATING HEPATIC ENCEPHALOPATHY

RELATED APPLICATIONS

This application is a continuation of Ser. No. 12/964,847 filed Dec. 10, 2010, which is a continuation of Ser. No. 12/792,658, filed Jun. 2, 2010, which is a continuation-in-part of U.S. application Ser. No. 12/572,344, filed Oct. 2, 2009 which claims the benefit of U.S. Provisional Application Ser. No. 61/102,349, filed Oct. 2, 2008. U.S. application Ser. No. 12/792,658 also claims the benefit of U.S. Provisional Application No. 61/183,513 filed Jun. 2, 2009; U.S. Provisional Application No. 61/262,525, filed Nov. 18, 2009; U.S. Provisional Application No. 61/305,854, filed Feb. 18, 2010; U.S. Provisional Application No. 61/306,935, filed Feb. 22, 2010; U.S. Provisional Application No. 61/307,417, filed Feb. 23, 2010; and U.S. Provisional Application No. 61/316,796, filed Mar. 23, 2010. The entire contents of each of the aforementioned applications is hereby expressly incorporated herein by reference.

BACKGROUND

Hepatic encephalopathy (HE) is caused by a reversible decrease in neurologic function associated with liver failure and portosystemic venous shunting. HE occurs in 1 of every 3 cases of cirrhosis, in cases of fulminant hepatic failure reported in the United States (US), and is present in nearly half of patients reaching end-stage liver disease. It may occur at any age, but the peaks parallel those of fulminant liver disease (peak=40's), and cirrhosis (peak=late 50's).

The incidence of HE is likely to increase with the incidence of hepatitis C in the general population and cirrhotics in aging patients. Acute HE signifies a serious prognosis with a 40% likelihood of survival for 1 year. There is a need in the art for a compositions and methods for treating and preventing HE.

Moreover, methods of predicting a breakthrough HE event or for determining when to prophylactically treat a subject prior to the occurrence of a breakthrough event are necessary in the art.

SUMMARY

Provided herein are compositions and methods for the prevention and treatment of hepatic encephalopathy.

One embodiment is a method of treating or preventing hepatic encephalopathy (HE) in a subject comprising administering to a subject a gastrointestinal (GI) specific antibiotic. In one embodiment the GI specific antibiotic is rifaximin. In another embodiment, the rifaximin is 1100 mg/day of rifaximin.

Another embodiment is a method of decreasing a subject's risk of a hepatic encephalopathy HE breakthrough episode by administering a GI specific antibiotic to a subject suffering from HE.

Yet another embodiment is a method of maintaining remission of hepatic encephalopathy in a subject by administering a GI specific antibiotic to a subject suffering from HE.

Still another embodiment is a method of reducing the frequency of hospitalization visits by an HE patient, comprising administering a GI specific antibiotic to a subject suffering from HE.

In one embodiment, the GI specific antibiotic is administered to the subject with lactulose, prior to treatment with lactulose, or following treatment with lactulose. In one embodiment the subject or a health care worker is advised to administer the GI specific antibiotic with lactulose.

In one embodiment the subject or a health care worker is advised by a pharmaceutical label or insert to administer the GI specific antibiotic with lactulose in order to maintain remission of HE, or to decrease the risk for episodes of overt HE.

In one embodiment, the subject or health care worker is advised to administer two 550 mg tablets of rifaximin twice daily with lactulose. Lactulose use may be titrated over time so that the subject maintains 2-3 soft stool bowel movements per day. In one embodiment the lactulose is administered in 15 nil dosages, wherein each 15 ml dosage contains 10 mg of lactulose.

In one embodiment, subjects in need of treatment for HE and having a Child-Pugh grade of A or B are treated with a GI specific antibiotic.

In another embodiment, subjects in need of treatment for HE having a Child-Pugh grade of A or B are treated with a GI specific antibiotic in combination with lactulose.

In another embodiment, subjects having a Child-Pugh grade of A or B, or their health care worker, are advised that they should be treated with a GI specific antibiotic. The advice can be oral or written advice, such as on a pharmaceutical label or package insert.

In another embodiment, subjects having a Child-Pugh grade of A or B, or their health care worker, are advised that they should be treated with a GI specific antibiotic in combination with lactulose.

In one embodiment, a subject in need of treatment for HE and having a Child-Pugh grade of less than C is treated with a GI specific antibiotic. In one embodiment, a subject in need of treatment for HE and having a Child-Pugh grade of less than C is treated with a GI specific antibiotic and lactulose.

In another embodiment, a subject in need of treatment for HE, or their health care worker is advised of the risk for anaphylaxis prior to treatment with a GI specific antibiotic.

In one embodiment, subjects in need of treatment for HE and having a MELD score of 25 or less are treated with a GI specific antibiotic.

In another embodiment, subjects in need of treatment for HE having a MELD score of 25 or less are treated with a GI specific antibiotic in combination with lactulose.

In another embodiment, subjects having a MELD score of 25 or less are advised that they should be treated with a GI specific antibiotic. The advice can be oral or written advise, such as on a pharmaceutical label or package insert.

In another embodiment, subjects having a MELD score of 25 or less are advised that they should be treated with a GI specific antibiotic in combination with lactulose.

The novel methods and devices presented herein are based in part on the finding of a correlation between CFF and/or venous ammonia concentration and the occurrence of breakthrough HE events. Moreover, the novel methods and devices are also based on the discovery that the time weighted average CFF and/or venous ammonia concentration is an accurate predictor of breakthrough HE events and prognosis of subjects with HE.

Accordingly, in one aspect provided herein are methods of diagnosing hepatic encephalopathy (HE) in a subject by determining the critical flicker frequency (CFF) of a subject at two or more time points, wherein a decrease in the CFF is indicative that the subject has hepatic encephalopathy. In a related embodiment, the CFF comprises the CFF time weighted average. In another related embodiment, the CFF time weighted average comprises less than about 24 Hz.

In another aspect, provided herein are methods of determining a subject's risk of an HE breakthrough event, by determining the critical flicker frequency (CFF) of a subject at two or more time points, wherein a decrease in the CFF is indicative that the subject has an increased risk of a HE breakthrough event. In a related embodiment, the CFF comprises the CFF time weighted average. In another related embodiment, the CFF time weighted average comprises less than about 24 Hz. In another embodiment, a CFF time weighted average of 10 Hz is indicative that the subject has the greatest chance of a HE breakthrough event.

In another aspect, provided herein are methods of determining the prognosis of a subject having HE, by determining the critical flicker frequency (CFF) of a subject at two or more time points, wherein a decrease in the CFF is indicative that the subject has a poor prognosis. In a related embodiment, the CFF comprises the CFF time weighted average. In another related embodiment, the CFF time weighted average comprises less than about 24 Hz, or less than about 20 Hz.

In another aspect, provided herein are methods of treating or preventing an HE event, by determining the critical flicker frequency (CFF) of a subject at two or more time points, administering to a subject having a decrease in the CFF average between the time points an effective amount of a GI specific antibiotic, (e.g., rifaximin), thereby treating or preventing an HE event. In another embodiment, the subject is administered a GI specific antibiotic when the CFF time weighted average is less than 20 Hz.

In one embodiment, the subject is also administered lactulose. In another embodiment, the risk is increased as compared to a control subject without HE.

In related embodiments, the two or more time points occur within one week, four weeks, six months, or more.

In another aspect provided herein are methods of diagnosing hepatic encephalopathy (HE) in a subject by determining the venous ammonia levels of a subject at two or more time points, wherein an increase in the venous ammonia levels is indicative that the subject has hepatic encephalopathy.

In one embodiment, the venous ammonia level comprises the time weighted average venous ammonia levels. In another embodiment, the time weighted average venous ammonia level comprises more than about 100 µmol/L.

In another aspect, provided herein are methods of determining a subject's risk of an HE breakthrough event, by determining the venous ammonia levels of a subject at two or more time points, wherein an increase in the venous ammonia levels is indicative that the subject has an increased risk of a HE breakthrough event.

In one embodiment, the venous ammonia level comprises the time weighted average venous ammonia levels. In another embodiment, the time weighted average venous ammonia level comprises more than about 100 µmol/L.

In another aspect, provided herein are methods of determining the prognosis of a subject having HE, by determining the venous ammonia level of a subject at two or more time points, wherein an increase in the venous ammonia level is indicative that the subject has a poor prognosis.

In one embodiment, the venous ammonia level comprises the time weighted average venous ammonia levels. In another embodiment, the time weighted average venous ammonia level comprises more than about 100 µmol/L, or more than about 110 µmol/L.

In another aspect, provided herein are methods of treating or preventing an HE event, by determining the venous ammonia level of a subject at two or more time points, administering to a subject having an increase in the venous ammonia level between the time points an effective amount of Rifaximin, thereby treating or preventing an HE event.

In one embodiment, the venous ammonia level comprises the time weighted average venous ammonia levels. In another embodiment, the time weighted average venous ammonia level comprises more than about 100 µmol/L.

In another embodiment, the methods further comprise administering lactulose.

In related embodiments, the two or more time points occur within one week, two weeks, three weeks, four weeks, five weeks, six weeks, eight weeks, six months, or more. Also included are time points at any time in between the points.

In another aspect, provided herein are methods of treating a subject having HE comprising administering to the subject an effective amount of a GI specific antibiotic, e.g., rifaximin, thereby treating the subject.

In related embodiments, the GI specific antibiotic, e.g., rifaximin, is administered for greater than 365 days, greater than 730 days, greater than 1095 days, or for the remainder of the life of the subject.

In another aspect provided herein are methods of diagnosing a neurological disease in a subject, by determining the critical flicker frequency (CFF) of a subject at two or more time points, wherein a decrease in the CFF is indicative that the subject has a neurological disease. The decrease may be between any two time points. For example, between the first and second time points, between the first and third time points, between the first and fourth time points, between the second and third time points, between the second and fourth time points and the like.

In a related embodiment, the CFF comprises the CFF time weighted average. In another embodiment, the neurological disease or disorder comprises Alzheimer's disease or Parkinson's disease. Also included are diseases in which the CFF is modulated in a subject. Modulated, as used herein includes increases or decreasing from a baseline or a change from any measurement, even if not baseline for the subject. The baseline for a subject may be determined when a subject not experiencing an HE event or other neurological event, when a subject has recovered or is in remission from an HE event or other neurological event.

In another aspect, provided herein are methods of determining the prognosis of a subject having a neurological disease, by determining the critical flicker frequency (CFF) of a subject at two or more time points, wherein a decrease in the CFF is indicative that the subject has a poor prognosis. Poor prognosis, as used herein, includes a prognosis that life expectancy is less than prior prognosis.

In a related embodiment, the CFF comprises the CFF time weighted average. In another embodiment, the neurological disease or disorder comprises Alzheimer's disease, Parkinson's disease, trauma, migraine, chronic headache, insomnia and other sleep disorders, and/or epilepsy.

In related embodiments, the two or more time points occur within one week, four weeks, six months, or more.

In another aspect, provided herein are computerized methods for identifying subjects having a neurological disease by maintaining a database of CFFs for subjects at various time points and stages of disease progression, comparing the results of an individuals CFF results taken at two or more time points to the database, obtaining the diagnosis of a neurological disease from the computer if subject has CFF results that decrease between measurements.

In one embodiment, the CFF comprises the CFF time weighted average. In another embodiment the CFF time weighted average or a second or subsequent time point comprises less than about 24 Hz. In another embodiment, the methods further comprise controlling a printing device to print a report based on the results of the method.

In another aspect, provided herein are business methods for decreasing healthcare costs, comprising determining the critical flicker frequency (CFF) of a subject at two or more time points, storing patient information on a computer processor, determining if the subject has a neurological disease by determining if the CFF value has decreased between time points, and treating the subject as necessary to avoid or delay hospitalization.

In another aspect, provided herein are business methods for decreasing healthcare costs comprising determining the critical flicker frequency (CFF) of a subject at two or more time points, storing patient information on a computer processor, determining if the subject has hepatic encephalopathy by determining if the CFF value has decreased between time points, treating the subject as necessary to avoid or delay hospitalization.

A device for determining the risk of an HE event, comprising, a "flicker box," a measurement device to CFF, and a computer with an algorithm. In another embodiment, the method further comprises a memory device capable of storing CFF data.

BRIEF DESCRIPTION OF THE DRAWINGS

FIG. 13 depicts the Kaplan Meier estimates of distribution of time to first breakthrough HE for continuing rifaximin subjects who did not have an HE episode in the first study vs placebo.

FIG. 16 shows the clinical presentation of HE. The classification was by the 1998 WCOG Working Group. Adapted from Ferenci P, et al. *Hepatology.* 2002; 35:716-721.

FIG. 17 shows the HESA adaptation of Conn Score.

FIG. 22 shows drug interactions with midazolam and rifaximin. No significant inhibition of CYP enzymes, P-glycoprotein, or BSEP. Portosystemic shunting in liver impairment may reduce liver exposure.

FIG. 29 is a bar chart illustrating that lactulose use between a control group and a group taking rifaximin was the same.

FIG. 32 depicts receiver operating characteristic curve for CFF results in the prediction of breakthrough overt HE.

FIG. 33 depicts the distribution of time-weighted average venous ammonia concentrations results by breakthrough overt HE status.

FIG. 34 depicts receiver operating characteristic curve for venous ammonia levels in the prediction of breakthrough overt HE.

DETAILED DESCRIPTION

Figure 1:
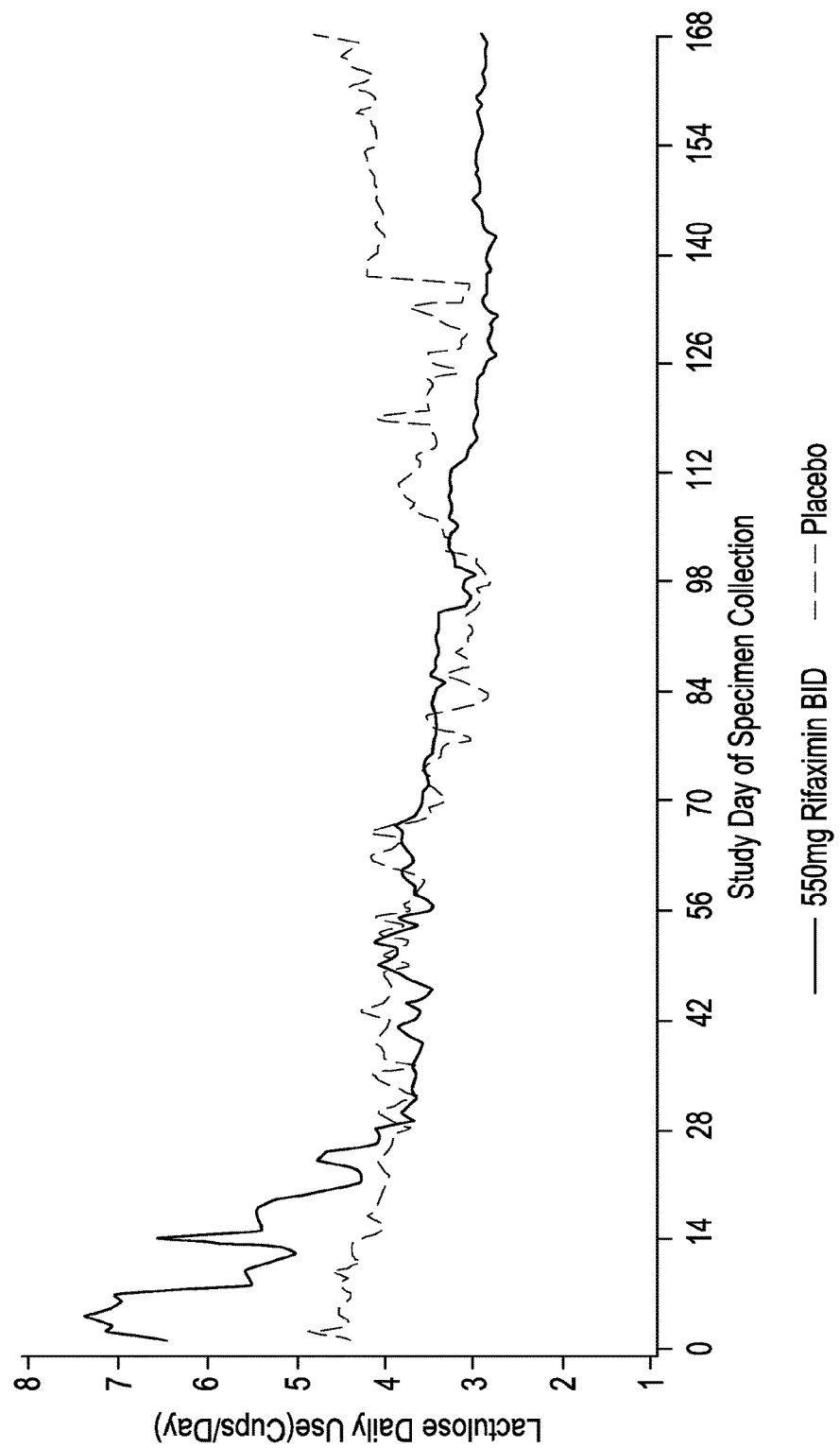
FIG. 1 is a line graph comparing lactulose daily use between subjects taking placebos and subjects taking rifaximin.

Hepatic encephalopathy, also known as hepatic coma or portal-systemic encephalopathy (PSE), is a serious, rare, complex, episodic, neuropsychiatric syndrome associated with advanced liver disease. Hepatic encephalopathy is a formidable burden on the patient, his/her family, and the healthcare system; and the current standard of care is inadequate. Overt, episodic HE is common among patients with liver cirrhosis. The condition is rare among individuals in the overall, general population. Overt HE episodes are debilitating, can present without warning, render the patient incapable of self-care, and frequently result in hospitalization. The frequency of hospitalizations due to HE increased since 1993 to over 40,000 patients in 2003; and in 2004, 50,962 patients were hospitalized with a principal diagnosis of HE.

The main pathogenesis of HE is related to nitrogenous substances derived from the gut adversely affecting brain function. The most influential of these compounds is thought to be ammonia, a byproduct of protein digestion that is normally detoxified by the liver. Correlation of blood levels with mental state in cirrhosis, however, is inaccurate, in part, because the blood-brain barrier permeability to ammonia is increased in patients with HE. Other gut-derived toxins have also been proposed as being responsible for HE.

In patients with chronic liver disease, the occurrence of hepatic encephalopathy is associated with a low quality of life compared to age-matched patients without HE. Overt HE episodes are debilitating, can present without warning, render the patient incapable of self-care, and frequently result in hospitalization. Patients with HE experience symptoms including fatigue, daytime sleepiness, and lack of awareness (Conn score 1); and confusion and disorientation (Conn score 2) that significantly interfere with day-to-day function and decreased ability for self care. Often, this lack of self care leads to improper nutrition and non-adherence to therapy and further escalates into more severe symptoms such as increased somnolence, gross disorientation and stupor (Conn score 3) or coma (Conn score 4).

A history of overt HE episodes and the severity of HE episodes were also found to be predictive of decreased survival in patients with chronic liver disease. In patients with liver cirrhosis and a history of overt HE episodes, survival probability was 42% at 1 year and 23% at 3 years after experiencing an HE episode. In another analysis, the occurrence of an HE episode of Conn score 2 in patients with cirrhosis was associated with a 4-fold increase in the risk of death.

The inventors of the instant application have determined that there is a correlation between CFF and venous ammonia concentration and the occurrence of breakthrough HE events. Moreover, the inventors have determined that time weighted average CFF or venous ammonia concentration is an accurate predictor of breakthrough HE events and prognosis of subjects with HE. In another embodiment, the inventors have determined that subjects who continue taking Rifaximin for a long duration of time, e.g., greater than 1.5 years, continue to see beneficial results, e.g., decreased incidence of breakthrough HE events.

In certain embodiments, provided herein are methods for determining if a subject has a neurological disease or HE. The methods of the invention rely on determining the critical flicker frequency or the venous ammonia level.

Critical flicker frequency, also called CFF, can be determined, for example, by standard methods known in the art. Moreover, commercial instruments are available to measure CFF, which are known by those skilled in the art.

Critical flicker frequency tests utilize, for example, the correlation between cerebral processing of oscillatory visual stimuli and CNS impairment due to increased HE severity. This test identifies a frequency at which a flickering light is perceived by a subject as a steady light. A decline in this frequency has been associated with increasing severity of HE. In one example, circular light pulses with a 1:1 ratio between the visual impulse and the interval were used with decreasing frequency in gradual steps of 0.5 to 0.1 Hz/second. The frequency of the white light, which is initially generated as a high-frequency pulse (50 Hz) and which gives the patient the impression of a steady light, can be reduced gradually until the subject had the impression that the steady light had changed to a flicker. The subject registered this change by pressing a hand-held switch. The flicker frequencies can be measured multiple times and the mean values for each subject can be calculated.

In some embodiments, CFF values are tracked over time for each subject. From these values the area under the CFF versus time curve (AUC) could be calculated using calculations that are standard in the art. For example, AUC can be calculated using the trapezoidal rule. To use the trapezoidal rule, data points are connected by straight line segments, perpendiculars are erected from the abscissa to each data point, and the sum of the areas of the triangles and trapezoids so constructed is computed and equals the AUC.

To accurately describe the variation in the CFF over time for each subject the time-weighted average (twa) can be computed. To calculated the twa, the results of the CFF test over time or the venous ammonia levels are expressed as:

$$twa = \frac{AUC}{T},$$

where T is the exposure time. Thus, twa describes the average CFF and/or venous ammonia level effect between multiple time points.

The correlation between twa and the presence or absence of breakthrough HE episode can be analyzed with analysis of variance and Spearman rank correlation coefficient. Additionally, a ROC curve analysis can be performed to evaluate the accuracy of the twa to discriminate between the presence or absence of breakthrough episodes. A ROC analysis for the data collected in the Examples demonstrated that the methodology is a highly accurate predictor of HE.

These toxic compounds gain access to the systemic circulation as a result of decreased hepatic function or portal-systemic shunts. Once in brain tissue, the compounds produce alterations of neurotransmission that affect consciousness and behavior. HE is attributed to global central nervous system depression from nitrogenous compounds that result in excitation of gamma-aminobutyric acid (GABA) and decreased neurotransmission of glutamate.

Precipitating factors include azotemia (29%), sedatives, tranquilizers, analgesics (24%), gastrointestinal bleeding (18%), excess dietary protein (9%), metabolic alkalosis (11%), infection (3%), constipation (3%). Surgery, particularly transjugular intrahepatic portal-systemic shunt (TIPS) procedures, also may precipitate HE. HE due to unknown causes accounts for only 2% of cases.

Initial manifestations are subclinical and require psychometric testing for diagnosis. There are 4 progressive stages of impairment known as the West Haven criteria (or Conn score) which range from Stage 0 (Lack of detectable changes in personality) to Stage 4 (Coma, decerebrate posturing, dilated pupils) as discussed in more detail below.

HE is manifested as a continuum of psychomotor dysfunction, impaired memory, increased reaction time, sensory abnormalities, poor concentration and in severe forms, as coma. Changes may be observed in personality, consciousness, behavior and neuromuscular function. Neurologic signs may include hyperreflexia, rigidity, myoclonus and asterixis (coarse "flapping" muscle tremor). Cognitive tasks such as connecting numbers with lines can be abnormal. Fetor hepaticus (sweet breath odor) may be present. Electroencephalogram (EEG) tracings show nonspecific slow, triphasic wave activity mainly over the frontal areas. Prothrombin time may be prolonged and not correctable with Vitamin K. A computed tomography scan of the head may be normal or show general atrophy. Finally, signs of liver disease such as jaundice and ascites may be noted.

Diagnosis of HE is made on the basis of medical history, and physical and mental status examinations with the required clinical elements being knowledge of existent liver disease, precipitating factor(s), and/or prior history of HE. An EEG may show slow-wave activity, even in mild cases. An elevated serum ammonia level is characteristic but not essential, and correlates poorly with the level of encephalopathy Management of patients with chronic HE includes 1) provision of supportive care, 2) identification and removal of precipitating factors, 3) reduction of nitrogenous load from the gut, and 4) assessment of the need for long term therapy. The nitrogenous load from the gut is typically reduced using non-absorbable disaccharide (lactulose) and/or antibiotics.

Lactulose is considered a first-line treatment in the United States. Lactulose is metabolized by the intestinal bacteria of the colon, which leads to reduced fecal pH, then to a laxative effect, and finally to fecal elimination. The reduced fecal pH ionizes ammonia ($NH_3$) to the ammonium ion ($NH_4^+$) which is used by the bacteria for amino acid and protein synthesis. This lowers the serum ammonia levels and improves mental function.

Conventional therapy aims to lower the production and absorption of ammonia. Lactulose is typically used in doses of 30-60 g daily. However, the dose can be titrated up to 20-40 g TID-QID to affect 2-3 semi-formed bowel movements per day. If lactulose cannot be administered orally or per nasogastric tube, for example to patients with stage 3 and 4 HE, it may be given as a 300 cc (200 g) retention enema.

For acute encephalopathy, lactulose can be administered either orally, by mouth or through a nasogastric tube, or via retention enemas. The usual oral dose is 30 g followed by dosing every 1 to 2 hours until evacuation occurs. At that point, dosing is adjusted to attain two or three soft bowel movements daily.

Lactulose for is readily available over-the-counter. A convenient and relatively tasteless formulation, often referred to in the trade as "lactulose powder for oral solution" can be obtained, for example, from Bertek Pharmaceuticals, Sugarland, Tex. as Kristalose® in 10 and 20 gm packets. The lactulose syrups commonly sold as laxatives include Cephulac®, Chronulac®, Cholac®, and Enulose®. These syrups can be substituted for lactulose powder by using sufficient syrup to provide the desired dosage of lactulose; typically, the named syrups contain about 10 gm lactulose in 15 ml of syrup.

Broad-spectrum, GI-active antibiotics including neomycin, metronidazole, vancomycin and paromomycin have been used with or without lactulose. Current guidelines recommend neomycin at 1 to 2 g/day by mouth with periodic renal and annual auditory monitoring or metronidazole at 250. Lactulose can induce diarrhea leading to dehydration, a precipitating factor of HE. Additionally, compliance with lactulose is limited by patient dislike of its overly sweet taste. In addition, a dosing schedule that is linked to bowel habits and side effects of flatulence, bloating, diarrhea (which leads to dehydration), and acidosis make lactulose difficult to use long-term.

Antibiotic use in treatment of HE is hampered by toxicity associated with long-term use. Specifically, systemic absorption of neomycin, metronidazole and ampicillin has led to rare cases of nephrotoxicity, ototoxicity, *S. enterocolitis*, and/or development of resistant bacterial strains. Additionally, neomycin inhibits only aerobic bacteria. Metronidazole is metabolized slowly in patients with hepatic dysfunction, has a potential for alcohol interactions (disulfiram-like effect), and high blood levels may result in seizures.

One gastrointestinal specific antibiotic is rifaximin. Rifaximin is a nonaminoglycoside, semisynthetic antibiotic derived from rifamycin 0. It is a nonsystemic, non-absorbed, broad-spectrum, oral antibiotic specific for enteric pathogens of the GI tract. Rifaximin was found to be advantageous in treatment of HE relative to previously used antibiotics; e.g., negligible systemic absorption (<0.4%) regardless of food intake or presence of GI disease and exhibits no plasma accumulation with high or repeat doses. The lack of systemic absorption makes rifaximin safe and well tolerated, thus improving patient compliance and reducing side effects associated with currently known treatments.

Rifaximin (INN; see The Merck Index, XIII Ed., 8304) is an antibiotic belonging to the rifamycin class of antibiotics, e.g., a pyrido-imidazo rifamycin. Rifaximin exerts its broad antibacterial activity, for example, in the gastrointestinal tract against localized gastrointestinal bacteria that cause infectious diarrhea, irritable bowel syndrome, small intestinal bacterial overgrowth, Crohn's disease, and/or pancreatic insufficiency. It has been reported that rifaximin is characterized by a negligible systemic absorption, due to its chemical and physical characteristics (Descombe J. J. et al. Pharmacokinetic study of rifaximin after oral administration in healthy volunteers. Int J Clin Pharmacol Res, 14 (2), 51-56, (1994)).

Rifaximin is described in Italian Patent IT 1154655 and EP 0161534. EP patent 0161534 discloses a process for rifaximin production using rifamycin 0 as the starting material (The Merck Index, XIII Ed., 8301). U.S. Pat. No. 7,045,620 B1 discloses polymorphic forms of rifaximin. The applications and patents referred to here are incorporated herein by reference in their entirety for all purposes A rifamycin class antibiotic is, for example, a compound having the structure of Formula I:

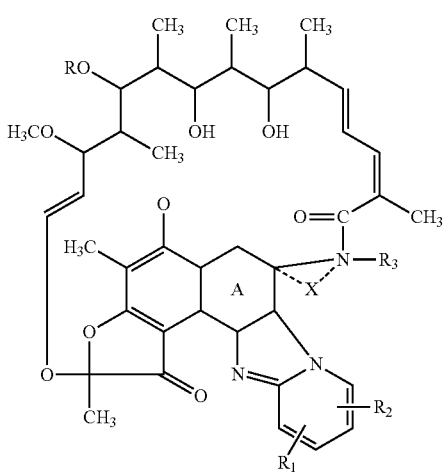

wherein A may be the structure $A_1$:

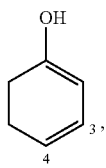

or the structure $A_2$

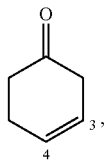

wherein, -x- is a covalent chemical bond or nil; R is hydrogen or acetyl;

$R_1$ and $R_2$ independently represent hydrogen, $(C_{1-4})$ alkyl, benzyloxy, mono- and di-$(C_{1-3})$ alkylamino-$(C_{1-4})$ alkyl, $(C_{1-3})$alkoxy-$(C_{1-4})$alkyl, hydroxymethyl, hydroxy-$(C_{2-4})$-alkyl, nitro or $R_1$ and $R_2$ taken together with two consecutive carbon atoms of the pyridine nucleus form a benzene ring unsubstituted or substituted by one or two methyl or ethyl groups; $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Also described herein is a compound as defined above, wherein A is $A_1$ or $A_2$ as above indicated, -x- is a covalent chemical bond or nil, R is hydrogen or acetyl, $R_1$ and $R_2$ independently represent hydrogen, $(C_{1-4})$alkyl, benzyloxy, hydroxy-$(C_{2-4})$ alkyl, di-$(C_{1-3})$ alkylamino-$(C_{1-4})$ alkyl, nitro or $R_1$ and $R_2$ taken together with two consecutive carbon atoms of the pyridine nucleus form a benzene ring and $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Also described herein is a compound as defined above, wherein A is $A_1$ or $A_2$ as above indicated, -x- is a covalent chemical bond or nil, R is acetyl, $R_1$ and $R_2$ independently represent hydrogen, $(C_{1-4})$ alkyl or $R_1$ and $R_2$ taken together with two consecutive carbon atoms of the pyridine nucleus form a benzene ring and $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Also described herein is a compound as defined above, which is 4-deoxy-4'-methyl-pyrido[1',2'-1,2]imidazo [5,4-c]rifamycin SV. Also described herein is a compound as defined above, which is 4-deoxy-pyrido [1',2': 1,2]imidazo [5,4-c]rifamycin SV.

Also described herein is a compound as defined above, wherein A is as described above, -x- is a covalent chemical bond or nil; R is hydrogen or acetyl; $R_1$ and $R_2$ independently represent hydrogen, $(C_{1-4})$ alkyl, benzyloxy, mono- and di-$(C_{1-3})$alkylamino$(C_{1-4})$alkyl, $(C_{1-3})$alkoxy-$(C_{1-4})$ alkyl, hydroxymethyl, hydroxy-$(C_{2-4})$-alkyl, nitro or $R_1$ and $R_2$ taken together with two consecutive carbon atoms of the pyridine nucleus form a benzene ring unsubstituted or substituted by one or two methyl or ethyl groups; $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Rifaximin is a compound having the structure of formula II:

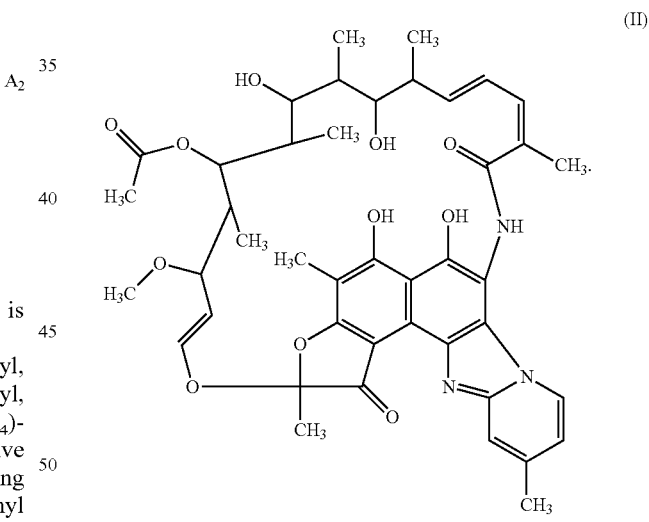

In certain embodiments, the antibiotic comprises one or more of a rifamycin, aminoglycoside, amphenicol, ansamycin, β-Lactam, carbapenem, cephalosporin, cephamycin, monobactam, oxacephem, lincosamide, macrolide, polypeptide, tetracycline, or a 2,4-diaminopyrimidine class antibiotic. Exemplary antibiotics of these classes are listed below.

Rifaximin exerts a broad antibacterial activity in the gastrointestinal tract against localized gastrointestinal bacteria that cause infectious diarrhea, including anaerobic strains. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res,* 14 (2), 51-56, (1994)).

Without wishing to be bound by any particular scientific theories, rifaximin acts by binding to the beta-subunit of the bacterial deoxyribonucleic acid-dependent ribonucleic acid (RNA) polymerase, resulting in inhibition of bacterial RNA synthesis. It is active against numerous gram (+) and (−) bacteria, both aerobic and anaerobic. In vitro data indicate rifaximin is active against species of *Staphylococcus, Streptococcus, Enterococcus*, and Enterobacteriaceae. Bacterial reduction or an increase in antimicrobial resistance in the colonic flora does not frequently occur and does not have a clinical importance. Rifaximin is currently approved in 17 countries outside the US and was licensed by the Food and Drug Administration (FDA) for the US in May 2004.

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

All documents, or portions of documents, cited in this application, including but not limited to patents, patent applications, articles, books, and treatises, are hereby expressly incorporated by reference in their entirety for any purpose.

One embodiment is a method of treating or preventing hepatic encephalopathy (HE) by administering a therapeutically effective amount of a gastrointestinal (GI) specific antibiotic to a subject. Examples of gastrointestinal antibiotics as used herein include rifamycin class antibiotics, such as rifaximin.

Embodiments of the invention relate to the discovery of the efficacy of gastrointestinal (GI) specific antibiotics for the treatment and prevention of Hepatic Encephalopathy. Embodiments relate to the use of GI specific antibiotics to prevent the onset of HE symptoms and also to lengthen the time to a first breakthrough HE episode. In one embodiment, the time to a first breakthrough HE episode was measured by an increase of the Conn score to Grade ≥2 (e.g., 0 or 1 to ≥2) or a Conn and asterixis score increase of one grade each for those subjects that have a baseline Conn Score of 0. In another embodiment, the time to breakthrough HE episode was measured by the time to any increase from baseline in either the Conn score (mental state grade) or asterixis grade, with Kaplan-Meier estimates of cumulative proportions of subjects with any increase at Days 28, 56, 84, 112, 140, and 168.

Another embodiment was a measurement of the time to a first HE-related hospitalization or the time to development of spontaneous bacterial peritonitis (SBP). Another embodiment was a mean change from baseline in blood ammonia concentration over time or a mean change from baseline in critical flicker frequency values over time. An additional embodiment was indicated by a mean daily lactulose consumption over time, shifts from baseline in Conn scores over time; or shifts from baseline in asterixis grades over time. Unless otherwise specified, a shift of a value is the change of that value from a baseline value.

Other measures of efficacy of the treatments described herein included mean change from baseline in Chronic Liver Disease Questionnaire (CLDQ) scores over time; mean change from baseline in Epworth Sleepiness Scale scores over time; and proportion of subjects who have an Epworth Sleepiness Scale score >10. The evaluation of severity of persistent hepatic encephalopathy may also be based, for example, on Conn scores.

In another embodiment, a subject suffering from, susceptible to or in remission from hepatic encephalopathy (HE) can be administered a rifamycin class antibiotic for between about 24 weeks and 24 months. In treating HE, the rifamycin class antibiotic may be administered to the subject for 12 months and longer, for example for a subject's entire life span. In one embodiment, the antibiotic is administered daily until the death of the subject.

In one embodiment, the invention relates to a method of decreasing a subject's risk of having a breakthrough event by administering to the subject a GI specific antibiotic. In one embodiment, the for subjects having a last HE episode equal to or greater than 90 days prior to starting on treatment, the risk of failure occurrence was reduced by 58%. In another embodiment, the risk of failure occurrence was reduced by between about 30-70%. In another embodiment, the risk was reduced by about 40% to 70%. In one embodiment the invention relates to decreasing the risk for episodes of overt hepatic encephalopathy in patients suffering from HE. In one embodiment, the patients are over 18 years of age.

In one embodiment, for subjects having a last HE episode more than 90 days prior to administration of a GI specific antibiotic, the risk of failure occurrence was decreased by between about 60%. In another embodiment, the risk of failure occurrence was decreased by between about 2%-80%.

In another embodiment, for subjects having two or fewer HE episodes in the six months prior to starting on treatment, the risk of a breakthrough HE episode was decreased by about a 56%. In one embodiment, the risk of a breakthrough HE episode was decreased by between about a 20%-70%.

In another embodiment, for subjects having greater than two HE episodes in the six months prior to starting on treatment, the risk of a breakthrough HE episode was reduced by about 63%. In another embodiment, the risk was reduced by about 30%-80%.

In one embodiment, the therapeutically effective amount of a gastrointestinal (GI) specific antibiotic comprises from between about 1000 mg to about 1200 mg/day.

In one embodiment, the therapeutically effective amount of a gastrointestinal (GI) specific antibiotic comprises from between about 1100 mg to about 1200 mg/day.

According to one embodiment, the therapeutically effective amount of a gastrointestinal (GI) specific antibiotic comprises about 1150 mg/day.

In another embodiment, the therapeutically effective amount is a dosage regimen of one capsule or tablet of the formulation two times each day, wherein each tablet comprises about 550 mg of the gastrointestinal (GI) specific antibiotic, such as rifaximin.

In one embodiment, the therapeutically effective amount is a dosage regimen of two capsules or tablets three times each day, wherein each capsule comprises about 200 mg of the gastrointestinal (GI) specific antibiotic.

In one embodiment, the therapeutically effective amount is a dosage of 275 mg of a gastrointestinal (GI) specific antibiotic administered four times per day. In another embodiment, 275 mg of a gastrointestinal (GI) specific antibiotic is administered as two dosage forms two times per day.

Another embodiment is a method of maintaining remission of HE in a subject by administering a GI specific antibiotic to the subject.

Another embodiment is a method of increasing time to hospitalization for treatment of HE by administering to the subject a GI specific antibiotic. In one embodiment, the administration of a GI specific antibiotic reduces hospitalization frequency by about 48%. In another embodiment, a GI specific antibiotic reduces hospitalization frequency by from between about 13% to about 69%.

In one embodiment, treatment with the gastrointestinal (GI) specific antibiotic maintains remission of HE in the subject.

In one embodiment, the GI specific antibiotic is administered to the subject for six months, one year, two to three years or daily until the subject's death.

In one embodiment, a Conn score for the subject is improved over baseline following administration of a GI specific antibiotic.

In one embodiment, a quality of life (QoL) measurement is improved from baseline with administration of a GI specific antibiotic over a course of treatment with rifaximin. In one embodiment, the improvised quality is an improvement in the AUC or TWA of the Chronic Liver Disease Questionnaire (CLDQ).

In one embodiment, the GI specific antibiotic is administered to the subject with lactulose, prior to treatment with lactulose, or following treatment with lactulose. In one embodiment the subject or a health care worker is advised to administer the GI specific antibiotic with lactulose. In one embodiment the subject or a health care worker is advised by a pharmaceutical label or insert to administer the GI specific antibiotic with lactulose in order to maintain remission of HE, or to decrease the risk for episodes of overt HE. In one embodiment, the subject or health care worker is advised to administer two 550 mg tablets of rifaximin twice daily with lactulose. Lactulose use may be titrated over time so that the subject maintains 2-3 soft stool bowel movements per day. In one embodiment the lactulose is administered in 15 ml dosages, wherein each 15 ml dosage contains 10 mg of lactulose. In a typical titration, the subject may start on one dosage, or a partial dosage, per day and then move up in 15 ml dosages over time until they reach an end point of 2-3 soft stool bowel movements per day.

In one embodiment, subjects in need of treatment for HE and having a Child-Pugh grade of A or B are treated with a GI specific antibiotic. In another embodiment, subjects in need of treatment for HE having a Child-Pugh grade of A or B are treated with a GI specific antibiotic in combination with lactulose. In another embodiment, subjects having a Child-Pugh grade of A or B, or their health care worker, are advised that they should be treated with a GI specific antibiotic. The advice can be oral or written advice, such as on a pharmaceutical label or package insert. In another embodiment, subjects having a Child-Pugh grade of A or B, or their health care worker, are advised that they should be treated with a GI specific antibiotic in combination with lactulose. In one embodiment, a subject in need of treatment for HE and having a Child-Pugh grade of less than C is treated with a GI specific antibiotic. In one embodiment, a subject in need of treatment for HE and having a Child-Pugh grade of less than C is treated with a GI specific antibiotic and lactulose.

In another embodiment, a subject in need of treatment for HE, or their health care worker is advised of the risk for anaphylaxis prior to treatment with a GI specific antibiotic.

In one embodiment, the GI specific antibiotic is administered with one or more of align, alinia, Lactulose, pentasa, cholestyramine, sandostatin, vancomycin, lactose, amitiza, flagyl, zegerid, prevacid, or miralax.

In one embodiment, following treatment with GI specific antibiotic, a Conn score (mental state grade) of a subject decreases.

In one embodiment, following treatment with a GI specific antibiotic, a Conn score increase from baseline is increased.

In one embodiment, following treatment with a GI specific antibiotic, a delay in time to an increase in Conn score is about 54%. For example, the percentage delay in time to increase in Conn score may be between about 30% to about 70%.

In another embodiment, administration of the GI specific antibiotic prevents an increase in Conn score. For example, administration of the GI specific antibiotic increases the time to an increase from baseline in a Conn score.

In one embodiment, administration of the GI specific antibiotic results in an increase of time to an increase from baseline in an asterixis grade.

In another embodiment, administration of the GI specific antibiotic results in a delay in the time to increase in asterixis grade.

In another embodiment, administration of the GI specific antibiotic results in an increase in time to first HE-related hospitalization.

In another embodiment, administration of the GI specific antibiotic results in an increase in the time to development of spontaneous bacterial peritonitis (SBP).

In another embodiment, administration of the GI specific antibiotic results in a decrease in blood ammonia concentration from baseline after administration of rifaximin. For example, the decrease in blood ammonia concentration may be from baseline to 170 days of about 6 µg/dL.

In another embodiment, administration of the GI specific antibiotic results in an increase in critical flicker frequency values from baseline after administration of rifaximin.

In another embodiment, administration of the GI specific antibiotic results in a decrease in daily lactulose consumption from baseline over time after administration with rifaximin.

In another embodiment, administration of the GI specific antibiotic results in a decrease in daily lactulose consumption is from between about 7 doses of lactulose to about 2 doses of lactulose.

In another embodiment, administration of the GI specific antibiotic results in a lactulose use that initially increases from baseline. For example, the lactulose use may be from between about 1 and about 30 days.

In another embodiment, administration of the GI specific antibiotic results in a shift in baseline in Conn scores over time after administration of rifaximin. For example, the shift in baseline in Conn scores may be from between about 1 to about 2.

In another embodiment, administration of the GI specific antibiotic results in a shift from baseline in asterixis grades over time.

In another embodiment, administration of the GI specific antibiotic results in a change from baseline in Chronic Liver Disease Questionnaire (CLDQ) scores over time.

In another embodiment, administration of the GI specific antibiotic results in a change from baseline in Epworth Sleepiness Scale scores over time after administration of rifaximin.

As is known, the Model for End-Stage Liver Disease (MELD) score can be utilized to predict liver disease severity based on serum creatinine, serum total bilirubin, and the international normalized ratio for prothrombin time INR. The MELD score and has been shown to be useful in predicting mortality in patients with compensated and decompensated cirrhosis. The maximum score given for MELD is 40. All values higher than 40 are given a score of 40.

In another embodiment, subjects having a MELD level of between about 1 to 24 responded to treatment for HE using administration of the GI specific. In another embodiment, subjects having a MELD level less than or equal to 10 responded to treatment with GI specific antibiotics. In another embodiment, subjects having a MELD level between 11 and 18 respond to treatment with GI specific antibiotics. In another embodiment, subjects having a MELD level between 19 and 24 respond to treatment with GI specific antibiotics. In one embodiment, subjects in need of treatment for HE and having a MELD score of 25 or less are treated with a GI specific antibiotic. In another embodiment, subjects in need of treatment for HE having a MELD score of 25 or less are treated with a GI specific antibiotic in combination with lactulose. In another embodiment, subjects having a MELD score of 25 or less are advised that they should be treated with a GI specific antibiotic. The advice can be oral or written advise, such as on a pharmaceutical label or package insert. In another embodiment, subjects having a MELD score of 25 or less are advised that they should be treated with a GI specific antibiotic in combination with lactulose.

One embodiment of the invention is a method of treating or preventing HE by administering 1100 mg of rifaximin per day to a patient for more than 28 days.

Another embodiment is a method of decreasing lactulose use in a subject.

This method includes: administering rifaximin to a subject daily that is being treated with lactulose, and tapering lactulose consumption. For example, the lactulose consumption may be reduced by 1, 2, 3, 4, 5, 6 or more unit dose cups of lactulose from a baseline level. Alternatively, the lactulose use may be reduced by 5, 10, 15, 20, 25, 30, 34, 40, 45, 50, 55, 60, 65, or 70 g lactulose from a baseline level. In one embodiment, the baseline use of lactulose is no use.

One embodiment of the invention is a method of maintaining remission of HE in a subject comprising administering 550 mg of rifaximin twice a day (BID) to the subject.

Another embodiment is a method of increasing time to hospitalization for treatment of HE comprising, administering to a subject 550 mg of rifaximin two times per day (BID).

The term "administration" or "administering" includes routes of introducing a GI specific antibiotic to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, eye drops, ointment, suppository, etc. administration by injection, infusion or inhalation; topical by lotion or ointment; and rectal by suppositories. Oral administration is preferred. The injection can be bolus or can be continuous infusion. Depending on the route of administration, a GI specific antibiotic can be coated with or disposed in a selected material to protect it from natural conditions that may detrimentally effect its ability to perform its intended function. A GI specific antibiotic can be administered alone, or in conjunction with either another agent or agents as described above or with a pharmaceutically-acceptable carrier, or both. A GI specific antibiotic can be administered prior to the administration of the other agent, simultaneously with the agent, or after the administration of the agent. Furthermore, a GI specific antibiotic can also be administered in a proform, which is converted into its active metabolite, or more active metabolite in vivo.

Administration "in combination with" one or more further therapeutic agents includes simultaneous (concurrent) and consecutive administration in any order.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved.

As used herein, an "increase" or "decrease" in a measurement, unless otherwise specified, is typically in comparison to a baseline value. For example, an increase in time to hospitalization for subjects undergoing treatment may be in comparison to a baseline value of time to hospitalization for subjects that are not undergoing such treatment. In some instances an increase or decrease in a measurement can be evaluated based on the context in which the term is used.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG).

The term "effective amount" includes an amount effective, at dosages and for periods of time necessary, to achieve the desired result, e.g., sufficient to treat or prevent HE in a patient or subject. An effective amount of a GI specific antibiotic may vary according to factors such as the disease state, age, and weight of the subject, and the ability of a GI specific antibiotic to elicit a desired response in the subject. Dosage regimens may be adjusted to provide the optimum therapeutic response. An effective amount is also one in which any toxic or detrimental effects (e.g., side effects) of a GI specific antibiotic are outweighed by the therapeutically beneficial effects.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with rifaximin, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment such as a Chronic Liver Disease Questionnaire (CLDQ), a slowed progression of a disease(s) or condition(s), a reduced severity of a disease(s) or condition(s), or a suitable assay(s) for the level or activity(ies) of a biomolecule(s), cell(s) or by detection of HE episodes in a subject. Amelioration may be transient, prolonged or permanent or it may be variable at relevant times during or after a GI specific antibiotic is administered to a subject or is used in an assay or other method described herein or a cited reference, e.g., within timeframes described infra, or about 1 hour after the administration or use of a GI specific antibiotic to about 28 days, or 1, 3, 6, 9 months or more after a subject(s) has received such treatment.

The "modulation" of, e.g., a symptom, level or biological activity of a molecule, or the like, refers, for example, that the symptom or activity, or the like is detectably increased or decreased. Such increase or decrease may be observed in treated subjects as compared to subjects not treated with a GI specific antibiotic, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after a GI specific antibiotic is administered to a subject or is used in an assay or other method described herein or a cited reference, e.g., within times descried infra, or about 1 hour of the administration or use of a GI specific antibiotic to about 3, 6, 9 months or more after a subject(s) has received a GI specific antibiotic.

The term "modulate" may also refer to increases or decreases in the activity of a cell in response to exposure to a GI specific antibiotic, e.g., the inhibition of proliferation and/or induction of differentiation of at least a sub-population of cells in an animal such that a desired end result is achieved, e.g., a therapeutic result of GI specific antibiotic used for treatment may increase or decrease over the course of a particular treatment.

The term "obtaining" as in "obtaining a GI specific antibiotic" is intended to include purchasing, synthesizing or otherwise acquiring a GI specific antibiotic.

The phrases "parenteral administration" and "administered parenterally" as used herein includes, for example, modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The language "a prophylactically effective amount" of a compound refers to an amount of a GI specific antibiotic which is effective, upon single or multiple dose administration to the subject, in preventing or treating HE.

Pharmaceutical Preparations

Embodiments also provide pharmaceutical compositions, comprising an effective amount of a rifaximin described herein and a pharmaceutically acceptable carrier. In a further embodiment, the effective amount is effective to treat a bacterial infection, Crohn's disease, hepatic encephalopathy, antibiotic associated colitis, and/or diverticular disease in a subject further suffering from hepatic insufficiency.

Embodiments also provide pharmaceutical compositions comprising rifaximin and a pharmaceutically acceptable carrier. Doses may be selected, for example on the basis of desired amounts of systemic adsorption, elimination half-life, serum concentration and the like. Embodiments of the pharmaceutical composition further comprise excipients, for example, one or more of a diluting agent, binding agent, lubricating agent, disintegrating agent, coloring agent, flavoring agent or sweetening agent. One composition may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In an embodiment, rifaximin is administered to the subject using a pharmaceutically-acceptable formulation, e.g., a pharmaceutically-acceptable formulation that provides sustained delivery of the rifaximin to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to rifaximin compositions containing rifaximin and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is preferably "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2)

starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a rifaximin forms disclosed herein include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred %, this amount will range from about 1% to about ninety-nine % of active ingredient, preferably from about 5% to about 70%, most preferably from about 10% to about 30%.

Methods of preparing these compositions include the step of bringing into association a rifaximin with the carrier and, optionally, one or more accessory ingredients. In general, the formulations are prepared by uniformly and intimately bringing into association a rifaximin with liquid carriers, or finely divided solid carriers, or both, and then, if necessary, shaping the product.

Compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a rifaximin as an active ingredient. A compound may also be administered as a bolus, electuary or paste.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The compositions may be in the form of tablets, capsules, powders, granules, lozenges, liquid or gel preparations. Tablets and capsules for oral administration may be in a form suitable for unit dose presentation and may contain conventional excipients. Examples of these are: binding agents such as syrup, acacia, gelatin, sorbitol, tragacanth, and polyvinylpyrrolidone; fillers such as lactose, sugar, maize-starch, calcium phosphate, sorbitol or glycine; tableting lubricants, such as magnesium stearate, silicon dioxide, talc, polyethylene glycol or silica; disintegrants, such as potato starch; or acceptable wetting agents, such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, e.g., sorbitol, syrup, methyl cellulose, glucose syrup, gelatin, hydrogenated edible fats, emulsifying agents, e.g., lecithin, sorbitan monooleate, or acacia; non-aqueous vehicles (including edible oils), e.g., almond oil, fractionated coconut oil, oily esters such as glycerine, propylene glycol, or ethyl alcohol; preservatives such as methyl or propyl p-hydroxybenzoate or sorbic acid, and, if desired, conventional flavoring or coloring agents.

The phrases "systemic administration," "administered systemically," "peripheral administration," and "administered peripherally," as used herein mean the administration of a GI specific antibiotic, drug or other material, such that it enters the subject's system and, thus, is subject to metabolism and other like processes, for example, subcutaneous administration.

The language "therapeutically effective amount" of a GI specific antibiotic refers to an amount of a GI specific antibiotic which is effective, upon single or multiple dose administration to the subject, in inhibiting the bacterial growth and/or invasion, or in decreasing symptoms, such as HE episodes, relating to bacterial growth in a subject. "Therapeutically effective amount" also refers to the amount of a therapy (e.g., a composition comprising a GI specific antibiotic), which is sufficient to reduce the severity of HE in a subject.

As used herein, the terms "prevent," "preventing," and "prevention" refer to the prevention of the recurrence, onset, or development HE episodes or more symptoms of HE. Preventing includes protecting against the occurrence and severity of HE episodes.

As used herein, the term "prophylactically effective amount" refers to the amount of a therapy (e.g., a composition comprising a GI specific antibiotic) which is sufficient to result in the prevention of the development, recurrence, or onset of HE episodes or to enhance or improve the prophylactic effect(s) of another therapy.

"Rifaximin", as used herein, includes solvates and polymorphous forms of the molecule, including, for example, α, β, γ, δ, ε, η, ζ, (and amorphous forms of rifaximin. These forms are described in more detail, for example, in U.S. Ser. No. 11/873,841; U.S. Ser. No. 11/658,702; EP 05 004 635.2, filed 3 May 2005; U.S. Pat. No. 7,045,620; U.S. 61/031,329; and G. C. Viscomi, et al., CrystEngComm, 2008, 10, 1074-1081 (April 2008). Each of these references is hereby incorporated by reference in entirety.

The forms of rifaximin can be advantageously used in the production of medicinal preparations having antibiotic activity, containing rifaximin, for both oral and topical use. The medicinal preparations for oral use may contain rifaximin α or β or γ together with other excipients, for example diluting agents such as mannitol, lactose and sorbitol; binding agents such as starchs, gelatines, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starchs, celluloses, alginates, gums and reticulated polymers; coloring, flavoring and sweetening agents.

Medicinal preparations may contain gastrointestinal specific antibiotics together with usual excipients, such as white petrolatum, white wax, lanoline and derivatives thereof, stearylic alcohol, red iron oxide, propylene glycol, talc, sodium lauryl sulfate, ethers of fatty polyoxyethylene alcohols, disodium edentate, glycerol palmitostearate, esters of fatty polyoxyethylene acids, sorbitan monostearate, glyceryl monostearate, propylene glycol monostearate, hypromellose, polyethylene glycols, sodium starch glycolate, methylcellulose, hydroxymethyl propylcellulose, sodium carboxymethylcellulose, microcrystalline cellulose, colloidal aluminium and magnesium silicate, titanium dioxide, propylene glycol, colloidal silicon dioxide, or sodium alginate.

As used herein, "breakthrough HE," includes, for example, an increase of the Conn score to Grade ≥2 (e.g., 0 or 1 to ≥2) or a Conn and Asterixis score increase of 1 grade each for those subjects that have a baseline Conn score of 0.

As used herein, "time to the first breakthrough HE episode," includes, for example, the duration between the date of first administration of rifaximin and the date of first breakthrough HE episode.

As used herein, the term "breakthrough HE event", is intended to include a marked, clinically significant deterioration in neurological function caused by toxic substances accumulating in the blood that cause a deleterious effect on self care, and often leads to hospitalization. Breakthrough HE event is also defined as an increase of a Conn Score to ≥2 (i.e., 0 or 1 to ≥2) or a Conn score and asterixis grade increase of 1 each for those subjects that have a baseline Conn score of 0.

Provided herein are methods for determining if a subject has a neurological condition by determining the CFF of a subject at two or more time points. In exemplary embodiments, time points can be 1, 2, 3, 4, 5, 6 or 7 days apart; or 2, 3, or 4 weeks apart; or 2, 3, 4, 5, 6, 7, 8, 9, 10, 11 or 12 months apart or any time point in between any two values. In other embodiments, a subject may be monitored at routine intervals for life.

The methods of the invention provide that a decrease in CFF between two or more time points is indicative that the probability of an HE breakthrough event is approaching. Moreover, if a subject has a CFF twa value at a time point that is less than 24 Hz, it is indicative that the subject has an increased probability of an HE event. Therefore, a decrease between CFF in two or more time points or a twa of 24 Hz or less is indicative that the subject has HE, has an increased chance of an HE breakthrough event, and/or should be treated with Rifaximin. Accordingly, based on the data collected to date, in one embodiment provided herein are methods of determining if a subject has HE, of predicting the occurrence of a breakthrough HE event, or determining the prognosis of a subject by determining a subject's CFF is below 24 Hz, wherein a CFF below 24 Hz is indicative that the subject has HE, is likely to have a breakthrough HE event, or has a poor prognosis. In certain embodiments, a CFF of less than 24 Hz is indicative that a GI specific antibiotic, e.g., rifaximin, should be administered.

Provided herein are prognostic methods based on determining the CFF or twa CFF wherein a twa CFF of less than 24 is indicative of poor prognosis, or wherein a decrease in CFF or twa CFF between measurements at different time points is indicative of poor prognosis. Poor prognosis includes the survival of the subject for less than 2, 3, 4, 5, 6, 7, 8 or more years or as described herein or in the opinion of a healthcare professional, the subject or a person observing the subject.

In other embodiments, provided herein are method for determining if a subject has HE or has an increased risk of having a HE breakthrough event by measuring the venous ammonia level in a subject at two or more time points, wherein an increase in the venous ammonia level is indicative that the subject has HE, has an increased chance of an HE breakthrough event, and/or should be treated with a GI specific antibiotic, e.g., rifaximin. In certain embodiments the venous ammonia level is a time weighted average venous ammonia level.

Venous ammonia concentration can be measured using methods that are known to one of skill in the art. The accuracy of ammonia determination is dependent on sample collection. Whole blood is preferred. In one specific method described herein, blood is collect blood from a stasis-free vein into an EDTA evacuated tube. The sample is placed in ice immediately after collecting and mixing. The sample is placed in a cold environment, e.g., on ice, for approximately ten minutes and then centrifuged. The plasma is separated from the sample within fifteen minutes of collection and frozen. Hemolyzed samples should not be used for further analysis.

The frozen sample is subjected to an enzymatic assay to determine the amount of ammonia present in the sample. The sample containing ammonia is mixed with α-ketoglutarate and reduced nicotinamide adenine dinucleotide phosphate (NADPH) to form L-glutamate and NADP and water. The reaction is catalyzed by glutamate dehydrogenase. The results are determined spectrophotometrically by monitoring the decrease in absorbance at 340 nm due to the oxidation of NADPH. This decrease is proportional to the ammonia concentration.

In other embodiments, provided herein are methods for determining if a subject has a neurological condition by measuring the CFF between two or more time points. A decrease in the CFF between time points is indicative that a subject has a neurological condition. In certain embodiments, the CFF is the twa of CFF events.

According to one embodiment of the teachings of the present invention, provided herein are a database having a data structure which contains a number of CFF or venous ammonia levels from subjects. Similarly, at least one of the databases includes a data structure which maintains a number of relationships between the CFF or venous ammonia levels and the disease state of the subjects and that defines the business rules for performing the methods of the present invention. These business rules can include defined methods for determining if a subject has HE or is at risk of having a breakthrough HE event. Likewise, the business rules can include defined methods for determining if a subject has a neurological condition. The diagnosis or prognosis can be optionally selected using the novel software of the systems and methods of the present invention. In this scenario, the systems and methods, including the novel program configurations, will automatically perform the methods of the present invention without additional user input.

Provided herein are methods for determining if a subject has a neurological condition by determining the CFF of a subject at two or more time points.

In particular, one such additional method provided herein includes novel software including a number of program modules or components located on a server within the system for creating and populating a database for use in the diagnostic or prognostic methods of the invention. In other words, in one embodiment, the systems and methods provide for the creation and management of a particular policy and policy management for a particular client. One of ordinary skill in the art will understand upon reading this disclosure that the various embodiments include novel software including a number of program modules or components located on the computer based system or network of the present invention, e.g. servers, sending remote clients, and receiving remote clients, for facilitating the methods of the present invention.

As used herein, "time to first HE-related hospitalization," includes, for example, the duration between the first dose of rifaximin and the date of first HE-related hospitalization.

As used herein, "time to an increase from baseline in the Conn score" includes, for example, the duration between the first dose of rifaximin and the date of first increase in Conn score.

As used herein, "time to an increase from baseline in the asterixis grade", includes, for example, the duration between the first dose of rifaximin and the date of first increase in asterixis grade.

As used herein, "mean change from baseline in the fatigue domain score of Chronic Liver Disease Questionnaire (CLDQ), at end of treatment (EOT)" is the mean score with a baseline from before the first administration of rifaximin.

As used herein, "mean change from baseline in blood ammonia concentration at EOT," includes the mean score with a baseline from before the first administration of rifaximin.

As used herein, the "time to diagnosis of spontaneous bacterial peritonitis (SBP)," includes, for example, the duration between the first dose of rifaximin and the date of first episode of SBP.

As used herein, the "mean change from baseline at each post-baseline in critical flicker frequency values," is measured, for example, from a baseline established before the first administration of rifaximin.

"GI specific antibiotic," and "GI antibiotic" as used herein include antibiotic known to have an effect on GI disease. For example, a rifamycin class antibiotic (e.g., rifaximin), neomycin, metronidazole, teicoplanin, ciprofloxacin, doxycycline, tetracycline, augmentin, cephalexin, penicillin, ampicillin, kanamycin, rifamycin, vancomycin, rifaximin, and combinations thereof are useful GI specific antibiotics. Even more preferable are GI specific antibiotics with low systemic absorption, for example, rifaximin. Low systemic absorption includes, for example, less than 10% absorption, less than 5% absorption, less than 1% absorption and less than 0.5% absorption. Low systemic absorption also includes, for example, from between about 0.01-1% absorption, from between about 0.05-1% absorption, from between about 0.1-1% absorption, from between about 1-10% absorption, or from between about 5-20% absorption.

As used herein, "subject" includes organisms which are capable of suffering from a bowel disorder or other disorder treatable by rifaximin or who could otherwise benefit from the administration of a rifaximin as described herein, such as human and non-human animals. Preferred human animals include human subjects. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Susceptible to a bowel disorder is meant to include subjects at risk of developing a bowel disorder or bowel infection, e.g., subjects suffering from hepatic failure or decreased haepatic function, immune suppression, subjects that have been exposed to other subjects with a bacterial infection, physicians, nurses, subjects traveling to remote areas known to harbor bacteria that causes travelers' diarrhea, etc.

The language "a prophylactically effective amount" of a compound refers to an amount of a compound of the invention of formula I, formula II, or otherwise described herein which is effective, upon single or multiple dose administration to the subject, in preventing or treating hepatic encephalopathy.

Another embodiment includes articles of manufacture that comprise, for example, a container holding a pharmaceutical composition suitable for oral administration of rifaximin in combination with printed labeling instructions providing a discussion of when a particular dosage form extends remission of HE or prevents or delays future episodes of HE. The dosage can be modified for administration to a subject suffering from HE, or include labeling for administration to a subject suffering from HE. Exemplary dosage forms and administration protocols are described infra. The composition will be contained in any suitable container capable of holding and dispensing the dosage form and which will not significantly interact with the composition and will further be in physical relation with the appropriate labeling. The labeling instructions may be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

In one embodiment, the instructions will inform and/or advise a health care worker, prescribing physician, a pharmacist, or a subject that they should advise a patient suffering from hepatic encephalopathy that administration of rifaximin may induce cytochrome P450. In another embodiment, the instructions will inform the subject and/or the healthcare provider that there is an extended time to remission or relapse of subjects that take rifaximin. In another embodiment, the instructions will inform the subject and/or the healthcare worker or provider that rifaximin does not significantly alter the $C_{max}$, $AUC_{0-t}$, or $AUC_{0-\infty}$ of midazolam. In another embodiment, the instructions will inform the subject and/or the healthcare worker or provider that rifaximin does not increase the risk of QT prolongation.

Packaged compositions are also provided, and may comprise a therapeutically effective amount of rifaximin tablets or capsules. Kits are also provided herein, for example, kits for treating HE in a subject. The kits may contain, for example, rifaximin and instructions for use when treating a subject for an HE. The instructions for use may contain prescribing information, dosage information, storage information, and the like.

Kits may include pharmaceutical preparations of the GI specific antibiotics along with pharmaceutically acceptable solutions, carriers and excipients.

Forms of rifaximin can be advantageously used in the production of medicinal preparations having antibiotic activity, containing rifaximin, for both oral and topical use. The medicinal preparations for oral use may contain one or more forms of rifaximin (for example, α or β or γ) together with other excipients, for example diluting agents such as mannitol, lactose and sorbitol; binding agents such as starchs, gelatines, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starchs, celluloses, alginates, gums and reticulated polymers; coloring, flavoring and sweetening agents.

Solid preparations of gastrointestinal specific antibiotics administrable by the oral route include for instance coated and uncoated tablets, soft and hard gelatin capsules, sugar-coated pills, lozenges, wafer sheets, pellets and powders in sealed packets.

Medicinal preparations may contain gastrointestinal specific antibiotics together with usual excipients, such as white petrolatum, white wax, lanoline and derivatives thereof, stearylic alcohol, red iron oxide, propylene glycol, talc, sodium lauryl sulfate, ethers of fatty polyoxyethylene alcohols, disodium edentate, glycerol palmitostearate, esters of fatty polyoxyethylene acids, sorbitan monostearate, glyceryl monostearate, propylene glycol monostearate, hypromellose, polyethylene glycols, sodium starch glycolate, methylcellulose, hydroxymethyl propylcellulose, sodium carboxymethylcellulose, microcrystalline cellulose, colloidal aluminium and magnesium silicate, titanium dioxide, propylene glycol, colloidal silicon dioxide, or sodium alginate.

West Haven Criteria (Conn Score):

Measurements of change in mental status may be done, for example, by the Conn score (also known as the West Haven score). The Conn score has been widely used as a measure of mental state in HE studies and is based on the criteria of Parsons-Smith as modified by Conn. Asterixis will not be considered when assessing the subject's status using the Conn scoring criteria listed below.

The scale used in the Conn scoring system is provided below.

Grade 0=No personality or behavioral abnormality detected

Grade 1=Trivial lack of awareness, euphoria or anxiety; shortened attention span; impairment of addition or subtraction Grade 2=Lethargy; disorientation for time; obvious personality change; inappropriate behavior Grade 3=Somnolence to semi-stupor, responsive to stimuli; confused; gross disorientation; bizarre behavior Grade 4=Coma; unable to test mental state HE is defined as a spectrum of neuropsychiatric abnormalities seen in patients with liver dysfunction, diagnosed after routine exclusion of other known neurologic disease. HE is a major complication of liver cirrhosis, affecting 30-45% patients. In 2006, the CDC listed cirrhosis as the 12th leading cause of death by disease in the U.S. HE affects the patient's consciousness, personality, intellect and neuromuscular function, and may range from a minimal disturbance in cognition, to coma.

Figure 15:
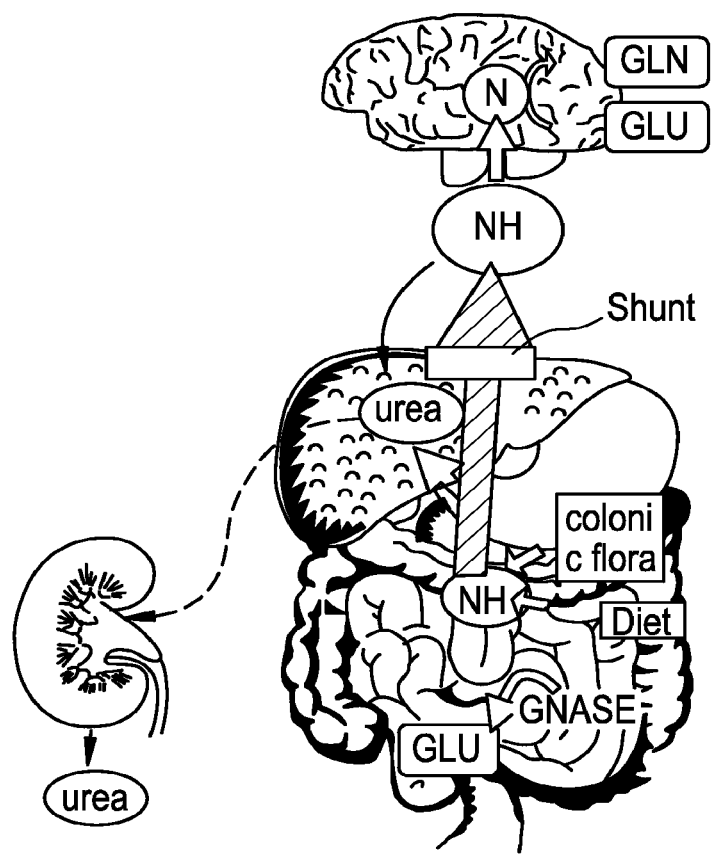
FIG. 15 shows the pathogenesis of HE.

In the gut, enteric bacteria act on nitrogen-containing substrates to generate ammonia. FIG. 15 represents the situation in unaffected HE subjects: ammonia is removed from the blood as it passes through the liver where it is converted to urea, and excreted by the kidneys. In cirrhosis, ammonia from the intestines bypasses the damaged liver as a result of vascular shunts. This increases blood ammonia, which passes into the brain generating glutamine from the amino acid glutamate. The excess glutamine causes many deleterious effects on brain function; it inhibits neurotransmission, interferes with mitochondrial energy metabolism, and causes swelling of astrocytes.

The clinical presentation of HE is classified according to the scheme shown in FIG. 16. HE associated with Cirrhosis—the most common by far—is type C. HE Type C is sub-classified into episodic, persistent and minimal categories. Episodic and persistent varieties are clinically readily apparent conditions, and hence are denoted as Overt. Episodic HE presents with impairment in all the neurological functions mentioned above. As the term episodic implies, there are periods between episodes when no distinctive symptoms are seen. Episodes may be precipitated by factors such as constipation, infection, dehydration, GI hemorrhage and certain medications. If the cause is not immediately identified, the episode is referred to as spontaneous.

HE episodes are usually reversible with treatment—but they're often recurring. HE is a clinical diagnosis made by some tools, including the West Haven, or Conn, Score. In use for about 30 years, The HESA scoring algorithm (FIG. 17) is a relatively new tool used for accurate assignment of Conn criteria. Neuromuscular dysfunction can be measured by eliciting asterixis, or flapping tremor. Blood ammonia levels are often measured to support the diagnosis. Neurophysiological tests, such as critical flicker frequency and EEG, are potentially very useful to support the clinical findings. The Conn criteria use an increasing grade to associate with increasing neurological impairment, (ranging from 0=no impairment to 4=coma)

Grades 1, 2, and 3 represent an worsening in impairment in:
Consciousness—ranging from a trivial lack of awareness to somnolence;
impairment in intellectual ability and alterations in personality
This assessment can be conducted quickly, requires minimal intervention from the examiner or cooperation from the patient,
And we often use information from family or caregivers to help gauge the severity of HE episodes when the patient is confused.

While patients with grade 1 HE can be managed at home by a caregiver, any escalation to grade 2 or higher may require hospitalization and even management in intensive care. The Conn criteria use an increasing grade to associate with increasing neurological impairment, (ranging from 0=no impairment to 4=coma). Grades 1, 2, and 3 represent an worsening in impairment in: consciousness; intellectual ability and alterations in personality. This assessment can be conducted quickly, requires minimal intervention from the examiner or cooperation from the patient, information from family or caregivers is often used to gauge the severity of HE episodes.

While patients with grade 1 HE can be managed at home by a caregiver, any escalation to grade 2 or higher may require hospitalization and even management in intensive care.

There is a similar grading system for asterixis. If an HE patient is asked to hold out their hands just so, a jerky so called asterixis or flapping tremor will be observed. The number of beats is counted and scored from zero for none to four for almost continuous flapping. This is a simple test but requires a cooperative and conscious patient.

Figure 18:
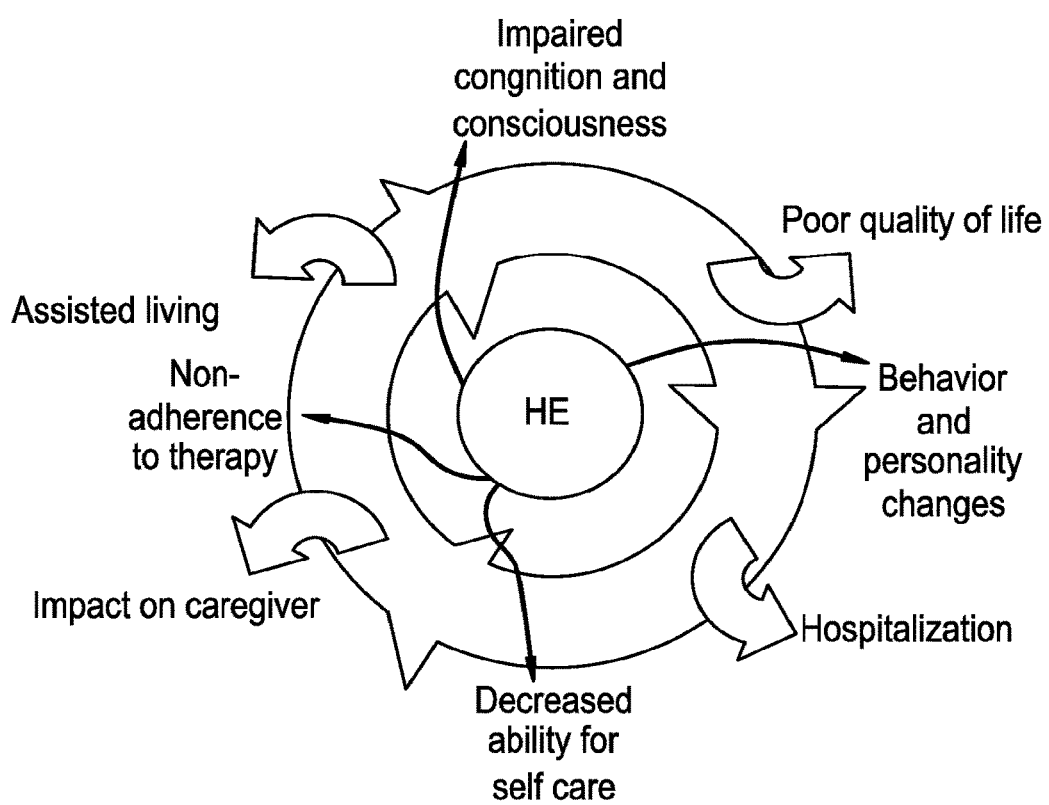
FIG. 18 shows the impact of HE on the patient and caregiver.

HE presents a vicious cycle of dysfunction and disability that has a dramatic effect on patients, their families and the healthcare system. Early on, impairments in behavior, personality, intellect and consciousness affect the patient's social and family life and ability to hold employment. As the condition worsens, it impacts capacity for self care, medication compliance, lack of compliance further intensifies HE symptoms and frequency of episodes. As a result, patients may need in-home assistance and often land in the ER or hospital beds. Severe HE can be a life threatening event, but it more commonly devastates the QOL of patients and their families; some caregivers liken the experience to caring for unpredictably episodic Alzheimer's disease. Impact on caregiver is shown in FIG. 18.

Figure 19:
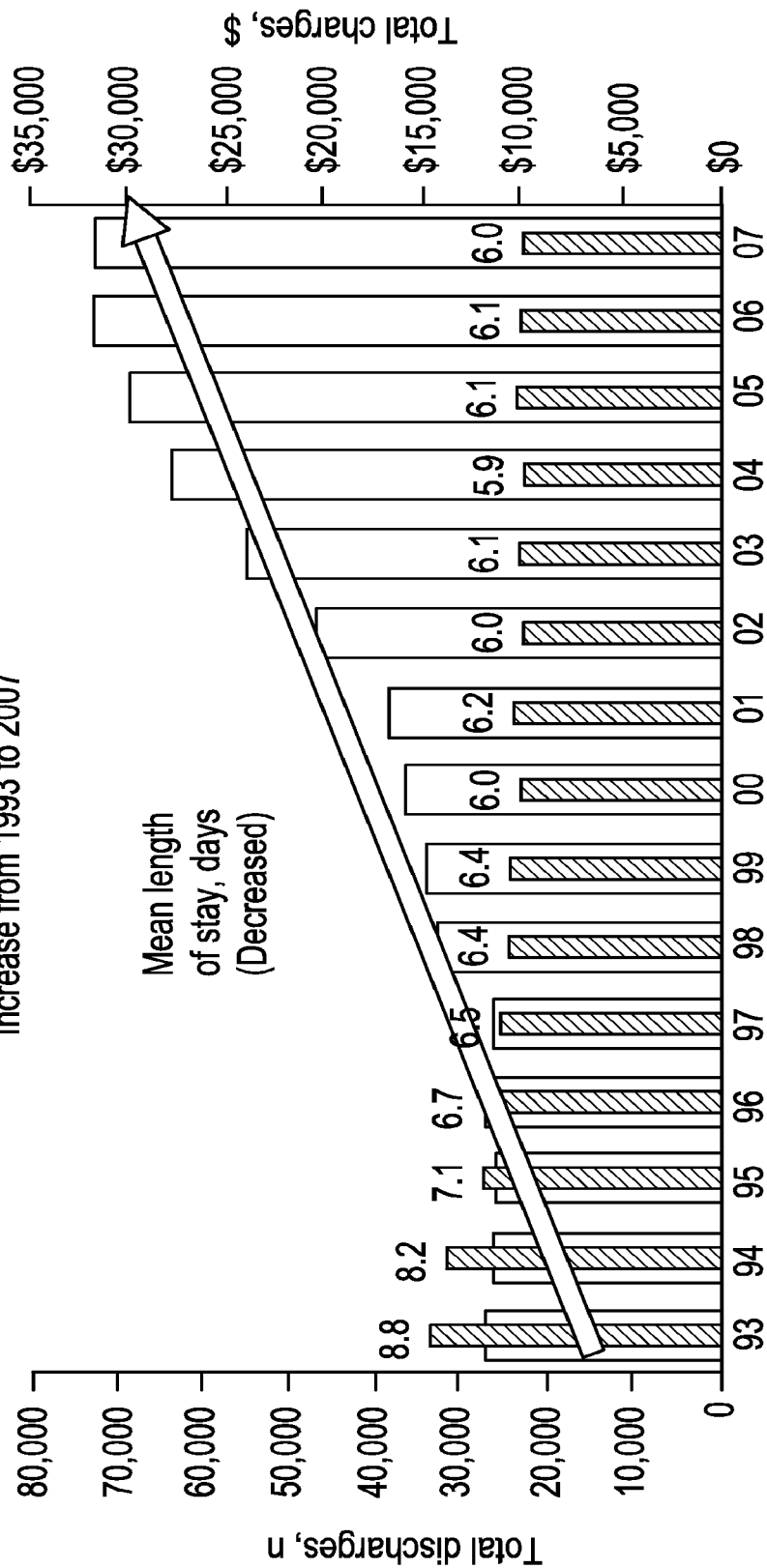
FIG. 19 depicts HE hospitalizations and economic impact.

In terms of the impact on healthcare, the number of HE discharges more than doubled between 1993 to 2007. See FIG. 19. Costs increased—from about 13 k to 30 k per hospitalization. So, the goals for HE Therapy include, for example, bringing acute episodes to quick resolution, and preventing recurrent episodes. To achieve these goals, we need a safe and effective therapy that is well tolerated for long-term treatment. There are serious limitations to the long-term use of the currently approved therapies. The most common, Lactulose, a non-absorbable disaccharide, targets the gut flora responsible for ammonia production. It exerts its effects mainly by purging, with frequent bowel movements. Lactulose therapy relies on dose self-titration, aim is for 2-3 loose stools a day—unfortunately this goal is often exceeded. At ten unpredictable loose stools per day, leaving home—even for a short walk to the store—may become impossible or embarrassing. Patients go on disability because of Lactulose rather than the HE it was prescribed for. Severe diarrhea can cause dehydration and electrolyte abnormalities that may even precipitate an HE episode. Nausea is not uncommon. Understandably, these factors can lead to poor adherence and limit long term use.

Another approved treatment is neomycin. However, long-term use is severely limited by its damaging side effects which include nephrotoxicity and sensorineural hearing loss—for which patients with advanced liver disease are most susceptible. Not surprisingly, the safety profile of neomycin is not conducive to long-term therapy. Given the limitations with both lactulose and neomycin—there clearly is an unmet medical need for a safe, effective, and well-tolerated long-term therapy. Hepatic encephalopathy is a serious neurological complication of advanced liver disease that disrupts quality of life, ability for self care and compliance, and results in frequent hospitalization There are limited therapeutic options for HE and there remains an unmet medical need for a safe, effective, and well-tolerated therapy for long-term treatment. There has not been a new treatment for this debilitating disease for 30 years. Physicians have been sufficiently impressed with the efficacy, tolerability and safety data on rifaximin- and their favorable experience with this drug, even prior to the exciting new trial data you will see today—to make rifaximin quite possibly the most widely used antibiotic therapy for HE.

Study 3001 was designed to continuously monitor patients to ensure the validity and completeness of HE breakthrough capture. Following screening, subjects entered a treatment period that included weekly visits and/or phone calls with patients and caregivers. Subjects were followed for the protocol specified 168 days. Complete capture of breakthrough events as well as mortality and provided assurance of the validity of the study outcome. Narratives for each subject experiencing HE breakthrough, AE's resulting in termination, SAEs or death were provided in the NDA. Key entry criteria included:

Patients with advanced liver disease,

Presenting with at least 2 episodes of HE within 6 months of screening; documented in medical records with a severity equivalent to a Conn score $\geq 2$;

At both screening and baseline, subjects had a Conn score of 0 or 1, a MELD less than or equal to 25 and were required to have a caregiver who assented to the patient's participation;

Patients were excluded if they had a condition that could interfere with the protocol assessments, used alcohol within 14 days, sedatives within 7 days or evidence of current drug dependence;

HESA combines both the clinical components of Conn and neuropsychological tests. Administration requires ~45 minutes. It was used as a tool to establish consistent scoring of Conn across study centers. It provided a continuous reinforcement of standards and definitions FIG. 17 succinctly covers the clinical assessments and neuropsychological testing of HESA. Rifaximin provided a significant, protective effect as demonstrated by a 58% reduction in the risk of breakthrough HE with a highly significant p-value. The benefit of rifaximin is striking in that 78% of the patients now had zero events over 6 months. This is in contrast to the placebo group where only 54% maintain remission from HE. In a sick population who suffers from frequent adverse events, restricted living and a shortened life span, rifaximin is able to provide a meaningful benefit by preventing deterioration in their mental status and motor skills.

There were a total of 104 events recorded from 299 participating patients. For the components, we are using descriptive statistics using proportion analysis meeting the condition. 86 events, or 83% of the total events, consisted of patients experiencing a Conn Score of $>=2$, 37% placebo and 20% rifaximin, resulting in a highly significant p-value.

Eighteen (18) events, or 17% of the total events, are included in this next category of patients experiencing a worsening of Conn and asterixis grade of 1 each. 9% of placebo and 2% of rifaximin, also providing a highly significant p-value.

Consistency of effect aids in determining whether the benefit is derived from one or a few subgroups or if the effect is seen generally across all patient subgroups. Importantly, we tested for a treatment by subgroup interaction to ascertain homogeneity in response across subgroups. None of the subgroups tested for a significant interaction. Hazard ratios less than 1 indicate that the outcome favors rifaximin and greater than 1 favors placebo. The result seen in all subgroups consistently reflect the clinical benefit in favor of rifaximin. This consistency of outcome, coupled with the absence of a subgroup by treatment interaction, support the robustness of the overall treatment effect.

This effect is maintained across subgroups of varying degrees of severity as it relates to MELD and Child-Pugh. Again, there is no subgroup by treatment interaction here and the estimate of the treatment effect is approximately the same across all groups. In total, the subgroup analyses demonstrate the remarkable consistency of the risk reduction seen in the Primary Endpoint analysis across all groups.

The analysis of the time to HE-related hospitalization results in a 50% reduction in risk with a significant p-value. A large proportion of HE episodes resulted either in direct hospitalization or occurred during the hospitalization. It was shown that time to HE-caused hospitalization (defined as time to hospitalization directly resulting from HE), and time to all-cause hospitalization were reduced with rifaximin, and these analyses show 56% and 30% reductions in risk respectively.

Other endpoints included, for example, the time to first worsening in Conn or Asterixis Scores regardless of whether that change led to a breakthrough HE event; patient reported Quality of life, in particular fatigue, using the CLDQ; changes in blood ammonia, believed to be the primary neurotoxin responsible for the HE; and the Critical flicker frequency. The time to first time worsening in Conn Score reflects a 54% reduction in risk. Time to worsening of asterixis or hand flapping, shows a 35% reduction with a trending p-value. These data represent the changes in each domain throughout the course of the trial. The results demonstrate that rifaximin treated patients feel better. The questionnaire uses a 7-point Likert scale with 1=All the time and 7 being none of the time. Thus, greater values represent better quality of life. The change seen here in each subscale suggests a movement on each scale of 1 category improvement over placebo. The changes we see in ammonia and CFF are statistically significant and reflect improvement in favor of rifaximin. These results support the treatment effect of rifaximin.

Analyses were undertaken to assess the sensitivity and specificity of breakthrough HE. Patients with lower CFF and fatigue assessments, and a higher blood ammonia concentration had a greater likelihood of experiencing an HE breakthrough. These data provide further evidence that the primary endpoint is objective and clinically meaningful. For 3002, breakthrough HE data were collected to provide supportive information regarding rifaximin's effect of preventing recurrence of HE.

Three populations were treated in study 3002, including, rifaximin-treated patients from Study 3001; crossover placebo-treated patients from Study 3001; and new HE patients.

Rifaximin subjects who maintained remission throughout 3001 demonstrated continued benefit during their participation in 3002. The incidence of breakthrough HE for rifaximin subjects was lower than the 3001 placebo group demonstrating a 90% reduction in the risk of breakthrough HE. Note that approximately 60% of these patients remain free of breakthrough after almost 3 years. 82 placebo treated subjects from the 3001 study were enrolled in 3002 and were followed for breakthrough. Once in the open-label and receiving rifaximin, we see a 79% risk reduction compared to their experience in the 3001 trial.

The all Rifaximin population demonstrates a 2.6-fold increase risk of all-cause mortality for subjects who achieved a Conn score of at least 2.

The following example will discuss new and novel aspects of rifaximin:

In vitro and in vivo pharmacological actions of rifaximin that may contribute to its clinical benefit;

Rifaximin's ADME properties, including pharmacokinetics and its excretory and metabolic fate; and Drug-drug interaction studies.

Mechanistically, rifaximin binds to the beta-subunit of bacterial DNA dependent RNA polymerase resulting in inhibition of bacterial RNA synthesis. In vivo, rifaximin ameliorates bacterial diarrheal symptoms and the majority of the dose is not absorbed and it concentrates in the gut, with high gut lumen concentrations, approximately 8000 µg/g of stool. Interestingly, treatment of travelers' diarrhea occurs without significant alteration to the overall intestinal pathogen burden.

In vitro, rifaximin has multiple effects at subinhibitory concentrations, including, for example, increasing plasmid cured, reducing plasmid transfer, and reducing virulence.

We have observed effects of rifaximin on mammalian cells, including, for example, detoxification pathways such as P-gp and 3A4 may be upregulated in the gut. Rifaximin renders epithelial cells resistant to bacterial colonization and internalization independent of the effects on bacteria and reduces production and absorption of gut-derived neurotoxins, the primary example being ammonia, which lead to HE in liver-impaired patients.

In this example, 50 patients treated with rifaximin 1200 mg/day showed statistically significant blood ammonia reduction. This reduction was accompanied by significant improvement in overall HE grade and individual measures of HE. While discrete blood ammonia concentrations may be variable, serial measurements in individual patients have been associated with HE severity.

Rifaximin is a member of the rifamycin class of antibiotics. The functional group shown in green differentiates rifaximin from other rifamycins and leads to gut-specific activity.

Rifaximin is categorized as BCS 4; poorly soluble and poorly absorbed. It is also a substrate of P-glycoprotein, an efflux transporter. These properties result in very low oral absorption. The small fraction that is absorbed is cleared by three mechanisms: billiary, metabolic and renal. Rifaximin undergoes first pass elimination via biliary excretion as unchanged rifaximin. There is one known metabolite; nearly undetectable in healthy subjects, and very low in HE patients, approximately 2.5% of parent exposure. In both healthy and liver disease subjects, rifaximin renal clearance is <0.4%. Orally administered rifaximin is eliminated almost entirely as unchanged rifaximin in the feces. Steady-state rifaximin pharmacokinetics was examined in healthy subjects and in liver impaired subjects. Exposure is quite low in all populations studied.

Figure 20:
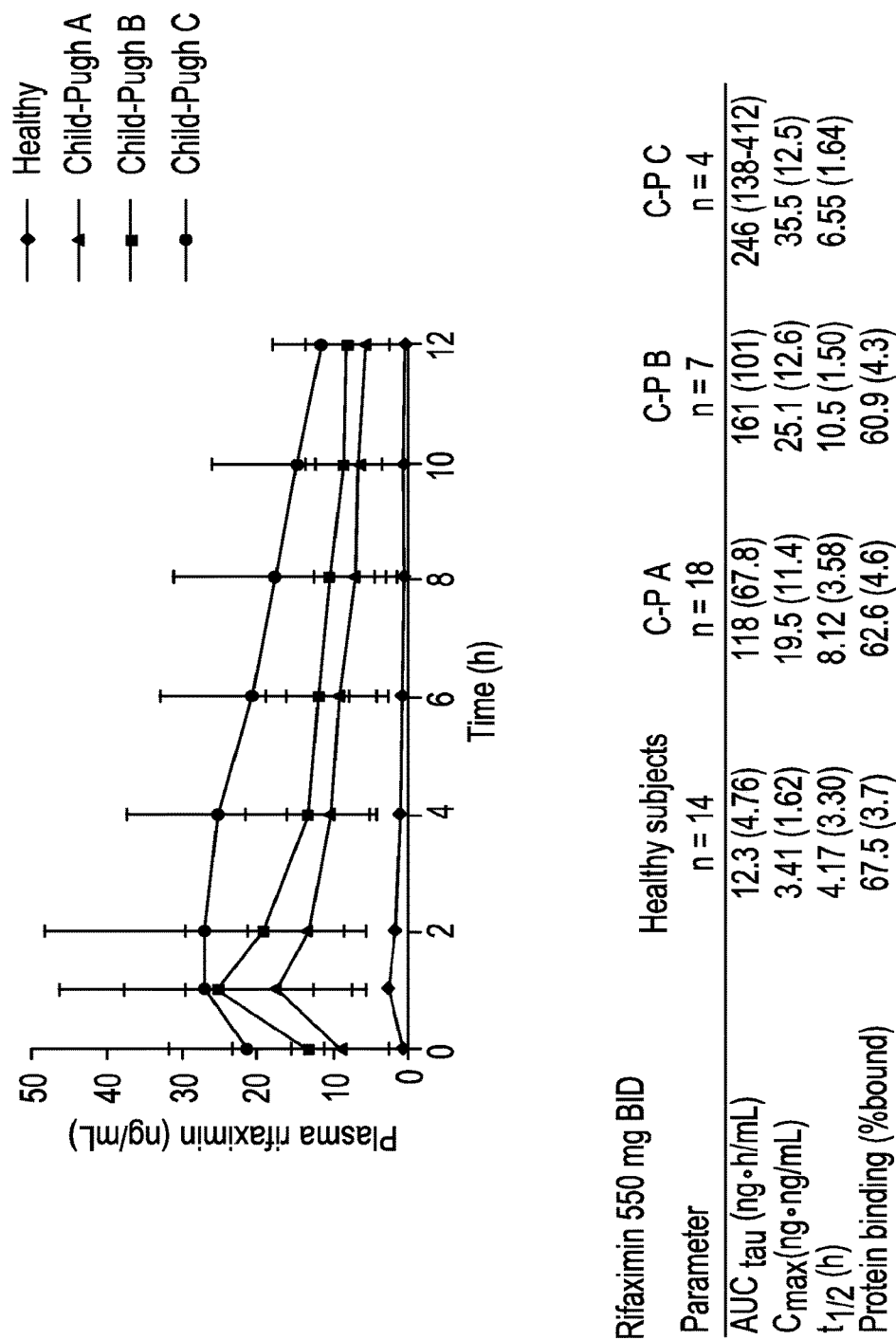
FIG. 20 shows the influence of Liver Impairment on Rifaximin PK.

In healthy volunteers, mean Cmax is less than 4 ng/mL. See FIG. 20. As liver impairment increases, AUC and Cmax increase correspondingly. Even at their highest, exposures remain low, in the ng/mL range. Increased exposure in liver impaired patients is well described in the literature, and may be attributed to several factors, including, for example, protein binding, reduced liver blood flow and reduced metabolic capability. Limited access to the liver due to blood flow shunting around the liver, and reduced metabolism due to impaired hepatocyte enzyme activity, may reduce hepatic clearance. Either or both of the latter two factors may be responsible for reducing clearance of rifaximin and increasing exposure in liver impaired patients.

Figure 21:
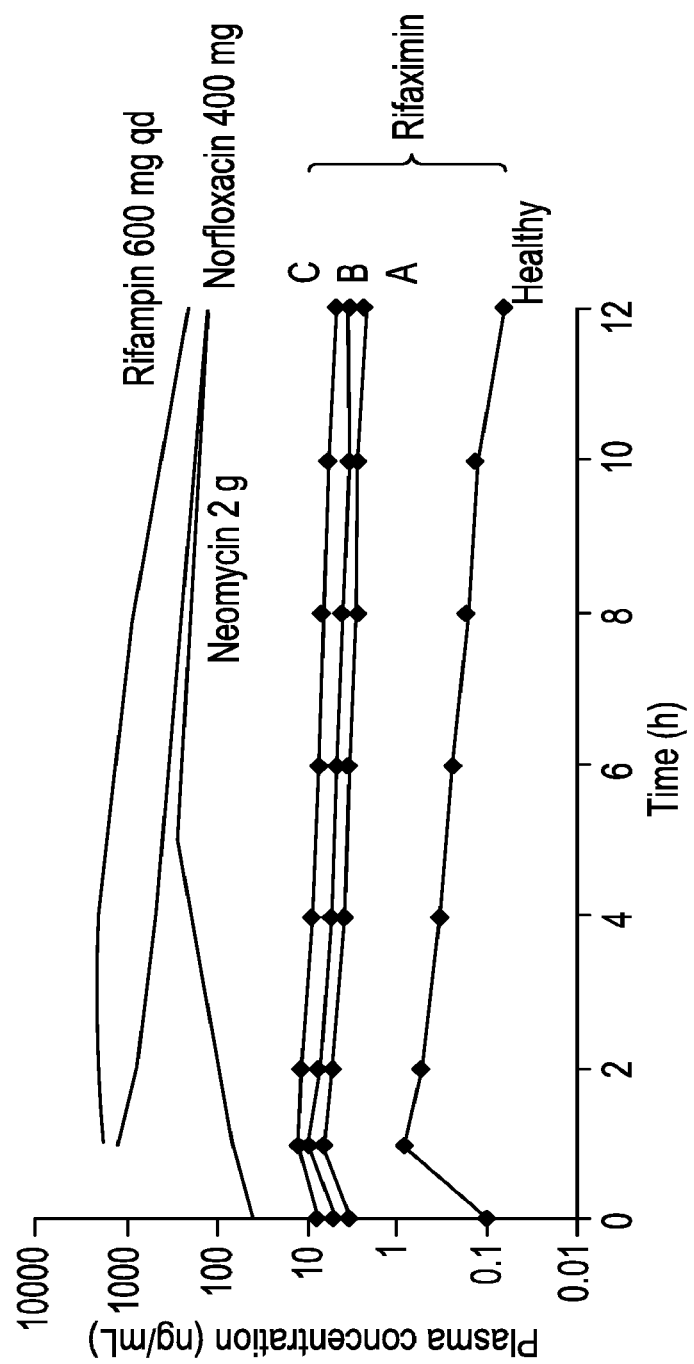
FIG. 21 demonstrates that rifaximin exposure is significantly lower than other antibiotic exposures. Well et al., Int J Antimicrob Agents 10 (1998) 31-38. In patients with greatest liver impairment, rifaximin exposure is >200-fold lower than rifampin exposure; >35-fold lower than norfloxacin exposure; and ≥10-fold lower than neomycin exposure.

To put this exposure into further perspective see FIG. 21 which shows rifaximin data in comparison with other antibiotics, on a log scale because of the wide differences.

Figure 23:
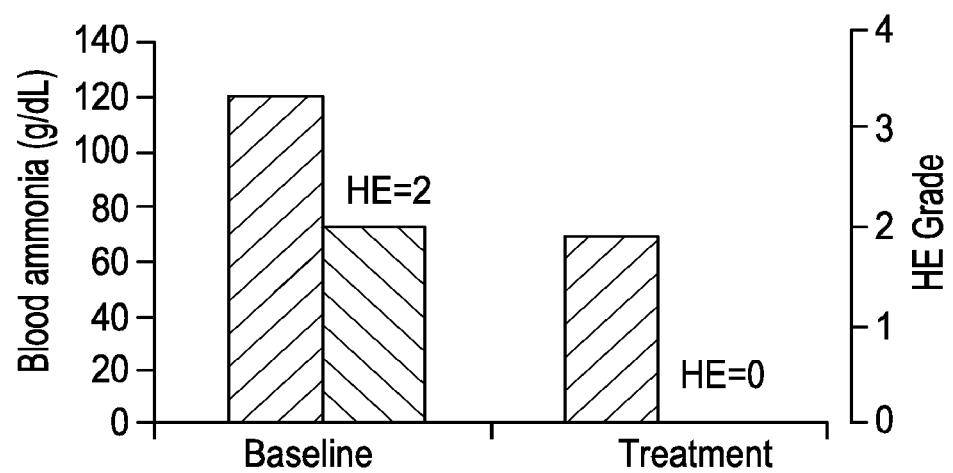
FIG. 23 shows the effect on blood ammonia. Rifaximin 1200 mg/day for 5-10 days decreased blood ammonia ($p<0.0001$). Corresponding improvement in HE grade ($p<0.0001$), neurological, neuropsychiatric, and psychometric parameters. Correlation between ammonia reduction over time and HE was examined.

Patients with greatest liver impairment and highest plasma exposure have rifaximin levels more than 200-fold lower than those achieved with a systemic antibiotic, like rifampin—shown in blue. It's also more than 10-fold lower than exposures observed with oral neomycin—shown here in pink—which is considered to be non-absorbed. Norfloxacin also is used commonly in this population, for SBP prophylaxis; it's a systemic antibiotic with plasma exposures greater than 35-fold higher than rifaximin. The potential for rifaximin to cause drug-drug interactions was explored here. Rifaximin does not significantly inhibit any major P450 drug metabolizing enzyme, P-glycoprotein, or BSEP in subjects with normal liver function. Knowing that other members of this class can cause interactions by upregulating important drug metabolizing enzymes, particularly CYP3A4, we examined the potential for this induction in clinical studies. Rifaximin's effect on midazolam, a classic CYP3A4 substrate, was studied in healthy volunteers. After 16 days of rifaximin 550 mg TID, a dose 50% higher than that used for HE, midazolam's AUC was reduced by 10%. See FIG. 22. In contrast, rifampin reduces midazolam AUC by 95% in similar experiments. This difference reflects not only an in vitro potency difference between rifampin and rifaximin, but an in vivo disposition difference between the two compounds in terms of rifaximin's low liver and systemic exposure. Based on these data we do not anticipate clinically significant drug interactions in subjects with normal liver function. In summary, in vitro and in vivo data indicate that rifaximin has bacteriostatic mechanisms as well as the ability to reduce bacterial adhesion and virulence. It lowers ammonia levels (See FIG. 23), which is linked to improvement in HE patients. The essential distinction between rifaximin and other rifamycins is its extremely low solubility and oral absorption, resulting in gut-targeted therapeutic effects and limited systemic exposure. Although liver disease leads to increased systemic exposure of rifaximin, the highest exposures seen with rifaximin are substantially lower than what's observed with other systemic and unabsorbed oral antibiotics. With this low systemic exposure comes a minimized drug-drug interaction risk.

Embodiments of the invention relate to all of the topical preparations, for instance ointments, pomades, creams, gels and lotions.

In solid dosage forms of rifaximin for oral administration (capsules, tablets, pills, dragees, powders, granules and the like), the active ingredient is typically mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) colouring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of rifaximin include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to rifaximin may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions for rectal or vaginal administration may be presented as a suppository, which may be prepared by mixing rifaximin with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions which are suitable for vaginal administration also include pessaries, tampons, creams, gels, pastes, foams or spray formulations containing such carriers as are known in the art to be appropriate.

Dosage forms for the topical or transdermal administration of rifaximin includes powders, sprays, ointments, pastes, creams, lotions, gels, solutions, patches and inhalants. Rifaximin may be mixed under sterile conditions with a pharmaceutically-acceptable carrier, and with any preservatives, buffers, or propellants which may be required.

Ointments, pastes, creams and gels may contain, in addition to rifaximin, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to rifaximin, excipients such as lactose, talc, silicic acid, aluminium hydroxide, calcium silicates and polyamide powder, or mixtures of these substances. Sprays can additionally contain customary propellants, such as chlorofluorohydrocarbons and volatile unsubstituted hydrocarbons, such as butane and propane.

Rifaximin can be alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

An aqueous aerosol is made, for example, by formulating an aqueous solution or suspension of the agent together with conventional pharmaceutically-acceptable carriers and stabilizers. The carriers and stabilizers vary with the requirements of the particular compound, but typically include non-ionic surfactants (Tweens®, Pluronics®, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration may comprise rifaximin in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, to prolong the effect of a drug, it is desirable to alter the absorption of the drug. This may be accomplished by the use of a liquid suspension of crystalline, salt oramorphous material having poor water solubility. The rate of absorption of the drug may then depend on its rate of dissolution which, in turn, may depend on crystal size and crystalline form. Alternatively, delayed absorption of a drug form is accomplished by dissolving or suspending the drug in an oil vehicle.

Injectable depot forms are made by forming microencapsule matrices of rifaximin in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

When the rifaximin is administered as a pharmaceutical, to humans and animals, it can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected rifaximin which may be used in a pharmaceutical compositions of the present invention, is formulated into pharmaceutically-acceptable dosage forms by methods known to those of skill in the art.

Actual dosage levels and time course of administration of the active ingredients in the pharmaceutical compositions may be varied so as to obtain an amount of the active ingredient which is effective to achieve the desired therapeutic response for a particular subject, composition, and mode of administration, without being toxic to the subject. An exemplary dose range is from 25 to 3000 mg per day.

XIFAXAN, a tradename for rifaximin, is approved for the following two uses:

1) Traveler's diarrhea: Rifaximin 200 mg are indicated for the treatment of patients (≥12 years of age) with travelers' diarrhea caused by noninvasive strains of *Escherichia coli*. Rifaximintablets should not be used in patients with diarrhea complicated by fever or blood in the stool or diarrhea due to pathogens other than *Escherichia coli*.

2) Hepatic encephalopathy: Rifaximin tablets 550 mg are indicated for the maintenance of remission of hepatic encephalopathy in patients ≥18 years of age.

To reduce the development of drug-resistant bacteria and maintain the effectiveness of rifaximin, and other antibacterial drugs, rifaximin when used to treat infection should be used only to treat or prevent infections that are proven or strongly suspected to be caused by susceptible bacteria. When culture and susceptibility information are available, they should be considered in selecting or modifying antibacterial therapy. In the absence of such data, local epidemiology and susceptibility patterns may contribute to the empiric selection of therapy.

XIFAXAN, a tradename for rifaximin, is approved for the following two uses:

1) Travelers' Diarrhea

Rifaximin 200 mg is indicated for the treatment of patients (≥12 years of age) with travelers' diarrhea caused by noninvasive strains of *Escherichia coli*.

Rifaximin should not be used in patients with diarrhea complicated by fever or blood in the stool or diarrhea due to pathogens other than *Escherichia coli*.

2) Hepatic Encephalopathy

Rifaximin 550 mg is indicated for reduction in risk of overt hepatic encephalopathy (HE) recurrence in patients ≥18 years of age. In the trials of rifaximin for HE, 91% of the patients were using lactulose concomitantly. Differences in the treatment effect of those patients not using lactulose concomitantly could not be assessed.

Rifaximin has not been studied in patients with MELD (Model for End-Stage Liver Disease) scores >25, and only 8.6% of patients in the controlled trial had MELD scores over 19. There is increased systemic exposure in patients with more severe hepatic dysfunction.

Rifaximin can be administered orally with or without food. For treatment of travelers' diarrhea patients should take one 200 mg tablet three times a day for 3 days. For hepatic encephalopathy patients should take one 550 mg tablet two times a day.

Rifaximin tablets are contraindicated in patients with a hypersensitivity to rifaximin, any of the rifamycin antimicrobial agents, or any of the components in rifaximin tablets. Hypersensitivity reactions have included exfoliative dermatitis, angioneurotic edema, and anaphylaxis.

Rifaximin was not found to be effective in patients with diarrhea complicated by fever and/or blood in the stool or diarrhea due to pathogens other than *Escherichia coli*.

Discontinue rifaximin use if diarrhea symptoms get worse or persist more than 24-48 hours and alternative antibiotic therapy should be considered.

Rifaximin is not effective in cases of travelers' diarrhea due to *Campylobacter jejuni*. The effectiveness of rifaximin in travelers' diarrhea caused by *Shigella* spp. and *Salmonella* spp. has not been proven. Rifaximin should not be used in patients where *Campylobacter jejuni*, *Shigella* spp., or *Salmonella* spp. may be suspected as causative pathogens.

*Clostridium difficile*-associated diarrhea (CDAD) has been reported with use of nearly all antibacterial agents, including rifaximin, and may range in severity from mild diarrhea to fatal colitis. Treatment with antibacterial agents alters the normal flora of the colon which may lead to overgrowth of *C. difficile*.

*C. difficile* produces toxins A and B which contribute to the development of CDAD. Hypertoxin producing strains of *C. difficile* cause increased morbidity and mortality, as these infections can be refractory to antimicrobial therapy and may require colectomy. CDAD must be considered in all patients who present with diarrhea following antibiotic use. Careful medical history is necessary since CDAD has been reported to occur over two months after the administration of antibacterial agents.

If CDAD is suspected or confirmed, ongoing antibiotic use not directed against *C. difficile* may need to be discontinued. Appropriate fluid and electrolyte management, protein supplementation, antibiotic treatment of *C. difficile*, and surgical evaluation should be instituted as clinically indicated.

Prescribing rifaximin for travelers' diarrhea in the absence of a proven or strongly suspected bacterial infection or a prophylactic indication is unlikely to provide benefit to the patient and increases the risk of the development of drug-resistant bacteria.

There is increased systemic exposure in patients with severe hepatic impairment. Animal toxicity studies did not achieve systemic exposures that were seen in patients with severe hepatic impairment. The clinical trials were limited to patients with MELD scores <25. Therefore, caution should be exercised when administering rifaximin to patients with severe hepatic impairment (Child-Pugh C).

The safety of rifaximin 200 mg taken three times a day was evaluated in patients with travelers' diarrhea consisting of 320 patients in two placebo-controlled clinical trials with 95% of patients receiving three or four days of treatment with rifaximin. The population studied had a mean age of 31.3 (18-79) years of which approximately 3% were ≥65 years old, 53% were male and 84% were White, 11% were Hispanic.

Discontinuations due to adverse reactions occurred in 0.4% of patients. The adverse reactions leading to discontinuation were taste loss, dysentery, weight decrease, anorexia, nausea and nasal passage irrigation.

All adverse reactions for rifaximin 200 mg three times daily that occurred at a frequency ≥2% in the two placebo-controlled trials combined are provided in Table 26. (These include adverse reactions that may be attributable to the underlying disease.)

The following adverse reactions, presented by body system, have also been reported in <2% of patients taking rifaximin in the two placebo-controlled clinical trials where the 200 mg tablet was taken three times a day for travelers' diarrhea. The following includes adverse reactions regardless of causal relationship to drug exposure:

TABLE 29

All Adverse Events With an Incidence ≥2% Among Patients Receiving XIFAXAN Tablets, 600 mg/day, in Placebo-Controlled Studies

| | Number (%) of Patients | |
|---|---|---|
| MedDRA Preferred Term | XIFAXAN Tablets, 600 mg/day (N = 320) | Placebo N = 228 |
| Flatulence | 36 (11.3%) | 45 (19.7%) |
| Headache | 31 (9.7%) | 21 (9.2%) |
| Abdominal Pain NOS | 23 (7.2%) | 23 (10.1%) |
| Rectal Tenesmus | 23 (7.2%) | 20 (8.8%) |
| Defacation Urgency | 19 (5.9%) | 21 (9.2%) |
| Nausea | 17 (5.3%) | 19 (8.3%) |
| Constipation | 12 (3.8%) | 8 (3.5%) |
| Pyrexia | 10 (3.1%) | 10 (4.4%) |
| Vomiting NOS | 7 (2.2%) | 4 (1.8%) |

Blood and Lymphatic System Disorders: Lymphocytosis, monocytosis, neutropenia

Ear and Labyrinth Disorders: Ear pain, motion sickness, tinnitus

Gastrointestinal Disorders: Abdominal distension, diarrhea NOS, dry throat, fecal abnormality NOS, gingival disorder NOS, inguinal hernia NOS, dry lips, stomach discomfort General Disorders and Administration Site Conditions: Chest pain, fatigue, malaise, pain NOS, weakness Infections and Infestations: Dysentery NOS, respiratory tract infection NOS, upper respiratory tract infection NOS Injury and Poisoning: Sunburn Investigations: Aspartate aminotransferase increased, blood in stool, blood in urine, weight decreased Metabolic and Nutritional Disorders: Anorexia, dehydration Musculoskeletal, Connective Tissue, and Bone Disorders: Arthralgia, muscle spasms, myalgia, neck pain Nervous System Disorders: Abnormal dreams, dizziness, migraine NOS, syncope, loss of taste Psychiatric Disorders: Insomnia Renal and Urinary Disorders: Choluria, dysuria, hematuria, polyuria, proteinuria, urinary frequency Respiratory, Thoracic, and Mediastinal Disorders: Dyspnea NOS, nasal passage irritation, nasopharyngitis, pharyngitis, pharyngolaryngeal pain, rhinitis NOS, rhinorrhea Skin and Subcutaneous Tissue Disorders: Clamminess, rash NOS, sweating increased; and Vascular Disorders: Hot flashes.

Hepatic Encephalopathy

The data described below reflect exposure to rifaximin 550 mg in 348 patients, including 265 exposed for 6 months and 202 exposed for more than a year (mean exposure was 364 days). The safety of rifaximin 550 mg taken two times a day for reducing the risk of overt hepatic encephalopathy recurrence in adult patients was evaluated in a 6-month placebo-controlled clinical trial (n=140) and in a long term follow-up study (n=280). The population studied had a mean age of 56.26 (range: 21-82) years; approximately 20% of the patients were ≥65 years old, 61% were male, 86% were White, and 4% were Black. Ninety-one percent of patients in the trial were taking lactulose concomitantly. All adverse reactions that occurred at an incidence ≥5% and at a higher incidence in rifaximin 550 mg-treated subjects than in the placebo group in thee 6-month trial are provided in Table 27. (These include adverse events that may be attributable to the underlying disease.)

TABLE 30

Adverse Events Occurring in ≥5% of Patients Receiving XIFAXAN and at a Higher Incidence Than Placebo
dverse Events Occuring in ≥5% of Patients Receiving XIFAXAN and at a Higher Incidence Than Placebo

| MedDRA Preferred Term | Number (%) of Patients | |
|---|---|---|
| | XIFAXAN Tablets 550 mg BID N = 140 | Placebo N = 159 |
| Edema peripheral | 21 (15.0%) | 13 (8.2%) |
| Nausea | 20 (14.3%) | 12 (13.2%) |
| Dizziness | 18 (12.9%) | 13 (8.2%) |
| Fatigue | 17 (12.1%) | 18 (11.3%) |
| Ascites | 16 (11.4%) | 15 (9.4%) |
| Muscle spasms | 13 (9.3%) | 11 (6.9%) |
| Pruritus | 13 (9.3%) | 10 (6.3%) |
| Abdominal pain | 12 (8.6%) | 13 (8.2%) |
| Abdominal distension | 11 (7.9%) | 12 (7.5%) |
| Anemia | 11 (7.9%) | 6 (3.8%) |
| Cough | 10 (7.1%) | 11 (6.9%) |
| Depression | 10 (7.1%) | 8 (5.0%) |
| Insomnia | 10 (7.1%) | 11 (6.9%) |
| Nasopharyngitis | 10 (7.1%) | 10 (6.3%) |
| Abdominal pain upper | 9 (6.4%) | 8 (5.0%) |
| Arthralgia | 9 (6.4%) | 4 (2.5%) |
| Back pain | 9 (6.4%) | 10 (6.3%) |
| Constipation | 9 (6.4%) | 10 (6.3%) |
| Dyspnea | 9 (6.4%) | 7 (4.4%) |
| Pyrexia | 9 (6.4%) | 5 (3.1%) |
| Rash | 7 (5.0%) | 6 (3.8%) |

The following adverse reactions, presented by body system, have also been reported in the placebo-controlled clinical trial in greater than 2% but less than 5% of patients taking rifaximin 550 mg taken orally two times a day for hepatic encephalopathy. The following includes adverse events occurring at a greater incidence than placebo, regardless of causal relationship to drug exposure.

Ear and Labyrinth Disorders: Vertigo;

Gastrointestinal Disorders: Abdominal pain lower, abdominal tenderness, dry mouth, esophageal variceal bleed, stomach discomfort.

General Disorders and Administration Site Conditions: Chest pain, generalized edema, influenza like illness, pain NOS Infections and Infestations: Cellulitis, pneumonia, rhinitis, upper respiratory tract infection NOS Injury, Poisoning and Procedural Complications: Contusion, fall, procedural pain Investigations: Weight increased Metabolic and Nutritional Disorders: Anorexia, dehydration, hyperglycemia, hyperkalemia, hypoglycemia, hyponatremia Musculoskeletal, Connective Tissue, and Bone Disorders: Myalgia, pain in extremity Nervous System Disorders: Amnesia, disturbance in attention, hypoathesia, memory impairment, tremor Psychiatric Disorders: Confusional state Respiratory, Thoracic, and Mediastinal Disorders: Epistaxis; and Vascular Disorders: Hypotension.

The following adverse reactions have been identified during post approval use of rifaximin. Because these reactions are reported voluntarily from a population of unknown size, estimates of frequency cannot be made. These reactions have been chosen for inclusion due to either their seriousness, frequency of reporting or causal connection to rifaximin.

Infections and Infestations

Cases of *C. difficile*-associated colitis have been reported.

Hypersensitivity reactions, including exfoliative dermatitis, rash, angioneurotic edema (swelling of face and tongue and difficulty swallowing), urticaria, flushing, pruritus and anaphylaxis have been reported. These events occurred as early as within 15 minutes of drug administration.

In vitro studies have shown that rifaximin did not inhibit cytochrome P450 isoenzymes 1A2, 2A6, 2B6, 2C9, 2C19, 2D6, 2E1 and CYP3A4 at concentrations ranging from 2 to 200 ng/mL. Rifaximin is not expected to inhibit these enzymes in clinical use.

An in vitro study has suggested that rifaximin induces CYP3A4. However, in patients with normal liver function, rifaximin at the recommended dosing regimen is not expected to induce CYP3A4. It is unknown whether rifaximin can have a significant effect on the pharmacokinetics of concomitant CYP3A4 substrates in patients with reduced liver function who have elevated rifaximin concentrations.

An in vitro study suggested that rifaximin is a substrate of P-glycoprotein. It is unknown whether concomitant drugs that inhibit P-glycoprotein can increase the systemic exposure of rifaximin.

Rifaximin was teratogenic in rats at doses of 150 to 300 mg/kg (approximately 2.5 to 5 times the clinical dose for travelers' diarrhea [600 mg/day], and approximately 1.3 to 2.6 times the clinical dose for hepatic encephalopathy [1100 mg/day], adjusted for body surface area). Rifaximin was teratogenic in rabbits at doses of 62.5 to 1000 mg/kg (approximately 2 to 33 times the clinical dose for travelers' diarrhea [600 mg/day], and approximately 1.1 to 18 times the clinical dose for hepatic encephalopathy [1100 mg/day], adjusted for body surface area). These effects include cleft palate, agnatha, jaw shortening, hemorrhage, eye partially open, small eyes, brachygnathia, incomplete ossification, and increased thoracolumbar vertebrae.

Reproduction studies have been performed in rats at doses up to 2.5 to 5.0 times (adjusted for body surface area) the human dose, and in rabbits at doses up to 2.0 to 33.0 times (adjusted for body surface area) the human dose and have revealed no evidence of impaired fertility or harm to the fetus due to rifaximin.

Two studies evaluated the pharmacokinetics of rifaximin in patients with hepatic impairment. In the first study mMean (SD) peak rifaximin plasma concentrations of 13.5 (14.8) ng/mL were detected in hepatic encephalopathy patients 3 hours after administration of the first dose of administered rifaximin 800 mg three times daily for 7 days; less than 0.1% of the administered dose was recovered in urine after 7 days. Because of the limited systemic absorption of rifaximin, no specific dosing adjustments are recommended for patients with hepatic insufficiency. In the second study, patients were administered rifaximin 550 mg two times a day. Mean (SD) rifaximin steady-state systemic exposure values (Cmax) in those with hepatic impairment grades of Child-Pugh A and Child-Pugh B were 19.5 (11.4) ng/mL and 25.1 (12.6) ng·h/mL (approximately 5.7- and 7.4-fold higher, respectively, than steady-state Cmax values observed in healthy individuals). This increase in systemic exposure to rifaximin in patients with hepatic impairment does not require a dosing adjustment with rifaximin due to its gastrointestinal local action and low systemic bioavailability.

Exemplary dosages of contain rifaximin, a non-aminoglycoside semi-synthetic, nonsystemic antibiotic derived from rifamycin SV. Rifaximin is a structural analog of rifampin. The chemical name for rifaximin is: (2S,16Z,18E,20S,21S,22R,23R,24R,25S,26S,27S,28E)-5,6,21,23,25-pentahydroxy-27-methoxy-2,4,11,16,20,22,24,26-octamethyl-2,7-(epoxypentadeca-[1,11,13]trienimino)benzofuro[4,5-e]pyrido[1,2-á]-benzimidazole-1,15(2H)-dione,25-acetate. The empirical formula is $C_{43}H_{51}N_3O_{11}$ and its molecular weight is 785.9.

Exemplary rifaximin tablets for oral administration are film-coated and contain 200 mg or 550 mg of rifaximin. Each tablet contains colloidal silicon dioxide, disodium edetate, glycerol palmitostearate, hypromellose, microcrystalline cellulose, propylene glycol, red iron oxide, sodium starch glycolate, talc, and titanium dioxide.

The dose-response relationship for rifaximin efficacy in reducing the severity of hepatic encephalopathy (HE) was established in a double-blind dose-ranging study (600, 1200, or 2400 mg total daily dose for 7 days) in patients with Grade 1, 2, or 3 HE, improvements from baseline were observed in all groups, as measured by an index measuring multiple HE symptoms; mean changes (improvements) in symptom index scores were −0.064, −0.103, and −0.107 in groups receiving total daily doses of 600 mg, 1200 mg, and 2400 mg, respectively.

The mean plasma pharmacokinetic parameters of rifaximin in 14 healthy subjects after a single oral 400 mg dose given as 2×200 mg doses and a single 550 mg dose in 12 healthy subjects under fed and fasting conditions are summarized in Table 31.

Mean rifaximin pharmacokinetic parameters were Cmax 4.3±2.8 ng/mL and AUCt 19.5±16.5 ng·h/mL with a median Tmax of 1.25 hours.

Travelers' Diarrhea

Systemic absorption of rifaximin (200 mg three times daily) was evaluated in 13 subjects challenged with shigellosis on Days 1 and 3 of a three-day course of treatment. Rifaximin plasma concentrations and exposures were low and variable. There was no evidence of accumulation of rifaximin following repeated administration for 3 days (9 doses). Peak plasma rifaximin concentrations after 3 and 9 consecutive doses ranged from 0.81 to 3.4 ng/mL on Day 1 and 0.68 to 2.26 ng/mL on Day 3. Similarly, $AUC_{0-last}$ estimates were 6.95±5.15 ng·h/mL on Day 1 and 7.83±4.94 ng·h/mL on Day 3. Rifaximin is not suitable for treating systemic bacterial infections because of limited systemic exposure after oral administration.

Hepatic Encephalopathy

After a single dose and multiple doses of rifaximin 550 mg in healthy subjects, the mean time to reach peak plasma concentrations was about an hour. The pharmacokinetic (PK) parameters were highly variable and the accumulation ratio based on AUC was 1.37.

The pharmacokinetics of patients with hepatic impairment (hepatic impairment grades of Child-Pugh A and Child-Pugh B) taking rifaximin 550 mg two times a day were evaluated in an open-label rifaximin study. Rifaximin exposure values (AUCτ) in subjects with Child-Pugh score A and B (118 and 161 ng*h/mL, respectively) were approximately 9.6- and 13.1-fold higher than that observed in healthy subjects following two times a day oral doses of 550 mg (12.3 ng*h/mL), respectively. Intersubject variabilites in the pharmacokinetics of healthy subjects were generally similar to those measured in subjects with hepatic impairment.

TABLE 31

Effect of Food on the Mean ± S.D. Pharmacokinetic Parameters
Single 400 mg Dose of Rifaximin (N = 14)
Table 41 Effect of Food on the Mean ± S.D. Pharmacokinetic Parameters

| Parameter | Single 400 mg Dose of Rifaximin (N-14) | | Single 550 mg Dose of Rifaximin (N = 12) | |
|---|---|---|---|---|
| | Fasting | Fed | Fasting | Fed |
| $C_{max}$ (ng/mL) | 3.80 ± 1.32 | 9.63 ± 5.93 | 4.04 ± 1.51 | 4.76 ± 4.25 |
| $T_{max}$ (h) | 1.21 ± 0.47 | 1.90 ± 1.52 | 0.75 (0.50-2.05)* | 1.50 (0.50-4.08)* |
| Half-Life (h) | 5.85 ± 4.34 | 5.95 ± 1.88 | 1.83 ± 1.38 | 4.84 ± 1.34 |
| AUC (ng · h/mL) | 18.35 ± 9.48 | 34.70 ± 9.23 | 11.1 ± 4.15 | 22.5 ± 12.0 |

Rifaximin can be administered with or without food. Because systemic absorption of rifaximin was low minimal in both the fasting state and when administered within 30 minutes of a high-fat breakfast, rifaximin can be administered with or without food.

14C-Rifaximin was administered as a single dose to 4 healthy male subjects. The mean overall recovery of radioactivity in the urine and feces of 3 subjects during the 168 hours after administration was 96.94±5.64% of the dose. Radioactivity was excreted almost exclusively in the feces (96.62±5.67% of the dose), with only a small proportion of the dose (mean 0.32% of the dose) excreted in urine. Analysis of fecal extracts indicated that rifaximin was being excreted as unchanged drug. The amount of radioactivity in urine (<0.4% of the dose) suggests that rifaximin is poorly absorbed from the gastrointestinal tract and is almost exclusively and completely excreted in feces as unchanged drug.

Rifaximin can be administered with or without food.

Animal pharmacokinetic studies have demonstrated that 80% to 90% of orally administered rifaximin is concentrated in the gut with less than 0.2% in the liver and kidney, and less than 0.01% in other tissues. In adults with infectious diarrhea treated with rifaximin 800 mg daily for three days, concentrations of rifaximin in stools averaged ~8000 μg/g the day after treatment ended.

In a mass balance study, after administration of 400 mg $^{14}$C-rifaximin orally to healthy volunteers, of the 96.94% total recovery, 96.62% of the administered radioactivity was recovered in feces almost exclusively as the unchanged drug and 0.32% was recovered in urine mostly as metabolites with 0.03% as the unchanged drug. Rifaximin accounted for 18% of radioactivity in plasma. This suggests that the absorbed rifaximin undergoes metabolism with minimal renal excretion of the unchanged drug. The enzymes responsible for metabolizing rifaximin are unknown.

In a separate study, rifaximin was detected in the bile after cholecystectomy in patients with intact gastrointestinal mucosa, suggesting biliary excretion of rifaximin.

Hepatic Impairment

The systemic exposure of rifaximin was markedly elevated in patients with hepatic impairment compared to healthy subjects. The mean AUC in patients with Child-Pugh Class C hepatic impairment was 2-fold higher than in patients with Child-Pugh Class A hepatic impairment (see Table 28).

In vitro drug interaction studies have shown that rifaximin, at concentrations ranging from 2 to 200 ng/mL, did not inhibit human hepatic cytochrome P450 isoenzymes 1A2, 2A6, 2B6, 2C9, 2C19, 2D6, 2E1, and 3A4. In an in vitro hepatocyte induction model, rifaximin was shown to induce cytochrome P450 3A4 (CYP3A4), an isoenzyme which rifampin is known to induce. Two clinical drug-drug interaction studies using midazolam and an oral contraceptive containing ethinyl estradiol and norgestimate demonstrated that rifaximin (200 mg TID for 3 days) did not alter the pharmacokinetics of these drugs, and rifaximin 550 mg TID for 7 or 14 days resulted in only slightly reduced exposure to midazolam following a single oral midazolam dose.

In an in vitro study, rifaximin was shown to induce CYP3A4 at the concentration of 0.2 µM.

An in vitro study suggests that rifaximin is a substrate of P-glycoprotein. In the presence of P-glycoprotein inhibitor verapamil, the efflux ratio of rifaximin was reduced greater than 50% in vitro. The effect of P-glycoprotein inhibition on rifaximin was not evaluated in vivo.

The inhibitory effect of rifaximin on P-gp transporter was observed in an in vitro study. The effect of rifaximin on P-gp transporter was not evaluated in vivo.

The effect of rifaximin 200 mg administered orally every 8 hours for 3 days and for 7 days on the pharmacokinetics of a single dose of either midazolam 2 mg intravenous or midazolam 6 mg orally was evaluated in healthy subjects. No significant difference was observed in the metrics of systemic exposure or elimination of intravenous or oral midazolam or its major metabolite, 1'-hydroxymidazolam, between midazolam alone or together with rifaximin. Therefore, rifaximin was not shown to significantly affect intestinal or hepatic CYP3A4 activity for the 200 mg three times a day dosing regimen.

After rifaximin 550 mg was administered three times a day for 7 days and 14 days to healthy subjects, the mean AUC of single midazolam 2 mg orally was 3.8% and 8.8% lower, respectively, than when midazolam was administered alone. The mean $C_{max}$ of midazolam was also decreased by 4-5% when rifaximin was administered for 7-14 days prior to midazolam administration. This degree of interaction is not considered clinically meaningful.

The effect of rifaximin on CYP3A4 in patients with impaired liver function who have elevated systemic exposure is not known.

Oral Contraceptives Containing 0.07 mg Ethinyl Estradiol and 0.5 mg Norgestimate The oral contraceptive study utilized an open-label, crossover design in 28 healthy female subjects to determine if rifaximin 200 mg orally administered three times a day for 3 days (the dosing regimen for travelers' diarrhea) altered the pharmacokinetics of a single dose of an oral contraceptive containing 0.07 mg ethinyl estradiol and 0.5 mg norgestimate. Results showed that the pharmacokinetics of single doses of ethinyl estradiol and norgestimate were not altered by rifaximin.

In vitro study data suggest that rifaximin is a substrate for P-glycoprotein. Rifaximin is a weak inhibitor of P-gp; at concentrations (50 µM) significantly higher than those anticipated in plasma following oral dose administration, rifaximin only partially inhibited transport of a model P-gp substrate. Therefore, no clinically significant interactions with other drugs affected by P-glycoprotein are anticipated.

Rifaximin is excreted primarily in the feces. After oral administration of 400 mg 14C398 rifaximin to healthy volunteers, approximately 97% of the dose was recovered in feces, almost entirely as unchanged drug, and 0.32% was recovered in the urine.

Rifaximin is a non-aminoglycoside semi-synthetic antibiotic derived from rifamycin SV; it is a structural analog of rifampin. The mechanism of action of rifaximin depends on the inhibition of DNA-dependent RNA polymerase of the target microorganisms, leading to the suppression of initiation of chain formation in RNA synthesis.

The lower rate of eradication of fecal pathogens in patients treated with rifaximin compared with fluoroquinolones and aminoglycosides and lack of alteration of gut flora indicate a unique mechanism of action. Rifaximin may alter virulence factors of enteric bacterial pathogens without killing them, as has been seen with subtherapeutic levels of drugs and colonization fimbriae of enterotoxigenic *E. coli*. Rifaximin caused morphological alterations in both susceptible and resistant bacterial strains at concentrations as low as 1/32 of the MIC.1Rifaximin reduced the viability and virulence of resistant bacteria, suggesting that if in vivo pathogens are exposed to sub-MICs of the drug, not only are their physiological functions compromised, but gene virulence and antibiotic resistance are not fully expressed.

Rifaximin has in vitro antimicrobial activity against numerous Gram-positive and Gram-negative bacteria, such as *Escherichia coli*. Animal and human studies demonstrate negligible systemic rifaximin absorption (<1%) after oral administration. The negligible systemic absorption of rifaximin from the gastrointestinal tract minimizes the potential adverse events associated with systemically absorbed antibiotics. Rifaximin is delivered at high concentrations to the gastrointestinal tract, which is the therapeutic site of action.

Rifaximin acts by binding to the beta-subunit of bacterial DNA-dependent RNA polymerase resulting in inhibition of bacterial RNA synthesis.

*Escherichia coli* has been shown to develop resistance to rifaximin in vitro. However, the clinical significance of such an effect has not been studied.

Rifaximin is a structural analog of rifampin. Organisms with high rifaximin minimum inhibitory concentration (MIC) values also have elevated MIC values against rifampin. Cross-resistance between rifaximin and other classes of antimicrobials has not been studied.

Rifaximin has been shown to be active against the following pathogen in clinical studies of infectious diarrhea as described in herein.

For HE, rifaximin is thought to have an effect on the gastrointestinal flora.

In vitro susceptibility testing was performed according to the National Committee for Clinical Laboratory Standards (NCCLS) agar dilution method M7-A612. However, the correlation between susceptibility testing and clinical outcome has not been determined.

*Escherichia coli* has been shown to develop resistance to rifaximin in vitro. However, the clinical significance of such an effect has not been studied. Rifaximin is a structural analog of rifampin. Organisms with high rifaximin minimum inhibitory concentration (MIC) values also have elevated MIC values against rifampin. Cross resistance between rifaximin and other classes of antimicrobials has not been studied.

Malignant schwannomas in the heart were significantly increased in male Crl:CD® (SD) rats that received rifaximin by oral gavage for two years at 150 to 250 mg/kg/day (doses equivalent to 2.4 to 4 times the recommended dose of 200 mg three times daily for travelers' diarrhea, and equivalent to 1.3 to 2.2 times the recommended dose of 550 mg twice daily for hepatic encephalopathy, based on relative body surface area comparisons). There was no increase in tumors in Tg.rasH2 mice dosed orally with rifaximin for 26 weeks at 150 to 2000 mg/kg/day (doses equivalent to 1.2 to 16 times the recommended daily dose for travelers' diarrhea and equivalent to 0.7 to 9 times the recommended daily dose for hepatic encephalopathy, based on relative body surface area comparisons).

The carcinogenic potential of rifaximin was examined in a 2 year study with CD rats. Daily oral administration of at dose levels ranging from 20, 50, to 250 mg/kg/day produced no evidence of a carcinogenic effect.

Similarly, in a study with Tg.rasH2 mice daily oral administration by gavage with rifaximin at doses up to 1500 mg/kg/day (males) and 2000 mg/kg/day (females) for 26-weeks did not increase the incidence of tumors when compared to vehicle control.

Rifaximin was not genotoxic in the bacterial reverse mutation assay, chromosomal aberration assay, rat bone marrow micronucleus assay, rat hepatocyte unscheduled DNA synthesis assay, or the CHO/HGPRT mutation assay. There was no effect on fertility in male or female rats following the administration of rifaximin at doses up to 300 mg/kg (approximately 5 times the clinical dose of 600 mg/day, and approximately 2.6 times the clinical dose of 1100 mg/day, adjusted for body surface area).

Results from multiple-dose oral toxicity studies in rats, rabbits, and dogs showed negligible toxic effects of rifaximin at doses ranging from 6 to 68 times the clinical dose for travelers' diarrhea (600 mg/day) for durations of up to 39 weeks.

In a 26-week study with Tg.rasH2 mice orally administered rifaximin at doses up to 1500 mg/kg/day (males) and 2000 mg/kg/day (females) 2/25 female mice at 2000 mg/kg day presented ruffled fur and hunched appearance in low incidence that did not reach statistical significance.

Oral administration of rifaximin for 3-6 months produced hepatic proliferation of connective tissue in rats (50 mg/kg/day) and fatty degeneration of liver in dogs (100 mg/kg/day). However, plasma drug levels were not measured in these studies. Subsequently, rifaximin was studied at doses as high as 300 mg/kg/day in rats for 6 months and 1000 mg/kg/day in dogs for 9 months, and no signs of hepatotoxicity were observed. The maximum plasma $AUC_{0-8\ hr}$ values from the 6 month rat and 9 month dog toxicity studies (range: 42-127 ng·h/mL) was lower than the maximum plasma $AUC_{0-8\ hr}$ values in cirrhotic patients (range: 19-306 ng*h/mL).

The efficacy of rifaximin given as 200 mg orally taken three times a day for 3 days was evaluated in 2 randomized, multi-center, double-blind, placebo-controlled studies in adult subjects with travelers' diarrhea. One study was conducted at clinical sites in Mexico, Guatemala, and Kenya (Study 1). The other study was conducted in Mexico, Guatemala, Peru, and India (Study 2). Stool specimens were collected before treatment and 1 to 3 days following the end of treatment to identify enteric pathogens. The predominant pathogen in both studies was *Escherichia coli*.

The clinical efficacy of rifaximin was assessed by the time to return to normal, formed stools and resolution of symptoms. The primary efficacy endpoint was time to last unformed stool (TLUS) which was defined as the time to the last unformed stool passed, after which clinical cure was declared. Table 32 displays the median TLUS and the number of patients who achieved clinical cure for the intent to treat (ITT) population of Study 1. The duration of diarrhea was significantly shorter in patients treated with rifaximin than in the placebo group. More patients treated with rifaximin were classified as clinical cures than were those in the placebo group.

TABLE 32

Clinical Response in Study 1 (ITT population)

|  | XIFAXAN (n = 125) | Placebo (n = 129) | Estimate (97.5% CI) | P-Value |
|---|---|---|---|---|
| Median TLUS (hours) | 32.5 | 58.6 | 1.78$^a$ (1.26, 2.50) | 0.0002 |
| Clinical cure, n (%) | 99 (79.2) | 78 (60.5) | 18.7$^b$ (5.3, 32.1) | 0.001 |

$^a$Hazard Ratio
$^b$Difference in rates

Microbiological eradication (defined as the absence of a baseline pathogen in culture of stool after 72 hours of therapy) rates for Study 1 are presented in Table 30 for patients with any pathogen at baseline and for the subset of patients with *Escherichia coli* at baseline. *Escherichia coli* was the only pathogen with sufficient numbers to allow comparisons between treatment groups.

Even though rifaximin had microbiologic activity similar to placebo, it demonstrated a clinically significant reduction in duration of diarrhea and a higher clinical cure rate than placebo. Therefore, patients should be managed based on clinical response to therapy rather than microbiologic response.

TABLE 33

Microbiologic Eradication Rates in Study 1
Subjects with a Baseline Pathogen

|  | Rifaximin | Placebo |
|---|---|---|
| Overall | 48/70 (68.6) | 41/61 (67.2) |
| E. coli | 38/53 (71.7) | 40/54 (74.1) |

The results of Study 2 supported the results presented for Study 1. In addition, this study also provided evidence that subjects treated with rifaximin with fever and/or blood in the stool at baseline had prolonged TLUS. These subjects had lower clinical cure rates than those without fever or blood in the stool at baseline. Many of the patients with fever and/or blood in the stool (dysentery-like diarrheal syndromes) had invasive pathogens, primarily *Campylobacter jejuni*, isolated in the baseline stool.

Also in this study, the majority of the subjects treated with rifaximin who had *Campylobacter jejuni* isolated as a sole pathogen at baseline failed treatment and the resulting clinical cure rate for these patients was 23.5% (4/17). In addition to not being different from placebo, the microbiologic eradication rates for subjects with *Campylobacter*

*jejuni* isolated at baseline were much lower than the eradication rates seen for *Escherichia coli*.

In an unrelated open-label, pharmacokinetic study of oral rifaximin 200 mg taken every 8 hours for 3 days, 15 adult subjects were challenged with *Shigella flexneri* 2a, of whom 13 developed diarrhea or dysentery and were treated with rifaximin. Although this open-label challenge trial was not adequate to assess the effectiveness of rifaximin in the treatment of shigellosis, the following observations were noted: eight subjects received rescue treatment with ciprofloxacin either because of lack of response to rifaximin treatment within 24 hours (2), or because they developed severe dysentery (5), or because of recurrence of *Shigella flexneri* in the stool (1); five of the 13 subjects received ciprofloxacin although they did not have evidence of severe disease or relapse.

The efficacy of rifaximin 550 mg taken orally two times a day was evaluated in a randomized, placebo-controlled, double-blind, multi-center 6-month trial of adult subjects from the U.S., Canada and Russia who were defined as being in remission (Conn score of 0 or 1) from hepatic encephalopathy (HE). Eligible subjects had ≥2 episodes of HE associated with chronic liver disease in the previous 6 months.

A total of 299 subjects were randomized to receive either rifaximin (n=140) or placebo (n=159) in this study. Patients had a mean age of 56 years (range, 21-82 years), 81% <65 years of age, 61% were male and 86% White. At baseline, 67% of patients had a Conn score of 0 and 68% had an asterixis grade of 0. Patients had MELD scores of either ≤10 (27%) or 11 to 18 (64%) at baseline. No patients were enrolled with a MELD score of >25. Nine percent of the patients were Child-Pugh Class C. Lactulose was concomitantly used by 91% of the patients in each treatment arm of the study. Per the study protocol, patients were withdrawn from the study after experiencing a breakthrough HE episode. Other reasons for early study discontinuation included: adverse reactions (rifaximin 6%; placebo 4%), patient request to withdraw (rifaximin 4%; placebo 6%) and other (rifaximin 7%; placebo 5%).

The primary endpoint was the time to first breakthrough overt HE episode. A breakthrough overt HE episode was defined as a marked deterioration in neurological function and an increase of Conn score to Grade ≥2. In patients with a baseline Conn score of 0, a breakthrough overt HE episode was defined as an increase in Conn score of 1 and asterixis grade of 1.

Figure 24:
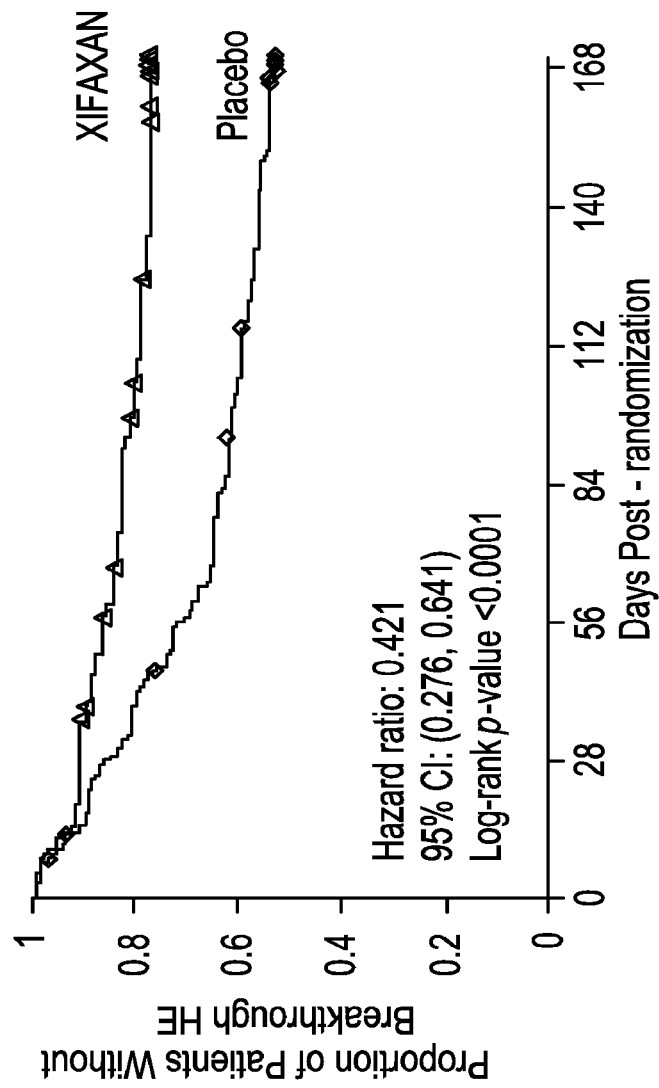
FIG. 24 depicts the Kaplan-Meier Event-Free Curves in HE Study (Time to First Breakthrough-HE Episode up to 6 Months of Treatment, Day 170) (ITT Population).

Breakthrough overt HE episodes were experienced by 31 of 140 subjects (22%) in the rifaximin group and by 73 of 159 subjects (46%) in the placebo group during the 6-month treatment period. Comparison of Kaplan-Meier estimates of event-free curves showed rifaximin significantly reduced the risk of HE breakthrough by 58% during the 6-month treatment period. Presented below in FIG. 24 is the Kaplan-Meier event-free curve for all subjects (n=299) in the study.

When the results were evaluated by the following demographic and baseline characteristics, the treatment effect of rifaximin 550 mg in reducing the risk of breakthrough overt HE recurrence was consistent for: sex, baseline Conn score, duration of current remission and diabetes. The differences in treatment effect could not be assessed in the following subpopulations due to small sample size: non-White (n=42), baseline MELD >19 (n=26), Child-Pugh C (n=31), and those without concomitant lactulose use (n=26).

Figure 25:
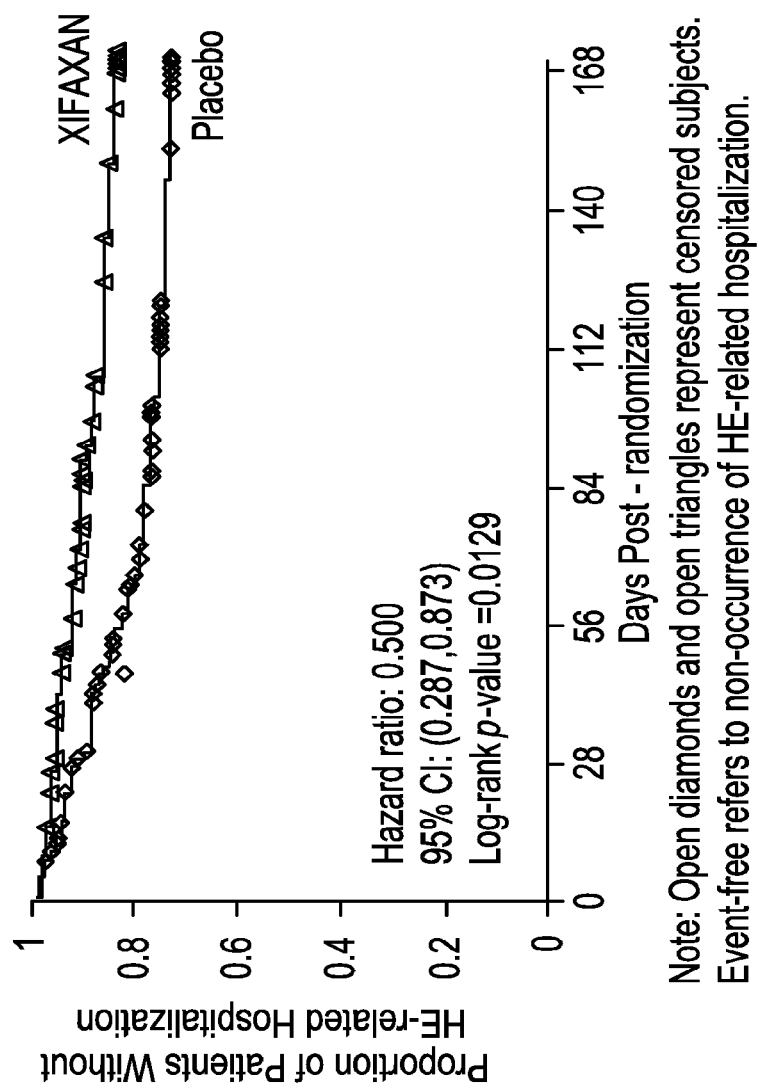
FIG. 25 depicts Kaplan-Meier Event-Free Curves in Pivotal HE Study (Time to First HE-Related Hospitalization in HE Study up to 6 Months of Treatment, Day 170) (ITT Population).

FIG. 25 shows hazard ratios for the risk of experiencing breakthrough overt HE (rifaximin group divided by placebo group) for each subgroup, 95% confidence intervals as determined by the Cox proportional hazards model. P-values for differences between the rifaximin and placebo groups were determined by log rank test.

Figure 26:
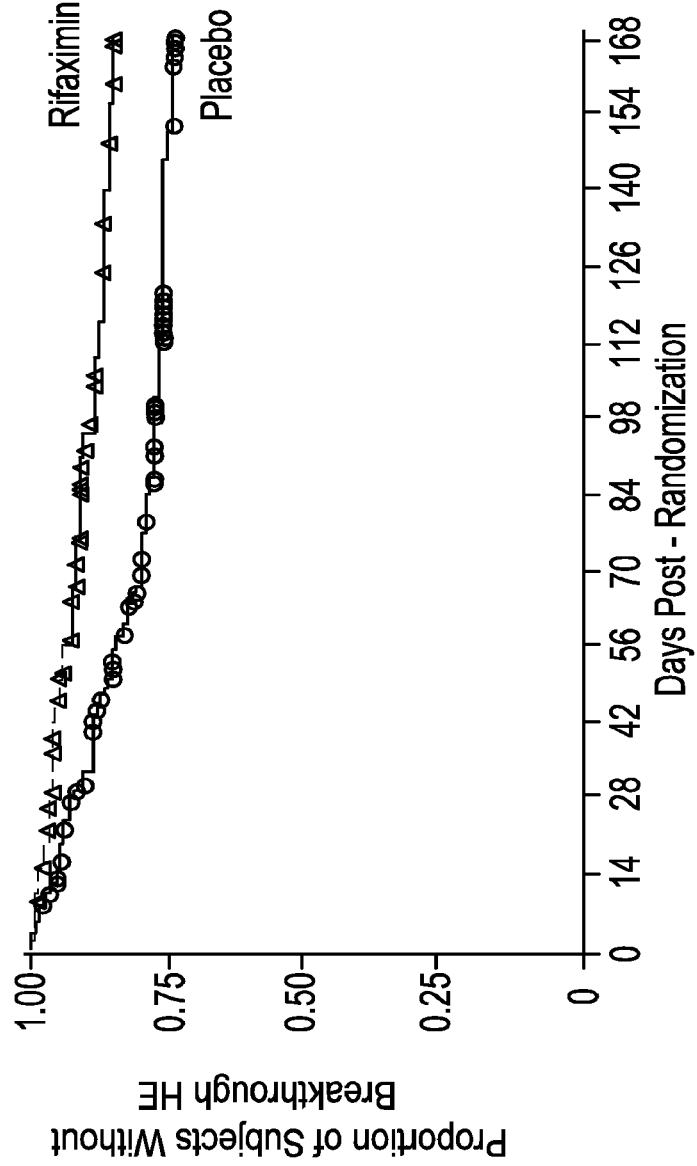
FIG. 26 is a line graph showing the time to First Breakthrough HE Episode.
Figure 27:
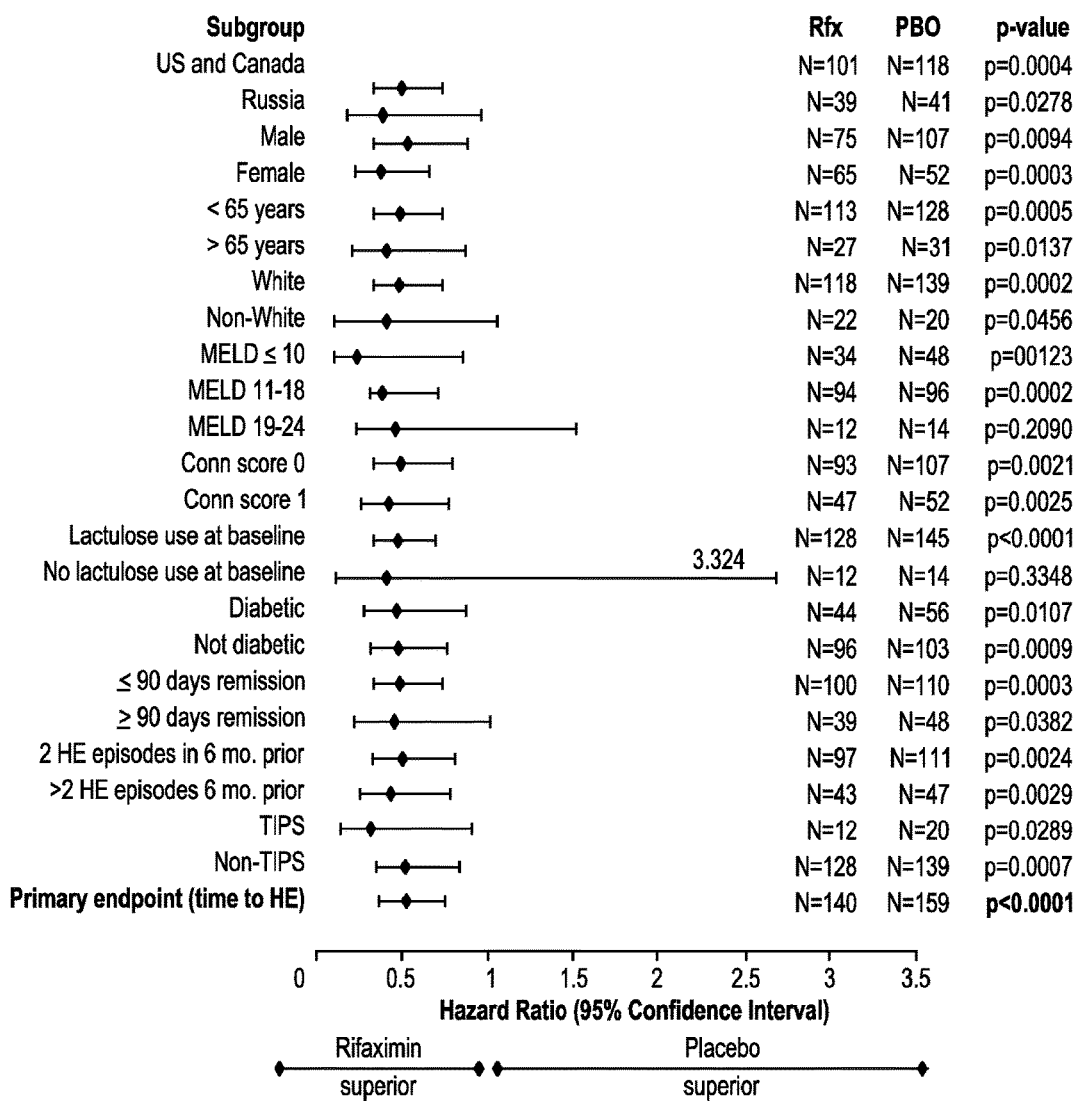
FIG. 27 is a chart showing hazard ratios for the risk of experiencing breakthrough overt HE (rifaximin group divided by placebo group) for each subgroup.

HE-related hospitalizations were reported for 19 of 140 subjects (14%) and 36 of 159 subjects (23%) in the rifaximin and placebo groups, respectively. Rifaximin had a significant reduction of risk against HE-related hospitalization during the 6-month treatment period; hazard ratio in the rifaximin group relative to placebo was 0.500 (95% CI: 0.287 to 0.873) (p=0.0129). Subjects in the rifaximin group had a 50% reduction in the risk of hospitalization due to HE during the 6-month treatment period when compared with placebo. See FIG. 26: Time to First HE-Related Hospitalization in HE Study (up to 6 Months of Treatment, Day 170) (ITT Population).

HE-related hospitalizations (hospitalizations directly resulting from HE, or hospitalizations complicated by HE) were reported for 19 of 140 subjects (14%) and 36 of 159 subjects (23%) in the rifaximin and placebo groups respectively. rifaximin had a significant reduction of risk against HE-related hospitalization during the 6-month treatment period; hazard ratio in the rifaximin group relative to placebo was 0.500 (95% CI: 0.287 to 0.873) (p=0.0129). Subjects in the rifaximin group had a 50% reduction in the risk of hospitalization due to HE during the 6-month treatment period when compared with placebo. See FIG. 26: Time to First HE-Related Hospitalization in HE Study (up to 6 Months of Treatment, Day 170) (ITT Population).

Comparison of Kaplan-Meier estimates of event-free curves showed rifaximin significantly reduced the risk of HE-related hospitalizations by 50% during the 6-month treatment period. Comparison of Kaplan-Meier estimates of event-free curves is shown in FIG. 25.

Methods for dilution antimicrobial susceptibility tests for bacteria that grow aerobically. National Committee for Clinical Laboratory Standards, Sixth Edition, Wayne P A. *Approved Standard NCCLS Document M7-A6* Jan. 2003; 23 (2).

Highly significant protective effects of rifaximin were observed with respect to time to any increase from baseline in Conn score and time to any increase from baseline in asterixis grade when analyzed independently; hazard ratio in the rifaximin group relative to placebo was 0.463 (95% CI: 0.312 to 0.685) (p<0.0001) for the risk of experiencing an increase in Conn score (ie, worsening in mental status) and 0.646 (95% CI: 0.414 to 1.008) (p=0.0523) for the risk of experiencing an increase in asterixis grade (ie, worsening in neuromotor functioning) during the 6-month treatment period.

Because lactulose was the most frequently used concomitant medicine, an analysis was undertaken to analyze lactulose use at baseline and during the study to ensure that rifaximin treatment effect was not modified. At baseline and during the trial, lactulose use between the rifaximin and control groups was no different. Thus, results of the study showing efficacy of rifaximin were not influenced by the use of lactulose.

Figure 28:
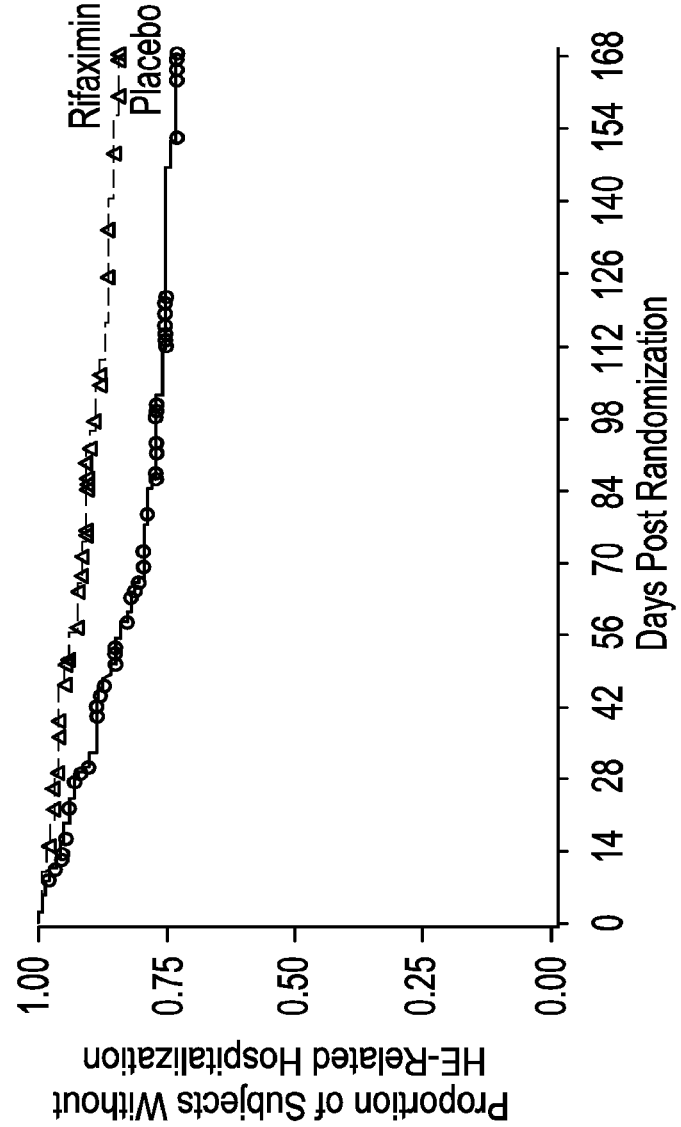
FIG. 28 is a line graph illustrating a time to First HE-Related Hospitalization.
Figure 30:
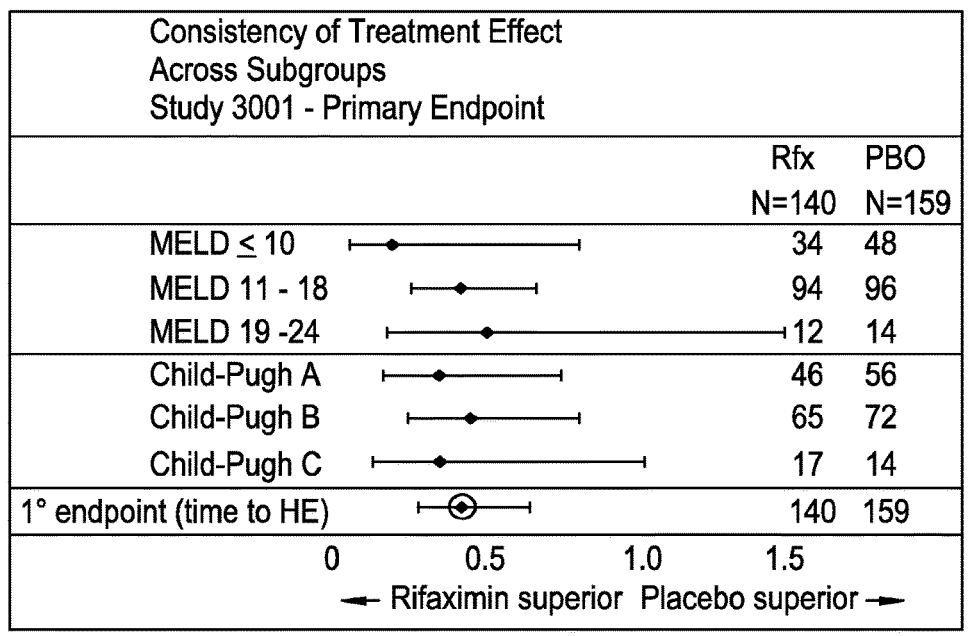
FIG. 30 is a chart illustrating that there was a consistency of treatment affect across various subgroups that were administered rifaximin.

In addition, patient subgroups were analyzed by MELD and Child-Pugh analyses to determine any differences between the treatment group and the rifaximin group. It was found that the positive effects of rifaximin were not limited by liver disease severity. In addition, it was also found that there was no significant interaction across subgroups. Accordingly, all these analyses demonstrated a risk reduction in favor of rifaximin. FIG. 28 illustrates that there was a consistency of treatment affect across all the various subgroups that were administered rifaximin.

*Clostridium difficile*-associated diarrhea (CDAD) has been reported with use of nearly all antibacterial agents, including rifaximin, and may range in severity from mild diarrhea to fatal colitis. Treatment with antibiotics alters the normal flora of the colon which may lead to *C. difficile*. Patients can develop watery and bloody stools (with or without stomach cramps and fever) even as late as two or more months after having taken the last dose of the antibiotic. If diarrhea occurs after therapy or does not improve or worsens during therapy, advise patients to contact a physician as soon as possible.

Patients should be informed that in patients with severe hepatic impairment (Child-Pugh C) there is an increase in systemic exposure to rifaximin.

EXAMPLES

It should be appreciated that embodiments of the invention should not be construed to be limited to the examples, which are now described; rather, the invention should be construed to include any and all applications provided herein and all equivalent variations within the skill of the ordinary artisan.

Example 1: Effects of Rifaximin on Subjects with Hepatic Insufficiency

Subjects were instructed to take one tablet of 550 mg of rifaximin by mouth 2 times per day—approximately every 12 hours. The rifaximin may be co-administered with other medications, for example, lactulose, antidepressants, anti-inflammatory, methadone, prescription and non-prescription sleep aids (e.g., Lunesta™ (eszopiclone) and Ambien® (zolpidem tartrate)), and antihistamines, diuretics, laxatives or stool softeners, neurontin (gabapentin) and lyrica (pregabalin).

Lactulose use was optional for subjects. For subjects who used lactulose, it was titrated to a dose during the 3 to 7-day observation period according to accepted medical practice.
Asterixis Grade Asterixis (flapping tremor) was determined with the subject holding both arms and forearms extended with wrists dorsiflexed and fingers open for ≥30 seconds. Asterixis was measured on a continuum of 5 grades, e.g., grades 0 and 4=no abnormal movement vs. almost continuous flapping motions, respectively as shown below:
Grade 0=No tremors;
Grade 1=Rare flapping motions;
Grade 2=Occasional, irregular flaps;
Grade 3=Frequent flaps; and
Grade 4=Almost continuous flapping motions.

Efficacy in regard to asterixis grade was measured as time to any increase from baseline in asterixis grade. Time to an increase in asterixis grade was computed as the number of days from the first dose of rifaximin to the initial occurrence of an increase from baseline in asterixis grade.
Breakthrough HE Episode Relative risk of experiencing a breakthrough HE episode (e.g., Conn score Grade ≥2, (e.g., 0 or 1 to ≥2) or a Conn and asterixis score increase of 1 grade each) for each subject in the trial taking either rifaximin or the placebo was measured. The analysis compared time to first breakthrough HE episode for rifaximin versus placebo using survival analysis methods. Time to first breakthrough HE episode was computed as the number of days from the first dose of rifaximin to the initial occurrence of breakthrough HE (e.g., Conn score Grade ≥2, or a Conn and asterixis score increase of 1 grade each).

Change in mental status was measured by the Conn score (also known as the West Haven score). The Conn score has been widely used as a measure of mental state in HE studies and is based on the criteria of Parsons-Smith as modified by Conn. The scale used in the Conn scoring system is described above.

Subjects had a Conn score of 0 or 1. An increase in the Conn score of greater than or equal to grade 2 was considered as a breakthrough HE episode.
Hepatic Encephalopathy Scoring Algorithm (HESA)

The Hepatic Encephalopathy Scoring Algorithm (HESA) is a method that uses both clinical and neuropsychological assessments to assess mental status. The Algorithm has been validated previously and has been correlated with the Conn criteria.

The CFF test is recognized as a quantitative measure of CNS dysfunction and that utilizes the correlation between cerebral processing of oscillatory visual stimuli and its subsequent impairment due to increased HE severity. The CFF test was administered, and statistically significant greater improvement in CFF results were observed in rifaximin subjects when compared with placebo ($p=0.0320$).

The Critical Flicker Frequency (CFF) was assessed for each subject at screening, baseline, visits 3 through 14 and the end of study visit using the Lafayette Flicker Fusion (Lafayette Instrument Company, Inc). Circular light pulses with a 1:1 ratio between the visual impulse and the interval were used with decreasing frequency in gradual steps of 0.5 to 0.1 Hz/second. The frequency of the white light, which is initially generated as a high-frequency pulse (50 Hz) and which gives the patient the impression of a steady light, was reduced gradually until the patient had the impression that the steady light had changed to a flicker. The patient registered this change by pressing a hand-held switch. The flicker frequencies were measured 8 times and from these data, the mean values for each patient were calculated. The process was conducted in a quiet, semi-darkened room without distracting noises and took about 10 minutes.
Critical Flicker Frequency scores The critical flicker frequency (CFF) was assessed for each subject using a specialized CFF instrument. The CFF is the frequency at which the subject observes a constant light transition to a flickering light and is measured in Hertz (Hz). CFF is an objective assessment of mental status. A CFF value of 39 Hz has been shown to be the threshold for separation between subjects who have manifest HE (e.g., Conn≥1) and those without HE symptoms (e.g., Conn=0), with a lower CFF value indicating more severe HE[43].

The CFF was measured on a continuous scale and was the mean of 8 separate fusion-to-flicker transition tests performed in rapid succession.
Ammonia Concentrations Venous blood samples (10 mL) were collected and ammonia concentrations were obtained by methods known in the art.

Time to Increase from Baseline in Either the Conn Score (Mental State Grade) or Asterixis Grade To analyze the time to a first breakthrough HE episode, survival analysis methods were used to assess the effectiveness of the rifaximin treatment on the time to increase from baseline in either the Conn score (mental state grade) or asterixis grade. Time to increase in either the Conn score or asterixis grade was computed as the number of days from the first dose of rifaximin to the initial occurrence of either an increase from baseline in Conn score or asterixis grade. The analysis of time to increase in either Conn score or asterixis grade were based on the comparison of time to event between rifaximin and placebo.

Time to First HE-Related Hospitalization

The effect of rifaximin on time to first HE-related hospitalization was determined. Time to first HE-related hospitalization was computed as the number of days from the first dose of rifaximin to the first hospitalization for an HE related event. The analysis of time to first HE-related hospitalization was based on the comparison of time to hospitalization between rifaximin and placebo.

Time to Development of Spontaneous Bacterial Peritonitis

The effect of rifaximin on time to development of spontaneous bacterial peritonitis (SBP) was determined. Time to development of SBP was computed as the number of days from the first dose of rifaximin to the time of peritoneal fluid collection that resulted in a positive test for SBP. The analysis of time to development of SBP was based on the comparison of time to event between rifaximin and placebo.

Mean Change from Baseline in Blood Ammonia Concentration and Critical Flicker Frequency Values Over Time Mean values and mean changes from baseline in blood ammonia concentration and critical flicker frequency values were collected. Analyses of blood ammonia concentrations and critical flicker frequency values were based upon quantitative values (not qualitative grades). Treatment differences for mean change from baseline in these parameters was estimated using a mixed effects model with fixed effects for time and baseline value.

Mean Daily Lactulose Consumption Over Time

A subject's daily lactulose consumption was used to compute mean daily lactulose consumption for each month. Treatment differences for mean change from baseline in mean daily lactulose consumption were estimated.

CLDQ

The CLDQ includes 29 items in the following six domains: abdominal symptoms (three items), fatigue (five items), systemic symptoms (five items), activity (three items), emotional function (eight items), and worry (five items). Summary scores for the CLDQ overall and each of the six domains were computed and summarized at baseline and Days 28, 56, 84, 112, 140 and 168 using descriptive statistics. Treatment differences for mean change in overall score and domain scores from baseline to Days 28, 56, 84, 112, 140 and 168 were collected summarized and compared between treatments.

Treatment differences for mean change from baseline to EOT were determined as the change from baseline at EOT in fatigue domain score of Chronic Liver Disease Questionnaire (CLDQ). Similarly, the mean change from baseline in blood ammonia concentration at EOT was also determined.

Assessment of Quality of Life

The SF-36, Chronic Liver Disease Questionnaire (CLDQ), and Epworth Sleepiness Scale were used to measure health related quality of life. The 29 item CLDQ questionnaire consists of the following domains: fatigue, activity, emotional function, abdominal symptoms, systemic symptoms, and worry.

Epworth Sleepiness Scale

Total scores for the Epworth Sleepiness Scale were computed and summarized at baseline and Days 28, 56, 84, 112, 140 and 168 using descriptive statistics. Treatment differences for mean change in total scores from baseline to Days 28, 56, 84, 112, 140 and 168 were summarized and compared between treatments.

FIG. 1 is a line graph showing Lactulose daily use between subjects taking placebos and subjects taking rifaximin as described above.

Figure 2:
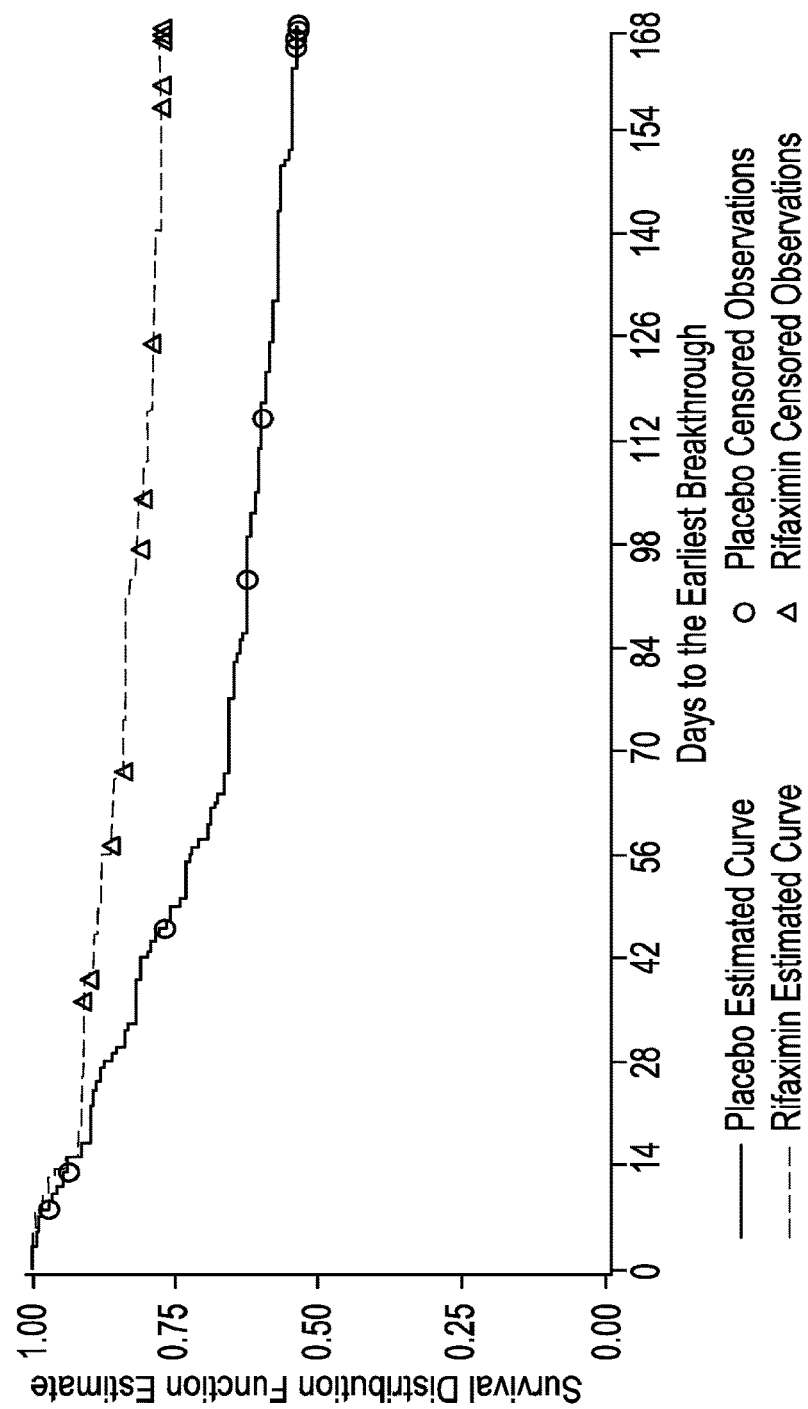
FIG. 2 is a line graph showing Kaplan Meier estimates of the distribution of time to a breakthrough HE event.

FIG. 2 is a line graph showing Kaplan Meier estimates of the distribution of time to a breakthrough HE event for the placebo group and the rifaximin group. As indicated there was an increased time to breakthrough HE events for subjects taking rifaximin in comparison to subjects taking the placebo.

Figure 3:
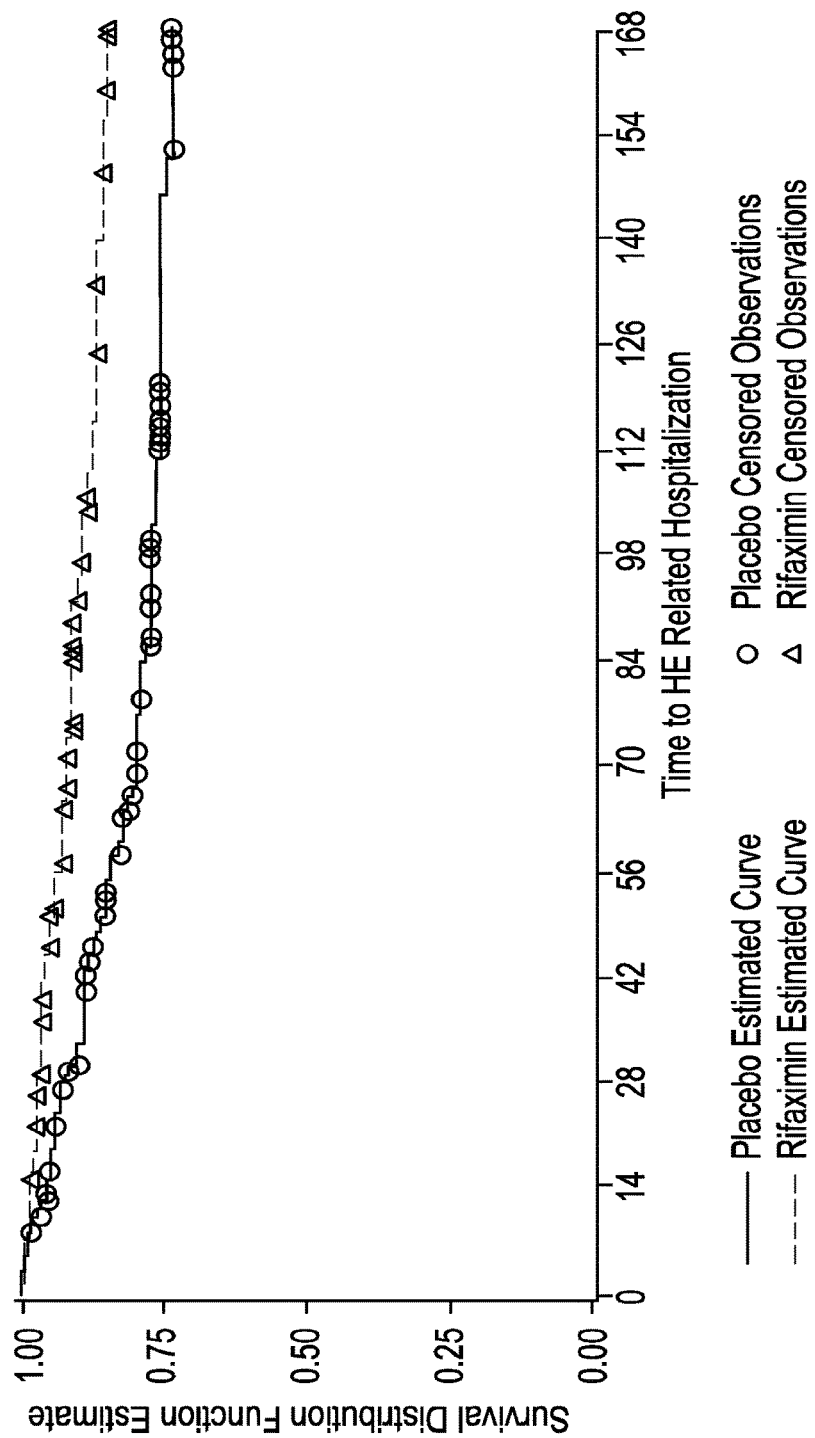
FIG. 3 is a line graph showing Kaplan Meier estimates of the distribution of time to a first HE related hospitalization.

FIG. 3 is a line graph showing Kaplan Meier estimates of the distribution of time to a first HE related hospitalization. As indicated there was an increased time to hospitalization for subjects taking rifaximin in comparison to the placebo group.

Figure 4:
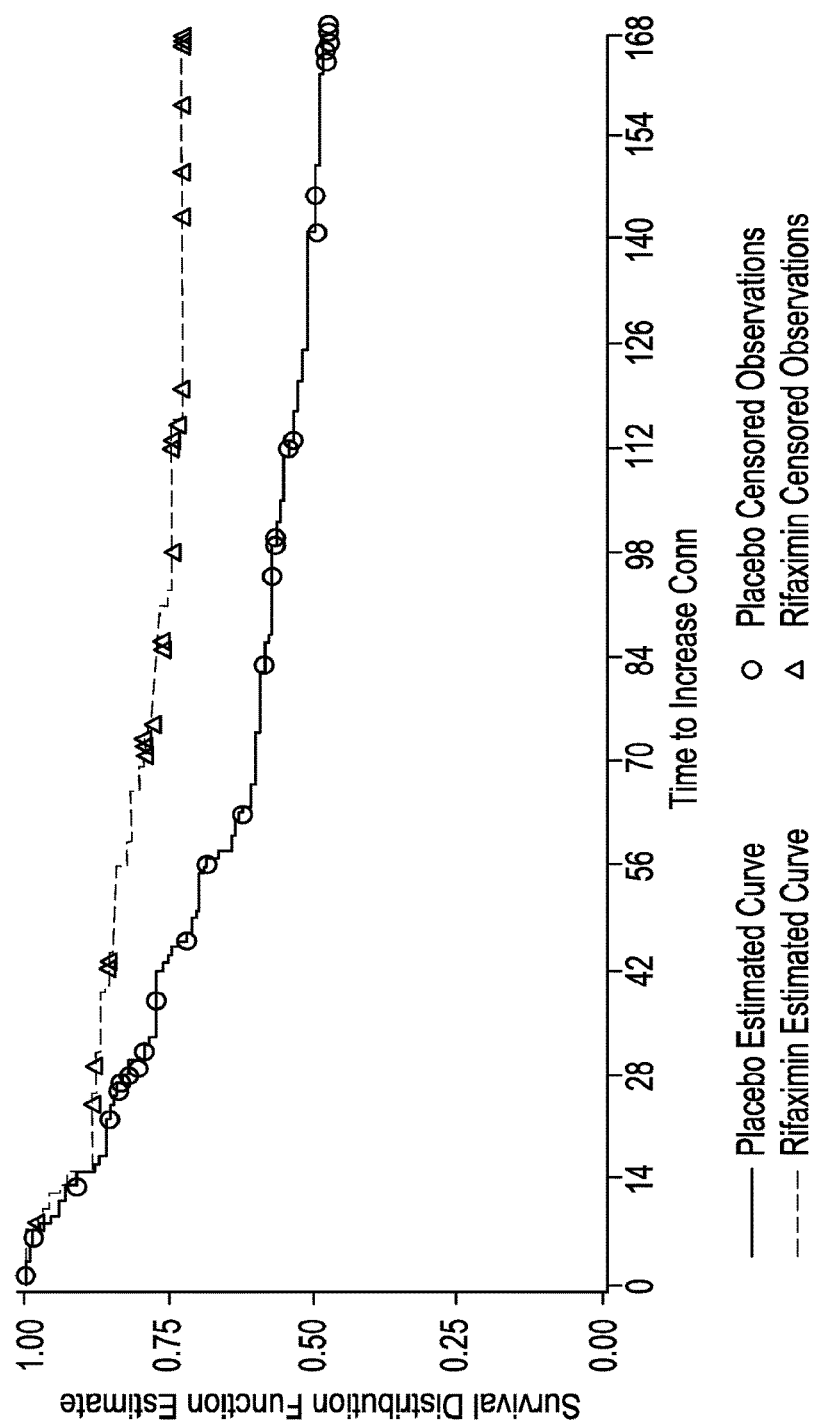
FIG. 4 is a line graph showing Kaplan Meier estimates of the distribution of time to a first increase in Conn scores.

FIG. 4 is a line graph showing Kaplan Meier estimates of the distribution of time to a first increase in Conn scores. As indicated there was an increased time to the first increase in Conn scores for subjects taking rifaximin in comparison to the placebo group.

Figure 5:
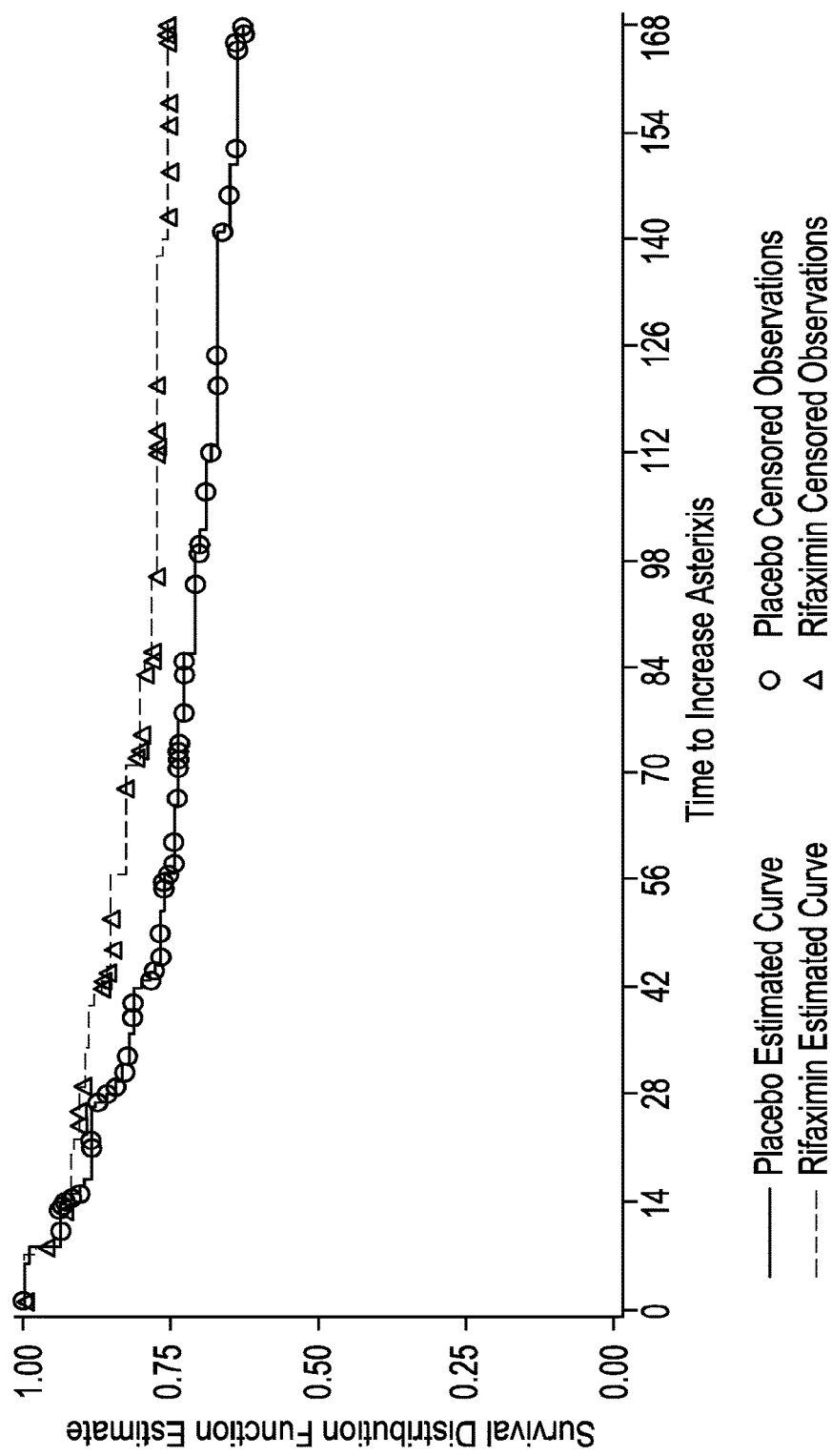
FIG. 5 is a line graph showing Kaplan Meier estimates of the distribution of time to a first increase in an Asterixis grade.
Figure 6:
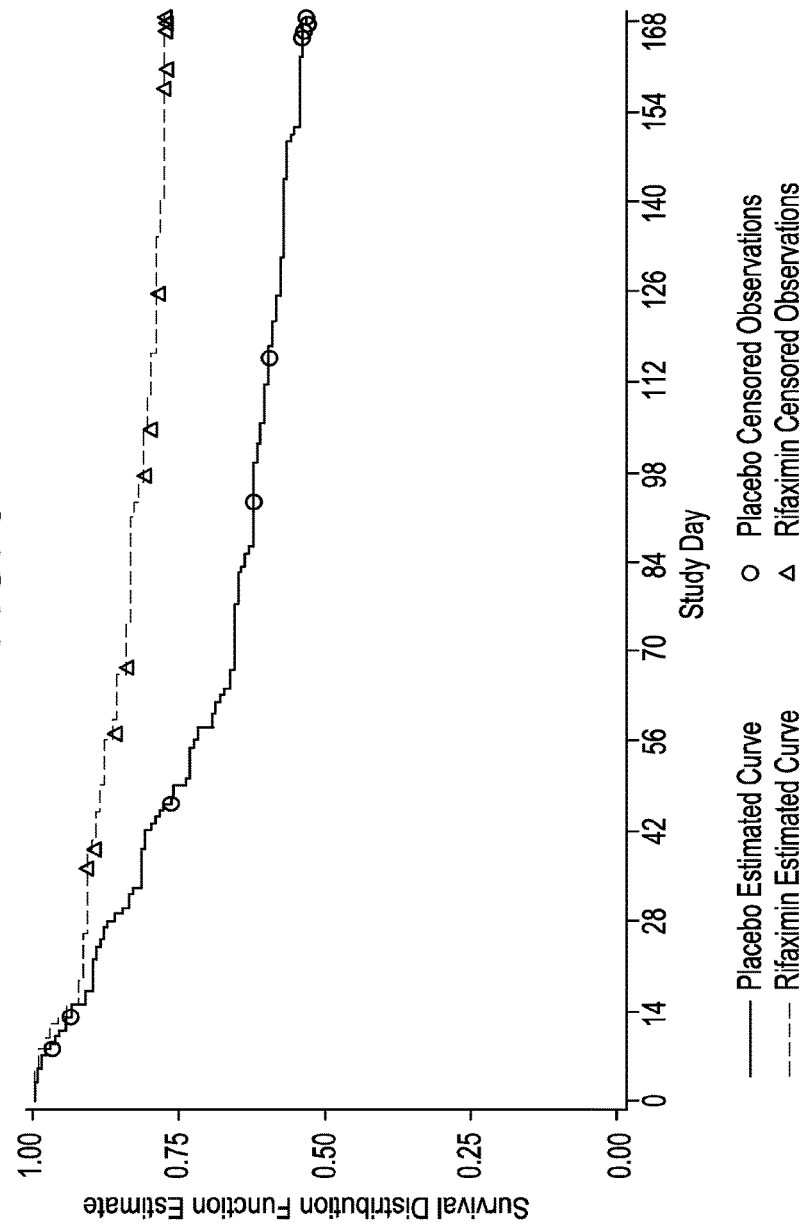
FIG. 6 depicts the time to first breakthrough overt HE episode (up to 6 months of treatment, day 170 in the first study) (ITT Population).

FIG. 5 is a line graph showing Kaplan Meier estimates of the distribution of time to a first increase in Asterixis grade. As indicated there was an increased time to the first increase in Asterixis grade for subjects taking rifaximin in comparison to the placebo group.

Example 2

The following tables provide further evidence supporting the advantageous use of GI specific antibiotics, such as rifaximin, to treat subjects suffering from HE.

TABLE 1

Time to Onset of Breakthrough HE Episode

| | Placebo (N = 159) | | | | | 550 mg Rifaximin BID (N = 140) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 158 | 20 | 20 | 0.13 (0.03) | 1.0000 | 140 | 13 | 13 | 0.09 (0.02) | 1.0000 |
| [28-56) | 137 | 23 | 43 | 0.17 (0.03) | 0.8734 | 126 | 4 | 17 | 0.03 (0.02) | 0.9071 |
| [56-84) | 113 | 14 | 57 | 0.12 (0.03) | 0.7262 | 120 | 6 | 23 | 0.05 (0.02) | 0.8783 |
| [84-140) | 98 | 10 | 67 | 0.10 (0.03) | 0.6363 | 112 | 7 | 30 | 0.06 (0.02) | 0.8344 |
| [140-168) | 84 | 6 | 73 | 0.07 (0.03) | 0.5713 | 98 | 1 | 31 | 0.01 (0.01) | 0.7820 |
| >=168 | 38 | 0 | 73 | 0.00 (0.00) | 0.5305 | 46 | 0 | 31 | 0.00 (0.00) | 0.7740 |

Harzard Ratio: 0.421
95% CI: (0.276, 0.641)
p-value: <.0001

TABLE 2

Time to Onset of Breakthrough HE Episode by Baseline Conn Score Level

| | Placebo (N = 107) | | | | | 550 mg Rifaximin BID (N = 93) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 107 | 13 | 13 | 0.12 (0.03) | 1.0000 | 93 | 11 | 11 | 0.12 (0.03) | 1.0000 |
| [28-56) | 93 | 16 | 29 | 0.17 (0.04) | 0.8779 | 81 | 3 | 14 | 0.04 (0.02) | 0.8817 |
| [56-84) | 77 | 7 | 36 | 0.09 (0.03) | 0.7269 | 77 | 1 | 15 | 0.01 (0.01) | 0.8491 |
| [84-140) | 69 | 5 | 41 | 0.07 (0.03) | 0.6608 | 75 | 3 | 18 | 0.04 (0.02) | 0.8380 |
| [140-168) | 61 | 4 | 45 | 0.07 (0.03) | 0.6129 | 68 | 1 | 19 | 0.01 (0.01) | 0.8042 |
| >=168 | 27 | 0 | 45 | 0.00 (0.00) | 0.5724 | 32 | 0 | 19 | 0.00 (0.00) | 0.7924 |

Harzard Ratio: 0.441
95% CI: (0.258, 0.754)
p-value: 0.0028

TABLE 3

Time to Onset of Breakthrough HE Episode by Prior Lactulose Use

| | Placebo (N = 142) | | | | | 550 mg Rifaximin BID (N = 123) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 141 | 19 | 19 | 0.13 (0.03) | 1.0000 | 123 | 12 | 12 | 0.10 (0.03) | 1.0000 |
| [28-56) | 121 | 21 | 40 | 0.17 (0.03) | 0.8652 | 110 | 4 | 16 | 0.04 (0.02) | 0.9024 |
| [56-84) | 100 | 13 | 53 | 0.13 (0.03) | 0.7151 | 104 | 5 | 21 | 0.05 (0.02) | 0.8696 |
| [84-140) | 86 | 10 | 63 | 0.12 (0.03) | 0.6221 | 97 | 7 | 28 | 0.07 (0.03) | 0.8278 |
| [140-168) | 73 | 5 | 68 | 0.07 (0.03) | 0.5498 | 84 | 1 | 29 | 0.01 (0.01) | 0.7678 |
| >=168 | 33 | 0 | 68 | 0.00 (0.00) | 0.5121 | 39 | 0 | 29 | 0.00 (0.00) | 0.7586 |

Harzard Ratio: 0.424
95% CI: (0.274, 0.655)
p-value: 0.0001

TABLE 4

Time to Onset of First HE-Related Hospitalization

| | Placebo (N = 159) | | | | | 550 mg Rifaximin BID (N = 140) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28] | 154 | 11 | 11 | 0.07 (0.02) | 1.0000 | 138 | 6 | 6 | 0.04 (0.02) | 1.0000 |
| [28-56] | 131 | 14 | 25 | 0.11 (0.03) | 0.9286 | 125 | 4 | 10 | 0.03 (0.02) | 0.9564 |
| [56-84] | 106 | 7 | 32 | 0.07 (0.02) | 0.8293 | 113 | 5 | 15 | 0.04 (0.02) | 0.9258 |
| [84-140] | 86 | 8 | 40 | 0.09 (0.03) | 0.7743 | 100 | 5 | 20 | 0.05 (0.02) | 0.8848 |
| [140-168] | 66 | 2 | 42 | 0.03 (0.02) | 0.7023 | 86 | 3 | 23 | 0.04 (0.02) | 0.8403 |
| >=168 | 30 | 0 | 42 | 0.00 (0.00) | 0.6810 | 39 | 0 | 23 | 0.00 (0.00) | 0.8108 |

Hazard Ratio: 0.521
95% CI: (0.313, 0.868)
p-value: 0.017

TABLE 5

Time to Any Increase from Baseline in Conn Score

| | Placebo (N = 159) | | | | | 550 mg Rifaximin BID (N = 140) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 156 | 26 | 26 | 0.17 (0.03) | 1.0000 | 139 | 17 | 17 | 0.12 (0.03) | 1.0000 |
| [28-56) | 125 | 21 | 47 | 0.17 (0.03) | 0.8333 | 119 | 5 | 22 | 0.04 (0.02) | 0.8777 |
| [56-84) | 100 | 15 | 62 | 0.15 (0.04) | 0.6928 | 109 | 9 | 31 | 0.08 (0.03) | 0.8407 |
| [84-140) | 80 | 10 | 72 | 0.13 (0.04) | 0.5883 | 94 | 5 | 36 | 0.05 (0.02) | 0.7713 |
| [140-168) | 62 | 5 | 77 | 0.08 (0.03) | 0.5143 | 79 | 0 | 36 | 0.00 (0.00) | 0.7302 |
| >=168 | 27 | 0 | 77 | 0.00 (0.00) | 0.4729 | 37 | 1 | 37 | 0.03 (0.03) | 0.7302 |

Harzard Ratio: 0.463
95% CI: (0.312, 0.685)
p-value: <.0001

TABLE 6

Time to Onset of Breakthrough HE Episode by Baseline MELD Score Level

| | Placebo (N = 44) | | | | | 550 mg Rifaximin BID (N = 34) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 44 | 2 | 2 | 0.05 (0.03) | 1.0000 | 34 | 1 | 1 | 0.03 (0.03) | 1.0000 |
| [28-56) | 42 | 4 | 6 | 0.10 (0.05) | 0.9545 | 33 | 0 | 1 | 0.00 (0.00) | 0.9706 |
| [56-84) | 38 | 1 | 7 | 0.03 (0.03) | 0.8636 | 32 | 0 | 1 | 0.00 (0.00) | 0.9706 |
| [84-140) | 37 | 3 | 10 | 0.08 (0.04) | 0.8409 | 32 | 1 | 2 | 0.03 (0.03) | 0.9706 |
| [140-168) | 33 | 4 | 14 | 0.12 (0.06) | 0.7727 | 28 | 0 | 2 | 0.00 (0.00) | 0.9398 |
| >=168 | 14 | 0 | 14 | 0.00 (0.00) | 0.6791 | 13 | 0 | 2 | 0.00 (0.00) | 0.9398 |

Harzard Ratio: 0.171
95% CI: (0.039, 0.754)
p-value: 0.0197

TABLE 7

Time to Onset of Breakthrough HE Episode by Baseline MELD Score Level

| | Placebo (N = 86) | | | | | 550 mg Rifaximin BID (N = 85) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 86 | 15 | 15 | 0.18 (0.04) | 1.0000 | 85 | 8 | 8 | 0.09 (0.03) | 1.0000 |
| [28-56) | 70 | 13 | 28 | 0.19 (0.05) | 0.8246 | 77 | 2 | 10 | 0.03 (0.02) | 0.9059 |
| [56-84) | 56 | 11 | 39 | 0.20 (0.05) | 0.6703 | 73 | 3 | 13 | 0.04 (0.02) | 0.8822 |
| [84-140) | 45 | 7 | 46 | 0.16 (0.05) | 0.5387 | 68 | 6 | 19 | 0.09 (0.03) | 0.8459 |
| [140-168) | 36 | 2 | 48 | 0.06 (0.04) | 0.4539 | 58 | 1 | 20 | 0.02 (0.02) | 0.7713 |
| >=168 | 16 | 0 | 48 | 0.00 (0.00) | 0.4284 | 27 | 0 | 20 | 0.00 (0.00) | 0.7580 |

Harzard Ratio: 0.329
95% CI: (0.195, 0.556)
p-value: <.0001

TABLE 8

Time to Onset of Breakthrough HE Episode by Baseline MELD Score Level

| | Placebo (N = 14) | | | | | 550 mg Rifaximin BID (N = 11) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 14 | 3 | 3 | 0.21 (0.11) | 1.0000 | 11 | 1 | 1 | 0.09 (0.09) | 1.0000 |
| [28-56) | 11 | 4 | 7 | 0.36 (0.15) | 0.7857 | 10 | 0 | 1 | 0.00 (0.00) | 0.9091 |
| [56-84) | 7 | 2 | 9 | 0.29 (0.17) | 0.5000 | 10 | 3 | 4 | 0.30 (0.14) | 0.9091 |
| [84-140) | 5 | 0 | 9 | 0.00 (0.00) | 0.3571 | 7 | 0 | 4 | 0.00 (0.00) | 0.6364 |
| [140-168) | 4 | 0 | 9 | 0.00 (0.00) | 0.3571 | 7 | 0 | 4 | 0.00 (0.00) | 0.6364 |
| >=168 | 2 | 0 | 9 | 0.00 (0.00) | 0.3571 | 3 | 0 | 4 | 0.00 (0.00) | 0.6364 |

Harzard Ratio: 0.403
95% CI: (0.123, 1.313)
p-value: 0.1315

TABLE 9

Time to Onset of Breakthrough HE Episode by Prior Lactulose Use

| | Placebo (N = 134) | | | | | 550 mg Rifaximin BID (N = 127) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 134 | 18 | 18 | 0.13 (0.03) | 1.0000 | 127 | 12 | 12 | 0.09 (0.03) | 1.0000 |
| [28-56) | 115 | 20 | 38 | 0.17 (0.04) | 0.8652 | 114 | 4 | 16 | 0.04 (0.02) | 0.9055 |
| [56-84) | 95 | 14 | 52 | 0.15 (0.04) | 0.7147 | 108 | 6 | 22 | 0.06 (0.02) | 0.8737 |
| [84-140) | 80 | 9 | 61 | 0.11 (0.04) | 0.6094 | 100 | 6 | 28 | 0.06 (0.02) | 0.8252 |
| [140-168) | 68 | 5 | 66 | 0.07 (0.03) | 0.5408 | 88 | 1 | 29 | 0.01 (0.01) | 0.7754 |
| >=168 | 31 | 0 | 66 | 0.00 (0.00) | 0.5011 | 41 | 0 | 29 | 0.00 (0.00) | 0.7666 |

Hazard Ratio: 0.399
95% CI: (0.258, 0.618)
p-value: <.0001

TABLE 10

Time to Any Increase from Baseline in Asterixis Grade

| | Placebo (N = 159) | | | | | 550 mg Rifaximin BID (N = 140) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 154 | 20 | 20 | 0.13 (0.03) | 1.0000 | 137 | 13 | 13 | 0.10 (0.03) | 1.0000 |
| [28-56) | 120 | 15 | 35 | 0.13 (0.03) | 0.8697 | 116 | 7 | 20 | 0.06 (0.02) | 0.9048 |
| [56-84) | 91 | 4 | 39 | 0.04 (0.02) | 0.7610 | 101 | 7 | 27 | 0.07 (0.03) | 0.8499 |
| [84-140) | 76 | 6 | 45 | 0.08 (0.03) | 0.7275 | 87 | 3 | 30 | 0.03 (0.02) | 0.7910 |
| [140-168) | 61 | 4 | 49 | 0.07 (0.03) | 0.6701 | 74 | 1 | 31 | 0.01 (0.01) | 0.7637 |
| >=168 | 27 | 1 | 50 | 0.04 (0.04) | 0.6262 | 34 | 1 | 32 | 0.03 (0.03) | 0.7534 |

Harzard Ratio: 0.646
95% CI: (0.414, 1.008)
p-value: 0.0523

TABLE 11

Mean Change from Baseline in Blood Ammonia Concentration (μg/dL)

| Assessment Time | Placebo (N = 159) | 550 mg Rifaximin BID (N = 140) | P-value |
|---|---|---|---|
| Day 28 | | | |
| n | 126 | 121 | |
| Mean | 89.3 | 88.4 | |
| SD | 48.19 | 49.02 | |
| Median | 87.0 | 74.0 | |
| Min | 2 | 25 | |
| Max | 315 | 326 | |
| Change from Baseline to Day 28 | | | |
| n | 117 | 117 | 0.6268 |
| Mean | −1.1 | −2.1 | |
| SD | 48.32 | 44.37 | |
| Median | 1.0 | −2.0 | |
| Min | −252 | −164 | |
| Max | 133 | 176 | |

TABLE 12

Mean Change from Baseline in Critical Flicker Frequency Test (Hz)

| Assessment Time | Placebo (N = 159) | 550 mg Rifaximin BID (N = 140) | P-value |
|---|---|---|---|
| Day 140 | | | |
| N | 70 | 87 | |
| Mean | 38.7 | 38.7 | |
| SD | 5.47 | 4.76 | |
| Median | 38.8 | 38.9 | |
| Min | 26 | 27 | |
| Max | 50 | 49 | |
| Change from Baseline to Day 140 | | | |
| n | 70 | 87 | 0.0266 |
| Mean | 1.1 | 1.4 | |
| SD | 4.10 | 4.84 | |
| Median | 0.9 | 1.5 | |
| Min | −12 | −15 | |
| Max | 12 | 12 | |

TABLE 13

Mean Change from Baseline in Critical Flicker Frequency Test (Hz)

| Assessment Time | Placebo (N = 159) | 550 mg Rifaximin BID (N = 140) | P-value |
|---|---|---|---|
| EOT | | | |
| n | 155 | 139 | |
| Mean | 37.6 | 37.8 | |
| SD | 5.98 | 4.88 | |
| Median | 37.9 | 37.8 | |
| Min | 21 | 25 | |
| Max | 50 | 49 | |
| Change from Baseline to EOT | | | |
| n | 155 | 139 | 0.0320 |
| Mean | 0.4 | 0.9 | |
| SD | 4.70 | 4.75 | |
| Median | 0.2 | 0.1 | |
| Min | −12 | −14 | |
| Max | 16 | 11 | |

TABLE 14

Number of Subjects in Each Level of Change from Baseline in Conn Score by Treatment Group

| Assessment Time | Statistics | Placebo (N = 159) | 550 mg Rifaximin BID (N = 140) | Odds Ratio (550 mg Rifaximin BID/Placebo) | 95% CI for Odds Ratio | P-value |
|---|---|---|---|---|---|---|
| Change from Baseline to EOT | | | | | | |
| −1 | n (%) | 18 (11.5%) | 26 (18.7%) | 2.46 | (1.49, 4.09) | 0.0005 |
| 0 | n (%) | 100 (63.7%) | 101 (72.7%) | | | |
| 1 | n (%) | 29 (18.5%) | 10 (7.2%) | | | |
| 2 | n (%) | 9 (5.7%) | 2 (1.4%) | | | |
| 3 | n (%) | 1 (0.6%) | 0 | | | |
| | n | 157 | 139 | | | |
| | Mean | 0.2 | −0.1 | | | |
| | SD | 0.74 | 0.56 | | | |
| | Median | 0.0 | 0.0 | | | |
| | Min | −1 | −1 | | | |
| | Max | 3 | 2 | | | |

TABLE 15

Number of Subjects in Each Level of Change from Baseline in Asterixis Grade by Treatment Group

| Assessment Time | Statistics | Placebo (N = 159) | 550 mg Rifaximin BID (N = 140) | Odds Ratio (550 mg Rifaximin BID/Placebo) | 95% CI for Odds Ratio | P-value |
|---|---|---|---|---|---|---|
| | | Change from Baseline to EOT | | | | |
| −2 | n (%) | 1 (0.6%) | 1 (0.7%) | 1.88 | (1.10, 3.23) | 0.0207 |
| −1 | n (%) | 14 (8.9%) | 18 (12.9%) | | | |
| 0 | n (%) | 114 (72.6%) | 108 (77.7%) | | | |
| 1 | n (%) | 18 (11.5%) | 10 (7.2%) | | | |
| 2 | n (%) | 8 (5.1%) | 2 (1.4%) | | | |
| 3 | n (%) | 1 (0.6%) | 0 | | | |
| 4 | n (%) | 1 (0.6%) | 0 | | | |
| | n | 157 | 139 | | | |
| | Mean | 0.2 | 0.0 | | | |
| | SD | 0.76 | 0.54 | | | |
| | Median | 0.0 | 0.0 | | | |
| | Min | −2 | −2 | | | |
| | Max | 4 | 2 | | | |

TABLE 16

Mean Change from Baseline for Epworth Sleepiness Total Score

| Assessment Time | Placebo (N = 159) | 550 mg Rifaximin BID (N = 140) | P-value |
|---|---|---|---|
| | Day 28 | | |
| N | 91 | 87 | |
| Mean | 9.1 | 10.0 | |
| SD | 4.84 | 5.51 | |
| Median | 8.0 | 9.0 | |
| Min | 0 | 0 | |
| Max | 21 | 23 | |
| | Change from Baseline to Day 28 | | |
| N | 90 | 86 | 0.0593 |
| Mean | −1.1 | −0.2 | |
| SD | 4.79 | 3.53 | |
| Median | −1.0 | 0.0 | |
| Min | −17 | −14 | |
| Max | 14 | 7 | |

Example 3: CYP3A4 is not Induced by Rifaximin

Induction of CYP3A4 by rifaximin was observed based on decreased midazolam AUC by ~25%. A higher systemic exposure is expected in a majority of the target patient population.

When rifaximin was orally administered at high doses (1650 mg/day) for at least 7 days, the mean $C_{max}$, $AUC_{0-t}$, and $AUC_{0-\infty}$ of midazolam were reduced by <25%. Rifaximin is a potential CYP3A4 inducer, in vitro studies have shown it to have a lower induction potency than rifampin. (The estimated intestinal lumen concentration of rifaximin is approximately 5 μM. In the in vitro study, CYP3A4 activity was induced 1.7-fold and 1.8-fold at rifaximin 1 μM and 10 μM; at the same concentrations, rifampin induced CYP3A4 3.7-fold and 4-fold, respectively. Furthermore, rifaximin's gut-targeted distribution is believed to limit its CYP3A4 induction mechanism to the intestine, sparing hepatic induction as a result of low systemic exposure. That is, there is a separation of intestinal and hepatic induction for rifaximin This is shown in studies disclosed herein in humans receiving rifaximin, as supported by the absence of induction when

TABLE 17

Time to Onset of First HE-Related Hospitalization

| | Placebo (N = 159) | | | | | 550 mg Rifaximin BID (N = 140) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 155 | 11 | 11 | 0.07 (0.02) | 1.0000 | 139 | 4 | 4 | 0.03 (0.01) | 1.0000 |
| [28-56) | 132 | 12 | 23 | 0.09 (0.03) | 0.9288 | 130 | 4 | 8 | 0.03 (0.02) | 0.9711 |
| [56-84) | 108 | 7 | 30 | 0.06 (0.02) | 0.8440 | 119 | 4 | 12 | 0.03 (0.02) | 0.9411 |
| [84-140) | 88 | 4 | 34 | 0.05 (0.02) | 0.7893 | 106 | 5 | 17 | 0.05 (0.02) | 0.9094 |
| [140-168) | 72 | 2 | 36 | 0.03 (0.02) | 0.7535 | 92 | 2 | 19 | 0.02 (0.02) | 0.8665 |
| >=168 | 34 | 0 | 36 | 0.00 (0.00) | 0.7325 | 43 | 0 | 19 | 0.00 (0.00) | 0.8475 |

Harzard Ratio: 0.500
95% CI: (0.287, 0.873)
p-value: 0.0129 either intravenous or oral midazolam was administered following rifaximin 200 mg TID for up to 7.

Without wishing to be bound by any particular scientific theory, it is thought that any risk of hepatic CYP3A4 induction likely is further mitigated in hepatically impaired patients, for whom significant fractions of portal blood flow are shunted around the liver;[3] therefore, their increased systemic exposure should be accompanied by a proportional decrease in exposure to hepatocytes and the patients should incur no net increase in risk of hepatic CYP3A4 induction.

Example 4: Drug Interaction Studies

Two clinical drug-drug interaction studies were conducted with the rifaximin 200 mg tablet and one drug-drug interaction study with the 550 mg tablet. Two studies using midazolam, a known substrate for CYP3A4, and 1 study using an oral contraceptive containing ethinyl estradiol and norgestimate were conducted to assess the effect of rifaximin on the pharmacokinetics of these drugs. Based on the results of these studies and in vitro induction and inhibition studies using human liver fractions, no clinically relevant drug interactions are anticipated with rifaximin.

Although in vitro studies demonstrated the potential of rifaximin to interact with cytochrome P450 3A4 (CYP3A4), a clinical drug-drug interaction study demonstrated that rifaximin did not significantly affect the pharmacokinetics of midazolam either presystemically or systemically. An additional clinical drug-drug interaction study showed no effect of rifaximin on the presystemic metabolism of an oral contraceptive containing ethinyl estradiol and norgestimate. Therefore, clinical interactions with drugs metabolized by human cytochrome P450 isoenzymes are not expected.

Two studies have been performed to evaluate the potential for drug interactions with midazolam. The first was an open-label, randomized, crossover, drug-interaction trial designed to assess the effect of rifaximin 200 mg administered orally (PO) every 8 hours (Q8H) for 3 days and every 8 hours for 7 days, on the pharmacokinetics of a single dose of either midazolam 2 mg intravenous (IV) or midazolam 6 mg PO. No significant difference was observed in the metrics of systemic exposure or elimination of IV or PO midazolam or its major metabolite, 1'-hydroxymidazolam, between midazolam alone or together with rifaximin. Therefore, rifaximin was not shown to significantly affect intestinal or hepatic CYP3A4 activity.

The second study, an open-label, drug-interaction study examined the effect of rifaximin, 550 mg three times daily, on orally administered (PO) midazolam 2 mg when dosed for 7 and 14 consecutive days. In this study rifaximin was shown to be a weak inducer of CYP3A4; given the low systemic exposure of rifaximin, this interaction is believed to be limited to the gastrointestinal tract. This induction is both dose- and dosing-duration dependent. When rifaximin was orally administered at high doses (1650 mg/day) for at least 7 days, the mean $C_{max}$, $AUC_{0-t}$, and $AUC_{0-\infty}$ of midazolam were reduced by <25%.

In vitro hERG potency and in vitro protein binding of rifaximin. In the in vitro hERG studies, rifaximin concentrations up to 300 μM failed to achieve 50% inhibition of the hERG potassium current. Due to rifaximin precipitation at 300 μM, the $IC_{50}$ was estimated to be greater than 100 μM. In fact, 50% inhibition could not be achieved; at 100 μM, mean inhibition was 34.5%. The highest $C_{max}$ observed in a hepatically impaired patient in a study was 52.2 ng/mL (0.0664 μM); the highest free fraction observed in a subset of plasma samples from patients enrolled in this study was 44.7%. Using these numbers, the highest anticipated free plasma exposure would be 0.03 μM, which represents a reduction of ≥3000-fold in comparison with the highest concentration at which rifaximin could be tested in the hERG experiments. This safety margin greatly exceeds the 30-fold separation between hERG $IC_{50}$ and unbound $C_{max}$ that is commonly associated with minimization of risk of clinical QT prolongation.

Example 5: Time to First Breakthrough Event

An efficacy parameter for a first study was the occurrence of an episode of breakthrough overt HE during treatment. Breakthrough overt HE episodes were measured by using the Conn score (or West Haven grade), and the asterixis grade. A breakthrough overt HE episode, as defined for the first study, was a marked, clinically significant deterioration in neurological function that can result in a deleterious effect on self care, and lead to hospitalization. The efficacy endpoint, time to first breakthrough overt HE episode, showed a highly significant protective effect of rifaximin (p<0.0001 for between-group difference in relative risk). Rifaximin treatment resulted in a 57.9% reduction, when compared with placebo, in the risk of experiencing breakthrough overt HE during the 6-month treatment period.

In addition, this study also showed that the time to first breakthrough overt HE also showed a highly significant protective effect of rifaximin when analyzed in separate geographic regions, North America versus Russia.

Rifaximin treatment results in fewer overt HE episodes that may otherwise incapacitate the patient, may alleviate the burden on family members who are required to care for the patient, and reduces the burden of hospitalization in this patient population and the healthcare system.

In a second study, similar results were shown, for example, the second study with respect to time to first breakthrough overt HE episode: the Kaplan-Meier estimates of time to first breakthrough overt HE episode were similar between the rifaximin group in the first study and new rifaximin subjects in this second study. Also, similar proportions of subjects had breakthrough overt HE in the rifaximin group of the first study (22%, 31 of 140 [rifaximin group]) and in the new rifaximin group of the second study (27.6%, 54 of 196).

Additionally, when the first study placebo subjects crossed over to rifaximin therapy by entering the second study, a protective effect of rifaximin was observed: the first study a 70% reduction in risk of experiencing breakthrough overt HE during rifaximin treatment in the second study when compared with their prior placebo experience in the first study. This reduction took place in spite of the aging and presumably progressing nature of the population with chronic liver disease.

The second study also showed that the protective effect of rifaximin was durable: the estimate of time-to-first breakthrough HE demonstrated long-term maintenance of remission from breakthrough HE when rifaximin subjects in remission after participation in the first study were followed in the second study (up to 680 days of rifaximin therapy; median exposure durations were 168 days in the first study and 253 days in the second study). The incidence of breakthrough HE episode for these rifaximin subjects relative to the first study placebo was lower, an indication of fewer breakthrough HE episodes with rifaximin treatment.

A critical flicker frequency (CFF) assessment, a recognized quantitative measure of CNS dysfunction, was an efficacy endpoint in the first study. CFF tests utilize the correlation between cerebral processing of oscillatory visual stimuli and CNS impairment due to increased HE severity. This test identifies a frequency at which a flickering light is perceived as steady. A decline in this frequency has been associated with increasing severity of HE. Likewise, elevation in blood ammonia, another endpoint in the first study, is a quantitative assessment associated with the CNS effects underlying overt HE.

Comparisons of changes from baseline to end of study in CFF results and in venous ammonia levels showed statistically significant, greater improvement over the course of the study in the rifaximin group when compared to placebo (p=0.0320 for CFF changes and p=0.0391 for venous ammonia changes). In the first study, a correlation between CFF results and breakthrough overt HE (primary efficacy measure) was noted. Venous ammonia levels were found to be correlated to the occurrence of breakthrough overt HE in the first study.

Results for other efficacy endpoints also demonstrated protective effects of rifaximin. In particular, the other efficacy endpoint of time to first HE-related hospitalization showed a reduction in risk for rifaximin subjects.

In the first study, the analysis of time to first HE-related hospitalization (e.g., hospitalization directly resulting from HE or hospitalization complicated by HE) demonstrated that the reduction in risk of hospitalization due to HE was 50% in the rifaximin group, when compared with placebo, during the 6-month treatment period. The HE-related hospitalization rate was 0.38 event/person exposure years (PEY), rifaximin versus 0.78 event/PEY, placebo after normalization to exposure.

In the first study, the risk of HE-caused hospitalization (e.g., hospitalization directly resulting from HE only) was reduced by 56% in the rifaximin group when compared with placebo. The HE-caused hospitalization rate was 0.30 events/PEY in the rifaximin group versus 0.72 event/PEY in the placebo group.

In the first study, the risk of all-cause hospitalization rate was reduced by 30% in the rifaximin group when compared to placebo. The all-cause hospitalization rate was 0.92 events/PEY in the rifaximin group versus 1.31 event/PEY in the placebo group.

In the second study, the low HE-caused hospitalization rate was maintained at rates consistent with those in the first study: HE-caused hospitalization rate was 0.29 event/PEY and all cause hospitalization in the second study was 0.66 event/PEY. The consistently low HE-related/HE-caused hospitalization rate in rifaximin-treated subjects in the first study and in the second study was at least partly a result of maintaining remission from demonstrated HE in subjects with end-stage liver disease.

Hepatic encephalopathy is associated with a low quality of life compared to age-matched patients without HE. Patients with HE experience symptoms including fatigue, daytime sleepiness, and lack of awareness (Conn score 1); and confusion and disorientation (Conn score 2) that significantly interfere with day-to-day function and decreased ability for self care. Often, this lack of self care can lead to improper nutrition and non-adherence to therapy and can further escalate into more severe symptoms such as increased somnolence, gross disorientation and stupor, which require hospitalization. Rifaximin treatment protects against HE related/caused hospitalization, thereby improving the functional status for the patient and benefitting his/her caregiver; and reducing the economic cost related to liver cirrhosis and associated HE.

There are limited treatment options in the United States for patients with recurrent HE. Neomycin sulfate is only approved for the adjunctive therapy in hepatic coma. Conventional therapy aims to lower the production and absorption of ammonia. Nonabsorbable disaccharides, eg, lactulose or lactitol, are typically used as first-line therapy for HE. There is evidence that nonabsorbable disaccharides lower plasma levels of ammonia by changing nitrogen metabolism in colonic flora and increasing fecal excretion of nitrogen. Broad spectrum, GI-active antibiotics including neomycin, metronidazole, vancomycin, and paromomycin have been used with or without lactulose. These antibiotics appear to act indirectly by inhibiting the splitting of urea by deaminating bacteria, thus reducing the production of ammonia and other potential toxins. Current guidelines recommend (not FDA approved) antibiotic therapy with neomycin or metronidazole as an alternative to treatment with nonabsorbable disaccharides.

Common side effects of nonabsorbable disaccharide (e.g., lactulose) therapy include an unpleasant taste that can hinder treatment compliance, a dosing schedule that is linked to bowel habits, and GI side effects such as bloating, abdominal cramps, and diarrhea. Diarrhea resulting in dehydration has been reported with the use of lactulose, a significant consequence for patients with HE as electrolyte abnormalities can worsen HE and lead to renal dysfunction.

The use of systemically absorbed antibiotics such as neomycin in the treatment of HE is hampered by ototoxicity and nephrotoxicity associated with long-term use. The incidence of aminoglycoside-induced nephrotoxicity is substantially greater in patients with advanced liver disease than in patients without liver disease. The frequency of aminoglycoside-induced nephrotoxicity in the general population is 3% to 11%. Leitman reported that nephrotoxicity occurred in 73% of patients with liver disease versus 34% of patients without liver disease who received aminoglycosides by intravenous administration during hospitalization; and Cabrera reported that renal tubular damage or functional renal impairment was observed in 60% of aminoglycoside-treated cirrhotic patients (intravenous administration during hospitalization). Additionally, a high mortality rate and sustained renal damage were noted in cirrhotic patients who developed aminoglycoside-induced renal tubular damage. Therefore, aminoglycosides are now widely considered as contraindicated in patients with advanced liver disease.

Rifaximin is an attractive therapy for the treatment of patients with HE because of its demonstrated effectiveness, favorable safety profile, and because of disadvantages of systemic aminoglycosides and nonabsorbable disaccharides. Rifaximin has a broad spectrum of in vitro antibacterial activity against both Gram-positive and Gram-negative bacteria and against aerobic and anaerobic isolates.

Since rifaximin is poorly absorbed after oral administration, the drug is selectively active in the gastrointestinal tract. Additionally, there is a low risk of drug-drug interactions with the use of rifaximin. Rifaximin has a lower rate of fecal eradication of pathogens compared with other commonly used antibacterial drugs and causes minimal alterations in gut flora suggesting that rifaximin has a different mechanism of action than other commonly used drugs in enteric bacterial infection, such as the fluoroquinolones. The risk of the development of antibiotic resistance is low during chronic treatment with rifaximin when compared to other systemic antibiotics such as neomycin, possibly because resistance is mediated by a mutation in host cell DNA and is not plasmid based.

In a retrospective chart review, the numbers and durations of hospitalizations due to HE, the total cost of therapy, and HE endpoints (asterixis grade, Conn score) were found to be dramatically reduced when compared to lactulose treatment in patients with HE who received lactulose daily for 6 months and then received rifaximin daily for 6 months.

The first study was designed to overcome the limitations of previous studies reported in the literature (e.g., heterogeneous subject populations, small population size, short durations, and insufficient endpoints for mental status).

First, treatment duration was increased to 6 months. This longer duration was planned to allow for a greater number of subjects to experience an HE episode than if the study was limited to ≤6 weeks. Also, the longer treatment duration provided an opportunity to evaluate the long-term safety of rifaximin in subjects with chronic hepatic cirrhosis and associated recurrent, overt, episodic HE. The study investigated consequences of HE with respect to patient care and economic cost by measuring hospitalizations due to HE episodes as a key secondary efficacy endpoint.

To evaluate overt HE episodes by using clinically relevant criteria in the first study and study the second study, mental status impairment was measured by using Conn score (West Haven criteria) and the severity of neuromotor abnormalities was measured by asterixis grade. The Conn score ranges from Stage 0 (lack of detectable changes in personality) to Stage 4 (coma, decerebrate posturing, dilated pupils). The Conn score is the recommended and widely used gold standard for grading the severity of impaired mental status in overt HE. Asterixis (flapping tremor) is a neuromotor symptom of overt HE that increases in severity with worsening neurological impairment.

The control group for the first study received matched placebo tablets in parallel with rifaximin treatments in the active group. The second study was an ongoing open-label, treatment-extension study to evaluate the long-term safety of rifaximin 550 mg BID in subjects with a history of recurrent, episodic, overt HE. In addition to safety measurements, Conn scores and asterixis grades were assessed during the course of the study to measure the protective effect of rifaximin against breakthrough overt HE during treatment for up to approximately 1 year in subjects who completed up to 6 months of rifaximin treatment in the first study and then entered the second study; in subjects who received placebo in the first study and crossed over to rifaximin treatment in the second study; and in patients with a history of HE who entered the second study as new subjects.

The dosage regimen used (550 mg BID) was based on past clinical experience with rifaximin in patients with HE and other subject populations. In several previous studies, rifaximin was safe and effective in subjects with HE at a dose of 1200 mg per day with or without concomitant lactulose. In a 6-month study of rifaximin versus neomycin (14 days on-treatment and 14 days off-treatment per month), rifaximin 1200 mg/day and neomycin (3 g/day) had comparable efficacy in patients with HE. Aminoglycoside antibiotics are contraindicated in patients with advanced liver disease because of the risk of nephrotoxicity.

An efficacy endpoint was the time to first breakthrough overt HE episode. A breakthrough overt HE episode was defined as an increase of Conn score to Grade ≥2 (e.g., 0 or 1 to ≥2) or an increase in Conn and asterixis score of 1 grade each for those subjects who entered the study with a Conn score of 0. Time to breakthrough overt HE episode was the duration from time of first dose of study drug to the first breakthrough overt HE episode. Subjects who completed the study and did not experience a breakthrough overt HE episode were censored at the time of their 6-month visit. Subjects who terminated early for reasons other than breakthrough overt HE were contacted at 6 months from randomization to determine if subjects had experienced a breakthrough overt HE episode or other outcome (e.g., mortality status); and, if the subject had no breakthrough overt HE event prior to contact, he/she was censored at the time of contact. Therefore, complete capture was achieved for breakthrough overt HE episodes up to 6 months postrandomization. Subjects in the study had ≥2 episodes of overt HE equivalent to Conn score ≥2 within 6 months prior to screening (i.e., subjects had documented recurrent, overt HE). At the baseline assessment, subjects were in remission with a Conn score of 0 or 1. A breakthrough overt HE episode, as defined above, was a marked deterioration in neurological function.

Other efficacy endpoints in the first study included, for example:
1. Time to first HE-related hospitalization;
2. Time to any increase from baseline in Conn score (mental state grade);
3. Time to any increase from baseline in asterixis grade;
4. Mean change from baseline in fatigue domain scores on the CLDQ at end of treatment; and
5. Mean change from baseline in venous ammonia concentration at end of treatment.

Presented herein are the results of the first study and second study. The first study was a double-blind, randomized, placebo-controlled study evaluating the efficacy and safety of rifaximin 550 mg BID as compared to placebo. Subjects in remission from demonstrated recurrent, overt, episodic HE associated with chronic, hepatic cirrhosis were randomized on Day 0 (Visit 2) according to a 1:1 ratio to receive rifaximin 550 mg BID or placebo for 6 months. The primary efficacy endpoint was the time to breakthrough overt HE. Breakthrough overt HE was defined as an increase of Conn score to Grade ≥2 (e.g., 0 or 1 to ≥2) or an increase in Conn and asterixis score of 1 grade each for those subjects who entered the study with a Conn score of 0. Subjects discontinued from the study at the time of breakthrough overt HE episode. After participation in the first study, subjects had the option to enroll in the open-label, treatment-extension study (the second study).

A total of 299 subjects were randomized to receive rifaximin (140 subjects) or placebo (159 subjects). All randomized subjects received at least 1 dose of study drug. A total of 251 (84%) (116 [rifaximin], 135 [placebo]) subjects completed the study as specified in the protocol (e.g., completed 6 months of treatment or withdrew from the study at the time of breakthrough overt HE).

Subjects in the study had ≥2 episodes of overt HE equivalent to Conn score ≥2 within 6 months prior to screening (e.g., subjects had recurrent, overt HE). At the baseline assessment, subjects were in remission with a Conn score of 0 or 1. A breakthrough overt HE episode was a marked deterioration in neurological function. Breakthrough overt HE episodes were experienced by 31 of 140 subjects in the rifaximin group and by 73 of 159 subjects in the placebo group during the 6-month treatment period (up to Day 170). Comparison of Kaplan-Meier estimates of time to breakthrough overt HE between groups showed a protective effect of rifaximin (p<0.0001). These data show that rifaximin treatment resulted in a 57.9% reduction, when compared with placebo, in the risk of experiencing breakthrough overt HE. Rifaximin treatment results in fewer overt HE episodes that may otherwise incapacitate the patient, may alleviate the burden on family members who are required to care for the patient, and reduces the burden of hospitalization in this patient population and the healthcare system.

The following prognostic factors were found to be predictors of breakthrough overt HE episodes: baseline age (p=0.0160), MELD score (p=0.0003), duration of current verified remission (p=0.1089), and number of prior HE episodes (p=0.0022). These data show that rifaximin treatment, resulted in a 60% reduction, when compared with placebo, in the risk of experiencing a breakthrough overt HE episode during the course of this study (p<0.0001).

Time to first HE-related hospitalization; and the frequencies of HE-related and all-cause hospitalizations Hepatic encephalopathy-related hospitalizations (hospitalization directly resulting from HE or hospitalization complicated by HE) were reported for 19 of 140 subjects and 36 of 159 subjects in the rifaximin and placebo groups, respectively. Rifaximin had a protective effect against HE-related hospitalization during the 6-month treatment period. Subjects in the rifaximin group had a 50% reduction in the risk of hospitalization due to HE during the 6-month treatment period when compared with placebo. The HE-related hospitalization rate was 0.38 events/PEY in the rifaximin group versus 0.78 event/PEY in the placebo group.

Hepatic encephalopathy-caused hospitalizations (hospitalization directly resulting from HE only) were reported for 15 of 140 subjects and 33 of 159 subjects in the rifaximin and placebo groups, respectively. Rifaximin had a significant protective effect against HE-caused hospitalization during the 6-month treatment period; hazard ratio in the rifaximin group relative to placebo was 0.438 (95% CI: 0.238 to 0.807) (p=0.0064) for the risk of HE-caused hospitalization. Subjects in the rifaximin group had a 56% reduction in the risk of hospitalization due to HE during the 6-month treatment period when compared with placebo. The HE-caused hospitalization rate was 0.30 events/PEY in the rifaximin group versus 0.72 event/PEY in the placebo group.

All-cause hospitalization was also lower in the rifaximin group (46 of 140) than in the placebo group (60 of 159) (30% reduction in the rifaximin group compared with placebo). The all cause hospitalization rate, after normalizing for subject exposure, was 0.90 events/PEY in the rifaximin group and 1.26 event/PEY in the placebo group. The HE-related hospitalization rate was 0.38 event/PEY in the rifaximin group and 0.78 event/PEY in the placebo group. Rifaximin treatment protects against HE-related hospitalization, thereby improving the quality of life for the patient and for his/her caregiver, and reducing the economic cost related to liver cirrhosis and associated HE.

Time to any increase from baseline in Conn score and time to any increase from baseline in asterixis grade Protective effects of rifaximin were observed with respect to both of these endpoints when analyzed independently; hazard ratio in the rifaximin group relative to placebo was 0.463 (95% CI: 0.312 to 0.685) (p<0.0001) for the risk of experiencing an increase in Conn score and 0.646 (95% CI: 0.414 to 1.008) (p=0.0523) for the risk of experiencing an increase in asterixis grade during the 6-month treatment period.

Changes from Baseline in Venous Ammonia Levels at End of Treatment

Subjects in the rifaximin group had greater reductions in venous ammonia levels when compared to placebo-treated subjects (p=0.0391).

Venous ammonia levels, a quantitative assessment that is associated with the CNS effects underlying overt HE, was found to be highly correlated to the occurrence of breakthrough overt HE as determined by the clinical evaluation of Conn score (or a combination of Conn score and asterixis grade).

Tracking of Conn Scores and Asterixis Grades: Changes from Baseline in Conn Scores and Asterixis Grades A favorable treatment effect of rifaximin was observed, when compared with placebo, with respect to the proportions of subjects who had changes of −1 (improvement) or 0 (no change); or 1, 2, or 3 (worsening) in Conn score from baseline to end of treatment (last postbaseline assessment or assessment at time of breakthrough HE). In the rifaximin group compared to placebo, higher proportions of subjects experienced Conn score changes of −1 or no change (77.1% versus 53.9%) and lower proportions of subjects had Conn score changes of 1, 2, 3, or 4. Thus, treatment with rifaximin was more effective than placebo in the prevention of worsening of Conn score (2.46 times versus placebo, p=<0.0001).

For changes from baseline to end of treatment in asterixis grade, significantly higher proportions of subjects in the rifaximin group versus the placebo group had changes from baseline in asterixis grades of −2, −1, and 0 (88.5% versus 77.0%), and significantly lower proportions of subjects had changes of 1, 2, 3, or 4 (11.6% versus 23.2%). Thus, treatment with rifaximin was more effective than placebo in the prevention of worsening of asterixis grade (1.92 times versus placebo, p=0.0262).

Changes from Baseline in CFF Results

Increases in CFF results represent improvement in neurological function in patients with HE.[10,11] Subjects in the rifaximin group had significantly greater increases in CFF results from baseline to end of treatment when compared with placebo. Mean changes (±standard deviation [SD]) in CFF results were 0.945 (±4.75) in the rifaximin group versus 0.355 (±4.70) in the placebo group (p=0.0320 for between-group difference). Similar to venous ammonia levels, CFF was shown to be highly predictive of breakthrough HE.

Median exposure to study drug was 168 days (range: 10 to 178) in the rifaximin group and 110 days (range: 6 to 176) in the placebo group. A total of 64 subjects (33 [rifaximin] and 31 [placebo]) received treatment for 141 to 168 days and 98 subjects (57 [rifaximin] and 41 [placebo]) received treatment for >168 days. Duration of exposure results are consistent with the finding that lower proportions of subjects in the rifaximin group than in the placebo group experienced breakthrough overt HE resulting in study discontinuation (per protocol, subjects discontinued from the study after breakthrough overt HE).

The percentages of subjects who had treatment-emergent AEs, severe TEAEs, drug-related TEAEs, treatment-emergent SAEs, TEAEs resulting discontinuation, and who died were similar between placebo and rifaximin groups. A total of 79.9% of subjects (239 of 299) experienced TEAEs during the course of the study. The most common TEAEs (e.g., in ≥10% of total subjects [combined placebo plus rifaximin]) experienced by subjects were the following: diarrhea (10.7% [rifaximin] versus 13.2% [placebo]), nausea (14.3% versus 13.2%), peripheral edema (15% versus 8.2%), fatigue (12.1% versus 11.3%), dizziness (12.9% versus 8.2%), ascites (11.4% versus 9.4%), and headache (10% versus 10.7%).

The second study is an ongoing open-label, treatment-extension study evaluating the long-term safety of rifaximin 550 mg BID in subjects with a history of recurrent, overt, episodic HE. All eligible subjects had a history of overt HE episodes with a documented severity equivalent to Conn score ≥2 within 12 months prior to screening (≥1 qualifying episode was required), a Conn score of ≤2 at the baseline assessment, and either participated in the first study or were new subjects. Unlike the first study, subjects were not required to withdraw from the study after experiencing a breakthrough overt HE episode.

A total of 267 subjects were enrolled and 208 were active at the time of the interim clinical cutoff. Additional data were collected for the interim report up to the time of database freeze.

Conn scores and asterixis grades were assessed during the course of the study. Therefore, it was possible to determine time to breakthrough overt HE episode for subjects who completed 6 months of rifaximin treatment in the first study and then entered the second study, subjects who received placebo in the first study and then started rifaximin in the second study, and in new subjects who started rifaximin therapy in the second study. In subjects who took rifaximin for up to 680 days (1.9 years), breakthrough overt HE episodes during the treatment period were experienced by 72 of 266 subjects (27.1%) overall: 54 of 196 subjects (27.6%) in the new rifaximin group and 18 of 70 subjects (25.7%) in the continuing rifaximin group.

Time-to-first-breakthrough HE profiles were similar between the rifaximin group in the first study and the new rifaximin group in the second study. A durable protective effect of rifaximin was observed in subjects who received rifaximin starting in the first study and continuing in the second study (median exposures to rifaximin were 168 days in the first study and 253 days in the second study)

A total of 133 of 266 subjects were hospitalized for any cause: 98 in the new rifaximin group, and 35 in the continuing rifaximin group. Normalizing for subject exposure, this represents a hospitalization rate of 0.60 event/PEY. A total of 59 were hospitalized due HE episodes (e.g., HE-caused). Normalizing for subject exposure, this represents an HE-caused hospitalization rate of 0.29 event/PEY. The low HE-caused hospitalization rate was consistent between rifaximin therapy in the second study (0.29 event/PEY) and in the first study rifaximin (0.30 event/PEY) at least partly as a result of maintaining remission from demonstrated HE in subjects with end-stage liver disease. Tracking of Conn scores and asterixis grades: changes from baseline in Conn scores and asterixis grades Conn scores were generally maintained or improved with rifaximin use up to 18 months. At the last visit, 70.7% of subjects (188 of 266 subjects) had no change and 20.3% (54 of 266) had improvements in Conn scores compared with baseline, indicating that mental status was maintained or improved in the majority of subjects (91%) over the treatment period. Of the 84 subjects (70 new rifaximin and 14 continuing rifaximin) who entered the study with Conn scores of 1, 2, or 3 (e.g., those subjects for whom measurable improvement was possible), 54 subjects (54/84=64.3%) showed a 1-grade (47 subjects; 56.0%) or 2-grade (7 subjects; 8.3%) improvement from baseline at the last visit recorded for the interim analysis. All subjects were capable of worsening over time, and 24/266 subjects (9.0%) did so by 1 or 2 grades.

Like Conn scores, asterixis grades were generally maintained or improved with rifaximin use up to 18 months. At the last visit, 77.1% of subjects (205 of 266 subjects) had no change and 16.2% (43 of 266) had improvements in asterixis scores compared with baseline, indicating that neuromotor symptoms associated with increasing neurological impairment were maintained in 83.3% of subjects over the treatment period. Of the 67 subjects (55 new rifaximin and 12 continuing rifaximin) who entered the study with asterixis scores of 1, 2, or 3 (e.g., those subjects for whom improvement was possible), 43 subjects (43/67=64.2%) showed a 1- (34 subjects; 50.7%), 2- (4 subjects; 6.0%), or 3-grade (5 subjects; 7.5%) improvement from baseline at the last visit recorded for this interim analysis. All subjects were capable of worsening over time, and 18/266 subjects (6.8%) did so by 1, 2, or 4 grades; the incidence of worsening asterixis grades were similar between the new (12/196 subjects; 6.1%) and continuing (6/70 subjects; 8.6%) rifaximin groups.

Median exposures in study the second study were 253 days (range: 7 to 680) in the new rifaximin group (subjects who received placebo in the first study or subjects who did not participate in the first study), 265.5 days (range: 10 to 673) in the continuing rifaximin group (subjects who received rifaximin in the first study and the second study), and 255 days (range: 7 to 680) in the all rifaximin group (all subjects who received rifaximin in the second study). At the time of this interim analysis, most subjects had received rifaximin for 6 to <9 months (21.4%) or 9 to <12 months (32.3%).

At the time of this interim analysis, TEAEs were reported in 230 subjects (86.5%). The most common TEAEs (e.g., in ≥10% of total subjects) experienced by subjects were the following: peripheral edema (15.8%); urinary tract infection and nausea (12.8% each); and abdominal pain and ascites (10.5% each). Note that signs and symptoms associated with HE were not considered AEs unless they met the definition of an SAE, so the number of subject with HE counted in efficacy analysis (72 subjects; 27.1%) is higher than that counted for the safety analyses (57 subjects; 21.4%).

Most TEAEs were mild or moderate in intensity, with 40.2% of subjects experiencing at least 1 TEAE that was judged by the investigator to be severe. The incidence of TEAEs considered related to study drug was comparable between the new rifaximin group (7.7%) and the continuing rifaximin group (7.1%). Treatment-emergent SAEs were experienced by 47.4% of subjects.

FIG. 1 illustrates Kaplan-Meier estimates of time to first breakthrough overt HE episode by treatment group in the ITT population. Table 18 presents Kaplan-Meier estimates of the proportions of subjects who experienced breakthrough overt HE over the course of the Treatment Period and results of statistical analyses. Subjects who completed the study and did not experience a breakthrough overt HE event were censored at the time of their 6-month visit. Subjects who terminated early for reasons other than breakthrough overt HE (eg, liver transplant, AE, subject request) were contacted at 6 months from date of randomization to determine if subjects had experienced a breakthrough overt HE episode or other outcome (e.g., mortality status). Subjects without breakthrough overt HE were censored at the time of contact or death, whichever was earlier. Therefore, complete capture was achieved for breakthrough overt HE episodes up to 6 months.

TABLE 18

The First Study: Kaplan-Meier Estimates and Statistical Analyses of
Time to First Breakthrough Overt HE (up to 6 Months of Treatment, Day 170)
(ITT Population)

| Treatment interval (days) | Placebo (N = 159) | | | | | Rifaximin (N = 140) | | | | |
|---|---|---|---|---|---|---|---|---|---|---|
| | At Risk[a] | Number of events[b] | Cumulative number of events | Event probability (SE)[c] | Probability of no breakthrough overt HE[d] | At Risk[a] | Number of events[b] | Cumulative number of events | Event probability (SE)[c] | Probability of no breakthrough overt HE[d] |
| 0 to <28 | 158 | 20 | 20 | 0.13 (0.03) | 1.0000 | 140 | 13 | 13 | 0.09 (0.02) | 1.0000 |
| 28 to <56 | 137 | 23 | 43 | 0.17 (0.03) | 0.8734 | 126 | 4 | 17 | 0.03 (0.02) | 0.9071 |
| 56 to <84 | 113 | 14 | 57 | 0.12 (0.03) | 0.7262 | 120 | 6 | 23 | 0.05 (0.02) | 0.8783 |
| 84 to <140 | 98 | 10 | 67 | 0.10 (0.03) | 0.6363 | 112 | 7 | 30 | 0.06 (0.02) | 0.8344 |
| 140 to <168 | 84 | 6 | 73 | 0.07 (0.03) | 0.5713 | 98 | 1 | 31 | 0.01 (0.01) | 0.7820 |
| ≥168 | 38 | 0 | 73 | 0 | 0.5305 | 46 | 0 | 31 | 0 | 0.7740 |

Hazard ratio: 0.421[e]
95% CI: (0.276, 0.641)
p-value <0.0001

[a]Number of subjects at risk during the treatment interval, estimated using the life table method. Assuming that censored cases were at risk for half of the interval, they only counted for half in figuring the number at risk.
[b]Number of events occurring during the treatment interval.
[c]Estimate of the probability of experiencing breakthrough overt HE during the treatment interval. Standard error (SE) estimated by using Greenwood's formula.
[d]Estimate of the probability of no breakthrough overt HE until at least the beginning of the next treatment interval.
[e]Hazard ratio estimate (hazard of breakthrough overt HE in the rifaximin group compared with the placebo group) determined from the Cox proportional hazards model. P-value based on the Score statistic.

Breakthrough overt HE episodes were experienced by 31 of 140 subjects in the rifaximin group and by 73 of 159 subjects in the placebo group during the 6-month period since randomization (up to Day 170). Comparison of Kaplan-Meier estimates of time to breakthrough overt HE between groups showed a protective effect of rifaximin (p<0.0001). These data show that rifaximin treatment resulted in a 57.9% reduction, when compared with placebo, in the risk of experiencing breakthrough overt HE during the course of this study. Rifaximin treatment results in fewer overt HE episodes that may otherwise incapacitate the patient, may alleviate the burden on family members who are required to care for the patient, and reduces the burden of hospitalization in this patient population and the health-care system.

To investigate the potential effect of prognostic factors on breakthrough overt HE episode, the following prognostic factors were examined:
  Sex (male vs. female);
  Age;
  Race (white vs. non-white);
  Analysis Region (North American vs. Russia);
  MELD Level;
  Conn Score (0 vs. 1);
  Diabetes at Baseline (Yes vs. No);
  Duration of current verified remission; and
  Number of HE Episodes within the past 6 months prior to randomization.

Strong independent predictors of breakthrough overt HE episodes were the baseline age (p=0.0160), MELD score (p=0.0003), duration of current verified remission (p=0.1089), and number of prior HE episodes (p=0.0022).

These data show that rifaximin treatment, after adjusting for significant prognostic factors, resulted in a 60% reduction, when compared with placebo, in the risk of experiencing a breakthrough overt HE episode during the course of this study. The most influential prognostic factors were age (p=0.0315) and baseline MELD score (p=0.0003).

The results indicate that the highly significant protective effect of rifaximin (p<0.0001) against breakthrough overt HE episodes was maintained in the presence of statistically significant competing factors.

In the second study, median exposures were 253 days (range: 7 to 680) in the new rifaximin group (subjects who received placebo in the first study or subjects who did not participate in the first study), 265.5 days (range: 10 to 673) in the continuing rifaximin group (subjects who received rifaximin in the first study and the second study), and 255 days (range: 7 to 680) in the all rifaximin group (all subjects who received rifaximin in the second study In subjects who took rifaximin for up to 680 days (1.9 years), breakthrough overt HE episodes during the treatment period were experienced by 72 of 266 subjects (27.1%) overall: 54 of 196 subjects (27.6%) in the new rifaximin group and 18 of 70 subjects (25.7%) in the continuing rifaximin group. FIG. 2 compares subjects who participated in the double-blind, randomized the first study with new rifaximin subjects in the long-term, open-label study, the second study.

The Kaplan-Meier estimates of time to first breakthrough overt HE episode were similar between the rifaximin group in the first study and new rifaximin subjects in the second study. Also, similar proportions of subjects had breakthrough overt HE in the rifaximin group of the first study (22%, 31 of 140 [rifaximin group]) and in the new rifaximin group of the second study (27.6%, 54 of 196). Adjusted for exposure, rates of breakthrough HE episodes were 0.62 events/PEY in the rifaximin group from the first study compared to 0.38 events/PEY for new rifaximin subjects in the second study. These data demonstrate that protection against breakthrough overt HE in subjects who received rifaximin was consistent between the 2 studies.

Figure 7:
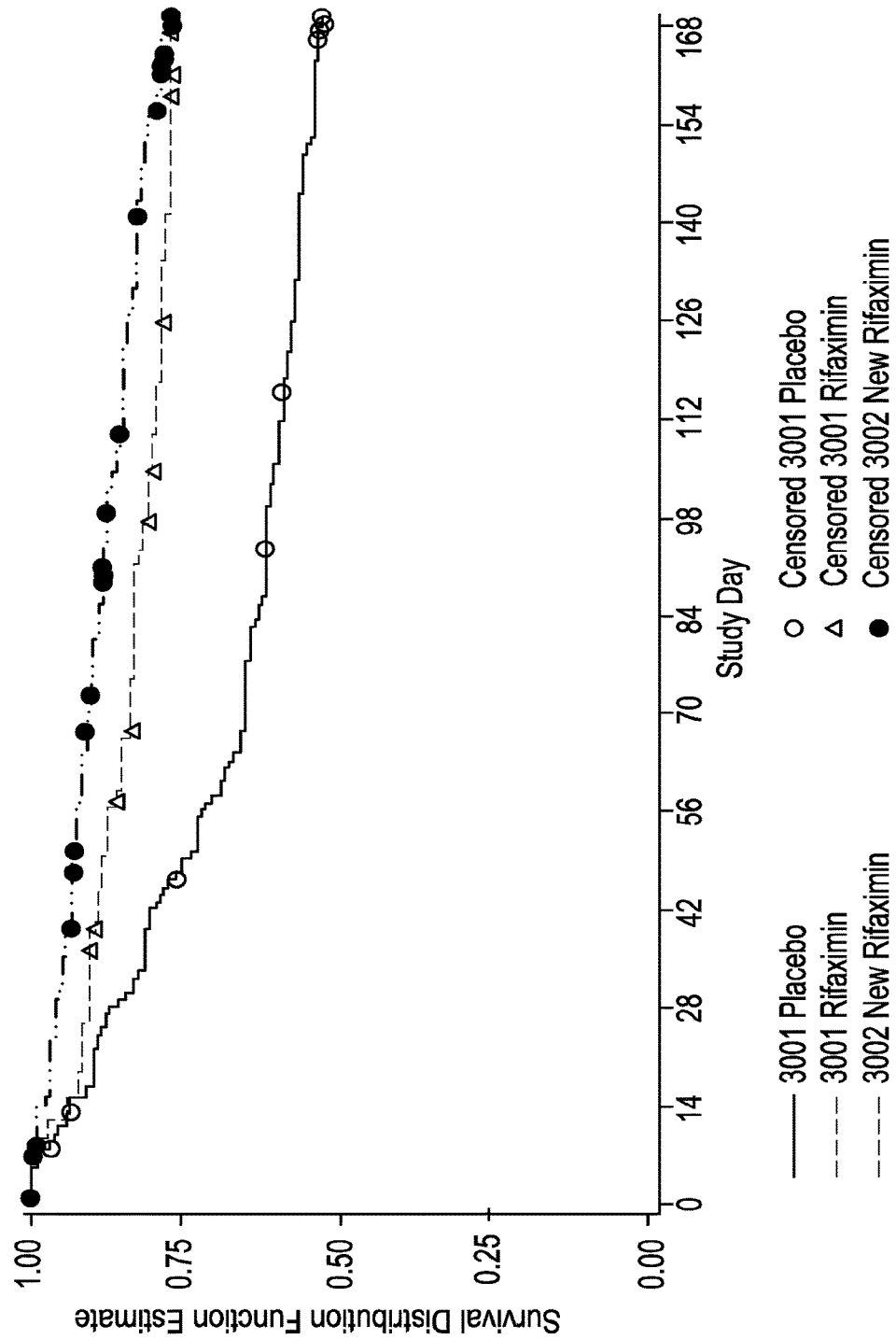
FIG. 7 is a comparison of time to first breakthrough overt HE episode in the first study (rifaximin versus placebo groups) and the second study (new to rifaximin group).

Note for FIG. 7, the survival distribution estimate on y-axis represents the proportion of subjects without breakthrough overt HE.

The first study data on time to first breakthrough overt HE episode are shown for the rifaximin group (small dashes) and the placebo group (straight line). The second study data on time to first breakthrough overt HE episode in the new rifaximin group are shown in large dashes.

Figure 8:
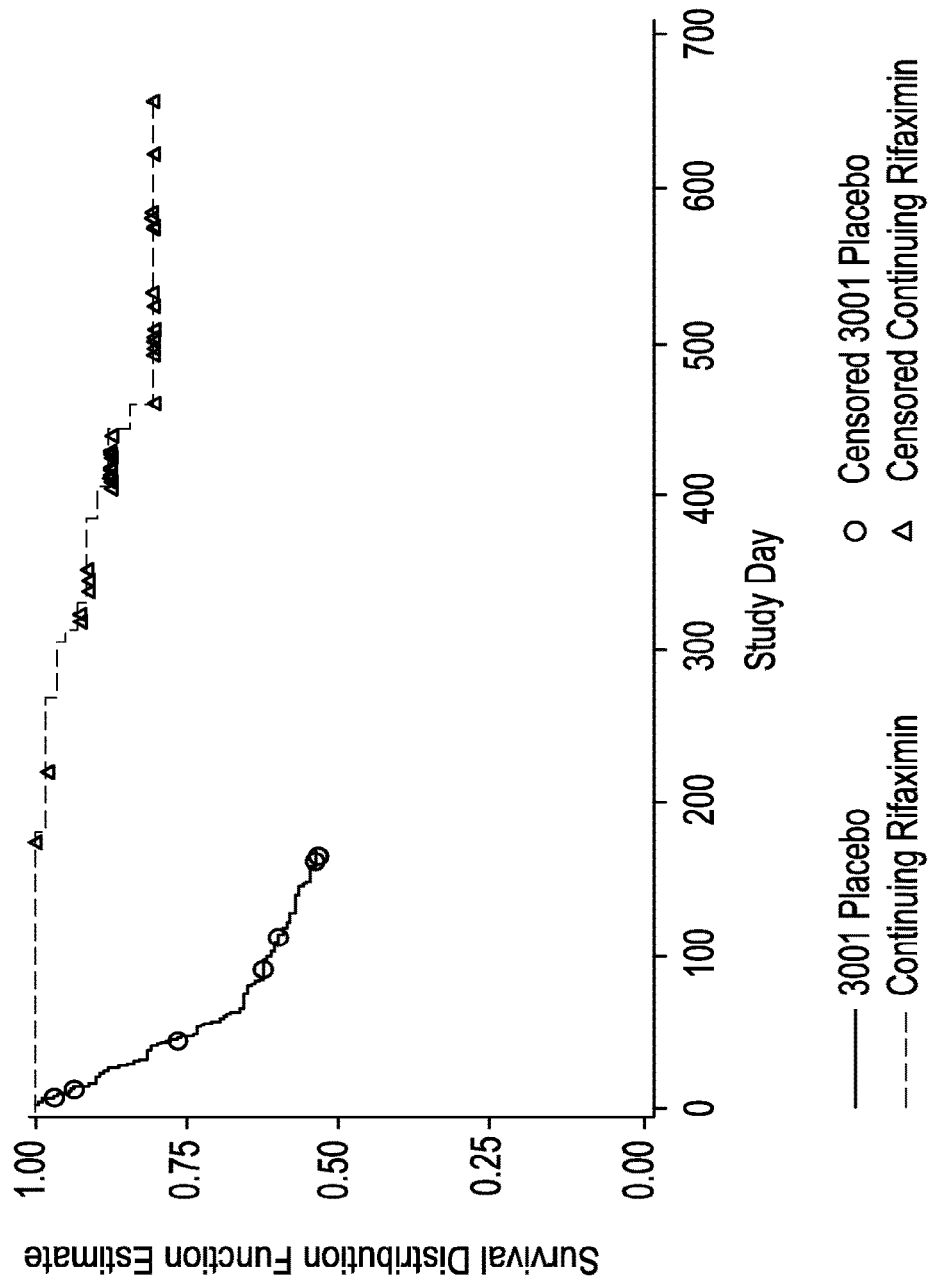
FIG. 8 depicts a comparison of time to first breakthrough over the episode during placebo experience (the first study) and after crossover to rifaximin experience (the second study) among the first study placebo subjects who started rifaximin in the second study.

In FIG. 8, the first study placebo subjects were followed after they crossed over to rifaximin therapy in the second study. Breakthrough overt HE was experienced by 15 of 82 during rifaximin treatment versus 39 of 82 during placebo treatment. A striking protective effect of rifaximin was observed in the comparison of Kaplan-Meier estimates of time to first breakthrough overt HE between placebo experience in the first study and rifaximin experience in the second study. The hazard ratio of rifaximin to placebo was 0.302 (95% CI: 0.166 to 0.549, p<0.0001 for between group difference in relative risk). This result represents 70% reduction in risk of experiencing breakthrough overt HE during rifaximin treatment in the second study when compared with their prior placebo experience in the first study.

Note for FIG. 8, the survival distribution estimate on y-axis represents the proportion of subjects without breakthrough overt HE. the first study data on time to first breakthrough overt HE episode are shown in the left panel for the placebo group. The right panel shows time to first breakthrough overt HE in the second study among the first study placebo subjects (n=82) who crossed over to rifaximin therapy in the second study. The vertical line between the left and right panels marks the end of the double-blind study and start of the open-label study.

Figure 9:
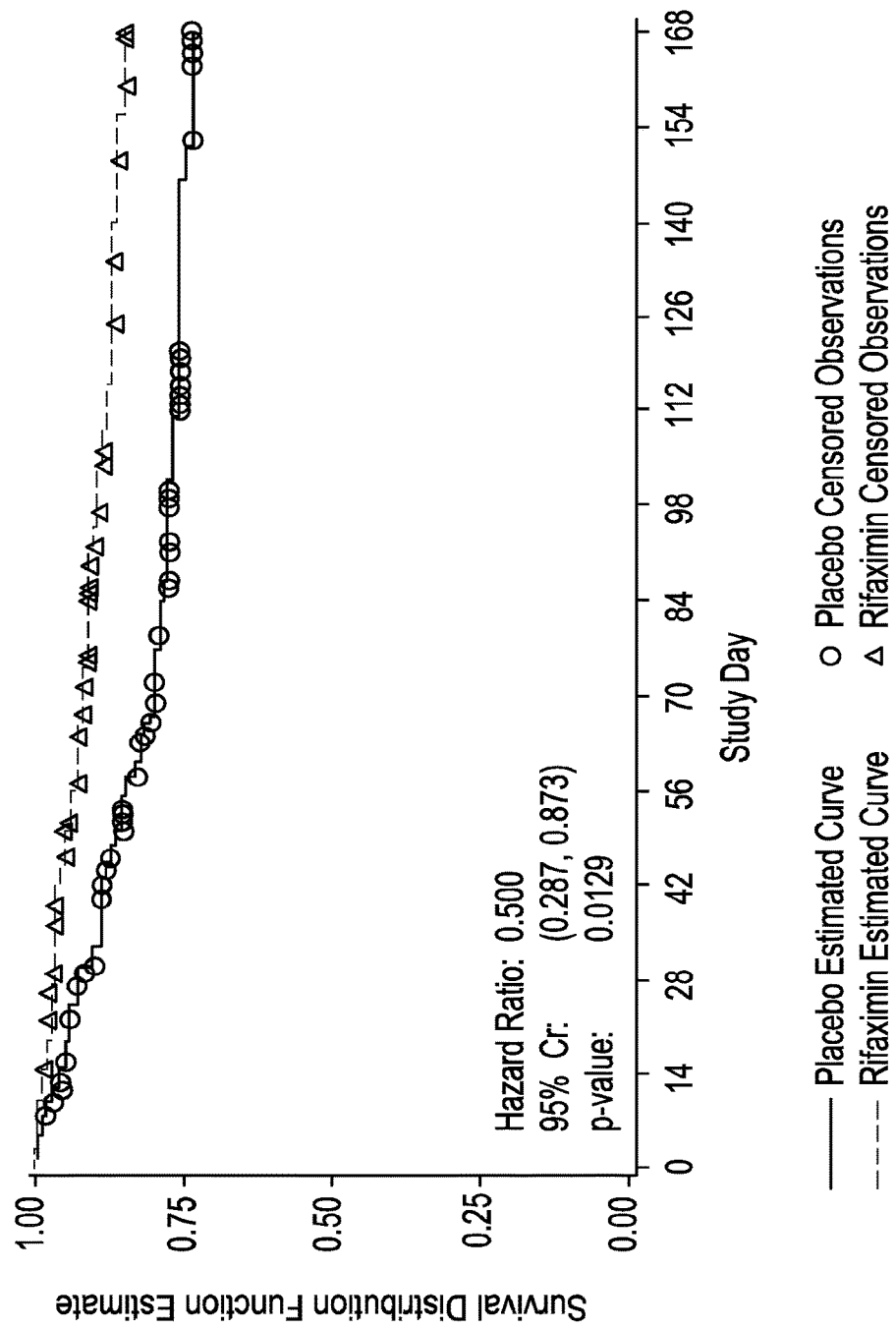
FIG. 9 depicts the time to first HE-related hospitalization (up to 6 months of treatment, day 170, in the first study).

FIG. 9 illustrates time to first HE-related hospitalization (e.g., hospitalization directly resulting from HE or hospitalization caused by HE) by treatment group in the ITT population in the first study. Table 19 presents estimates of the proportions of subjects who had their first HE-related hospitalization over the course of the Treatment Period and results of statistical analyses. Subjects who discontinued prior to hospitalization due to HE and prior to completion of the 6-month treatment period were censored at the time of discontinuation. Hepatic encephalopathy-related hospitalizations were reported for 19 of 140 subjects and 36 of 159 subjects in the rifaximin and placebo groups, respectively. Rifaximin had a protective effect against HE-related hospitalization during the 6-month treatment period; hazard ratio in the rifaximin group relative to placebo was 0.500 (95% CI: 0.287 to 0.873) (p=0.0129) for the risk of HE-related hospitalization. This hazard ratio represents a 50% reduction, when compared with placebo, in the risk of hospitalization due to HE during the 6-month treatment period. Consistent with these results, the HE-related hospitalization rate was 51% lower (0.38 event/PEY, rifaximin versus 0.78 event/PEY, placebo) in the rifaximin group in the first study, after normalization to exposure.

Note for FIG. 9, the survival distribution estimate on y-axis represents the proportion of subjects without HE-related hospitalization. Dashed line represents rifaximin group and solid line represents placebo group. Open circles and open triangles represent censored subjects. Subjects who discontinued prior to hospitalization due to HE and prior to completion of the 6-month treatment period were censored at the time of discontinuation. Hepatic encephalopathy-related hospitalization was recorded on the HE-related hospitalization CRF.

TABLE 19

The First Study: Kaplan-Meier Estimates and Statistical Analyses of Time to First HE-Related Hospitalization (up to 6 Months of Treatment, Day 170) (ITT Population)

| | Placebo (N = 159) | | | | | Rifaximin (N = 140) | | | | |
| --- | --- | --- | --- | --- | --- | --- | --- | --- | --- | --- |
| Treatment interval (days) | At Risk[a] | Number of events[b] | Cumulative number of events | Event probability (SE)[c] | Probability of no HE-related hospitalization[d] | At Risk[a] | Number of events[b] | Cumulative number of events | Event probability (SE)[c] | Probability of no HE-related hospitalization[d] |
| 0 to <28 | 155 | 11 | 11 | 0.07 (0.02) | 1.0000 | 139 | 4 | 4 | 0.03 (0.01) | 1.0000 |
| 28 to <56 | 132 | 12 | 23 | 0.09 (0.03) | 0.9288 | 130 | 4 | 8 | 0.03 (0.02) | 0.9711 |
| 56 to <84 | 108 | 7 | 30 | 0.06 (0.02) | 0.8440 | 119 | 4 | 12 | 0.03 (0.02) | 0.9411 |
| 84 to <140 | 88 | 4 | 34 | 0.05 (0.02) | 0.7893 | 106 | 5 | 17 | 0.05 (0.02) | 0.0904 |
| 140 to <168 | 72 | 2 | 36 | 0.03 (0.02) | 0.7535 | 92 | 2 | 19 | 0.02 (0.02) | 0.8665 |
| ≥168 | 34 | 0 | 36 | 0 | 0.7525 | 43 | 0 | 19 | 0 | 0.8475 |

Abbreviations:
CI = confidence interval;
SE = standard error.
[a]Number of subjects at risk during the treatment interval, estimated using the life table method. Assuming that censored cases were at risk for half of the interval, they only counted for half in figuring the number at risk.
[b]Number of events occurring during the treatment interval.
[c]Estimate of the probability of experiencing HE-related hospitalization during the treatment interval. Standard error (SE) estimated by using Greenwood's formula.
[d]Estimate of the probability of no HE-related hospitalization until at least the beginning of the next treatment interval.
[e] Hazard ratio estimate (hazard of HE-related hospitalization in the rifaximin group compared with the placebo group) determined from the Cox proportional hazards model. P-value based on the Score statistic.

The effect of rifaximin therapy on HE-caused hospitalizations (e.g., hospitalization directly resulting from HE only) was also determined. FIG. 5 illustrates time to first HE-caused hospitalizations by treatment group in the first study.

Hepatic encephalopathy-caused hospitalizations were reported for 15 of 140 subjects and 33 of 159 subjects in the rifaximin and placebo groups, respectively. Rifaximin had a significant protective effect against HE-caused hospitalization during the 6-month treatment period; hazard ratio in the rifaximin group relative to placebo was 0.438 (95% CI: 0.238 to 0.807) (p=0.0064) for the risk of HE-caused hospitalization. Subjects in the rifaximin group had a 56% reduction in the risk of hospitalization due to HE during the 6-month treatment period when compared with placebo. The HE-caused hospitalization rate was 0.30 events/PEY in the rifaximin group versus 0.72 event/PEY in the placebo group.

Figure 10:
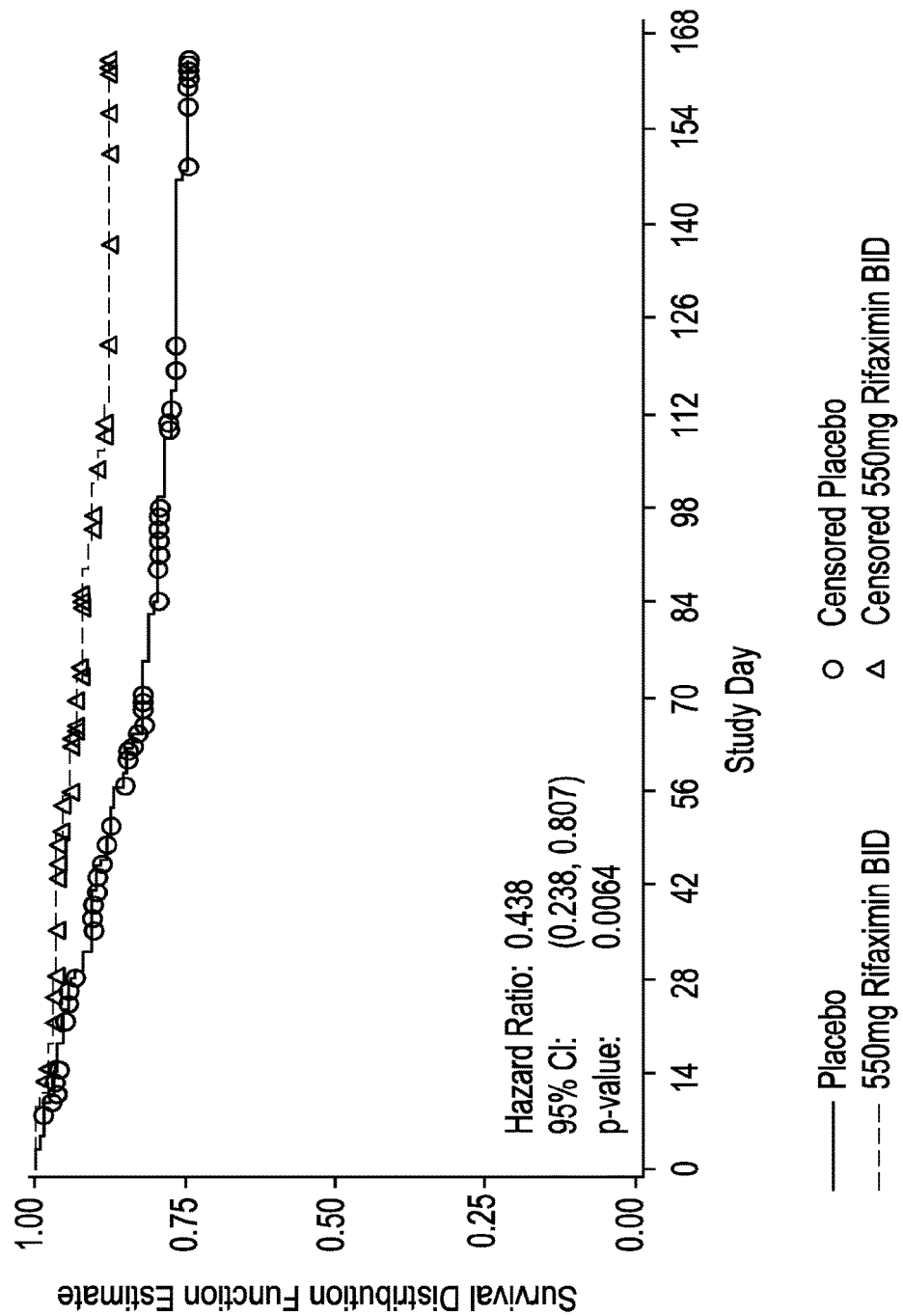
FIG. 10 depicts the time to first HE-caused hospitalization in the first study (ITT population).

Note for FIG. 10, the survival distribution estimate on y-axis represents the proportion of subjects without HE-caused hospitalizations. Dashed line represents rifaximin group and solid line represents placebo group. Open circles and open triangles represent censored subjects. Subjects who discontinued prior to hospitalization were censored at the time of discontinuation.

The effect of rifaximin therapy on all-cause hospitalizations was also determined. In the double-blind the first study, 46 of 140 rifaximin subjects and 60 of 159 placebo subjects were hospitalized due to any SAE. The risk of all-cause hospitalization was reduced by 30% in the rifaximin group when compared to placebo (p=0.0793 for between-group difference in relative risk). The all-cause hospitalization rate was 0.92 events/PEY in the rifaximin group versus 1.31 event/PEY in the placebo group. These data demonstrated that rifaximin treatment reduced the burden of HE-related/caused hospitalization when compared to placebo treatment in the first study. Also, a low HE-related/caused hospitalization rate was consistently observed during rifaximin therapy in the first study (0.38 event/PEY) and in the second study (0.29 event/PEY), at least partly as a result of maintaining remission from demonstrated HE in subjects with end-stage liver disease.

Figure 11:
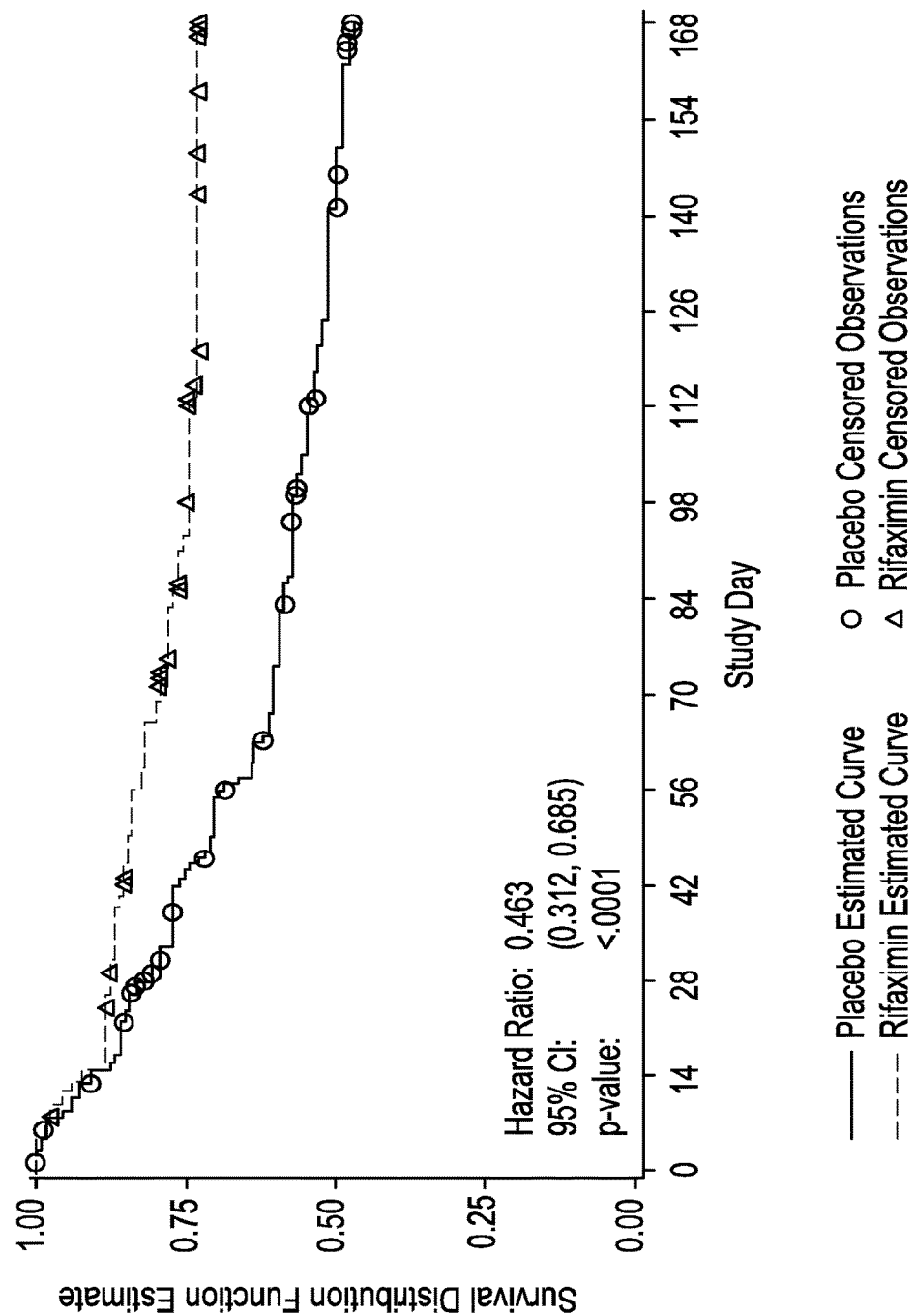
FIG. 11 depicts the time to First Increase in Conn Score (up to 6 months of treatment, day 170, the first study) (ITT Population).

FIG. 11 illustrates time to any increase from baseline in Conn score by treatment group in the ITT population. Table 20 presents estimates of the proportions of subjects who had any increase in Conn score over the course of the Treatment Period and results of statistical analyses. Subjects who discontinued prior to experiencing an increase in Conn score and prior to completion of the 6-month treatment period were censored at the time of discontinuation. By evaluating the time to any increase from baseline in Conn score, it was possible to compare the earliest worsening in mental status between subjects in the rifaximin and placebo treatment groups, even if the worsening did not reach the definition of breakthrough HE (eg, increase inConn score from 0 to 1). Increases in Conn score were reported for 37 of 140 subjects and 77 of 159 subjects in the rifaximin and placebo groups, respectively. A highly significant protective effect of rifaximin was observed; hazard ratio in the rifaximin group relative to placebo was 0.463 (95% CI: 0.312 to 0.685) (p<0.0001) for the risk of experiencing an increase in Conn score (e.g., worsening in mental status) during the 6-month treatment period.

TABLE 20

The First Study: Kaplan-Meier Estimates and Statistical Analyses of Time to First Increase in Conn Score (up to 6 Months of Treatment, Day 170) (ITT Population)

| | Placebo (N = 159) | | | | | Rifaximin (N = 140) | | | | |
|---|---|---|---|---|---|---|---|---|---|---|
| Treatment interval (days) | At Risk[a] | Number of events[b] | Cumulative number of events | Event probability (SE)[c] | Probability of no increase in Conn score[d] | At Risk[a] | Number of events[b] | Cumulative number of events | Event probability (SE)[c] | Probability of no increase in Conn score[d] |
| 0 to <28 | 156 | 26 | 26 | 0.17 (0.03) | 1.0000 | 139 | 17 | 17 | 0.012 (0.03) | 1.0000 |
| 28 to <56 | 125 | 21 | 47 | 0.17 (0.03) | 0.8333 | 119 | 5 | 22 | 0.04 (0.02) | 0.8777 |
| 56 to <84 | 100 | 15 | 62 | 0.15 (0.04) | 0.6928 | 109 | 9 | 31 | 0.08 (0.03) | 0.8407 |
| 84 to <140 | 80 | 10 | 72 | 0.13 (0.04) | 0.5883 | 94 | 5 | 36 | 0.05 (0.02) | 0.7713 |
| 140 to <168 | 62 | 5 | 77 | 0.08 (0.03) | 0.5143 | 79 | 0 | 36 | 0 | 0.7302 |
| ≥168 | 27 | 0 | 77 | 0 | 0.4729 | 37 | 1 | 37 | 0.03 (0.03) | 0.7302 |

Abbreviations:
CI = confidence interval;
SE = standard error.
[a]Number of subjects at risk during the treatment interval, estimated using the life table method.
[b]Number of events occurring during the treatment interval. Assuming that censored cases were at risk for half of the interval, they only counted for half in figuring the number at risk.
[c]Kaplan-Meier estimate of the probability of experiencing an increase in Conn score during the treatment interval. Standard error (SE) estimated by using Greenwood's formula.
[d]Estimate of the probability of no increase in Conn score until at least the beginning of the next treatment interval.
[e] Hazard ratio estimate (hazard of experiencing an increase in Conn score in the rifaximin group compared with the placebo group) determined from the Cox proportional hazards model. P-value based on the Score statistic.

Figure 12:
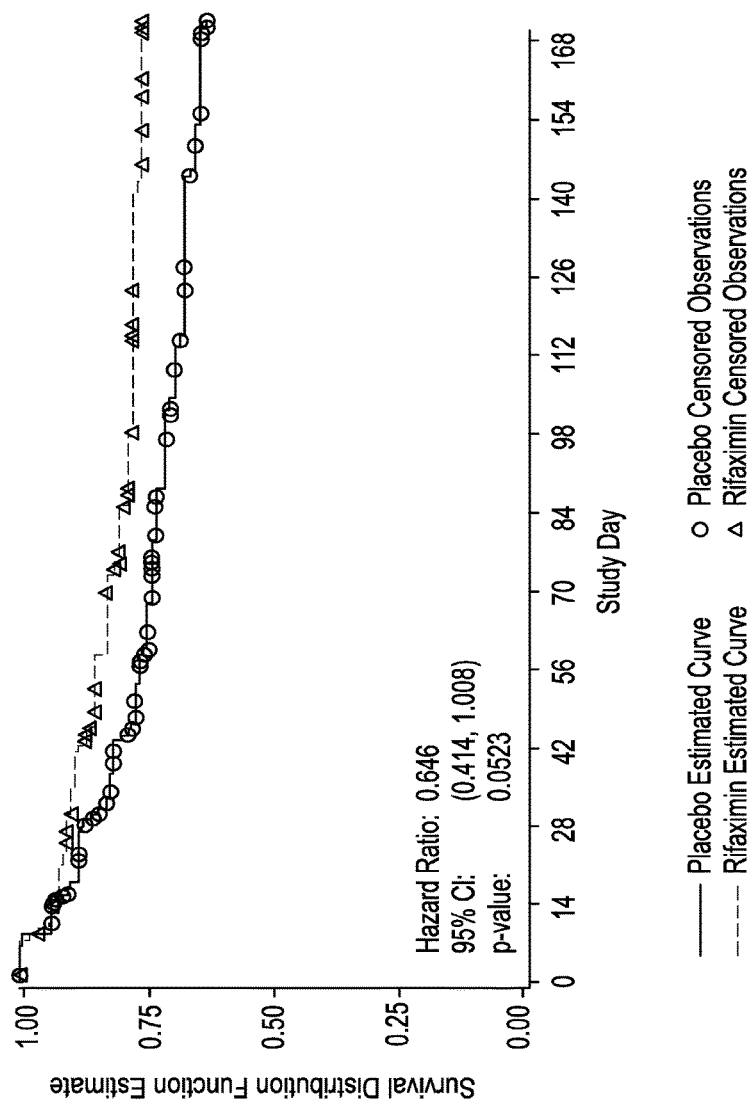
FIG. 12 depicts the time to first Increase in asterixis grade (up to 6 months of treatment, day 170, the first study) (ITT Population).

FIG. 12 illustrates time to any increase from baseline in asterixis grade by treatment group in the ITT population in the first study. Table 21 presents estimates of the proportions of subjects who had any increase in asterixis grade over the course of the Treatment Period and results of statistical analyses. Subjects who discontinued prior to experiencing an increase in asterixis grade and prior to completion of the 6-month treatment period were censored at the time of discontinuation.

By evaluating the time to any increase from baseline in asterixis grade, it was possible to compare the earliest worsening in neuromotor functioning between subjects in the rifaximin and placebo treatment groups. Increases in asterixis grade were reported for 32 of 140 subjects and 50 of 159 subjects in the rifaximin and placebo groups, respectively. A protective effect of rifaximin against an increase in asterixis grade (e.g., worsening in neuromotor functioning) was observed that showed a trend toward statistical significance; hazard ratio in the rifaximin group relative to placebo was 0.646 (95% CI: 0.414 to 1.008) (p=0.0523) for the risk of experiencing an increase in asterixis grade during the 6-month treatment period.

clinical evaluation of Conn score (or a combination of Conn score and asterixis grade), thereby underscoring the reliability and clinical relevance of the primary efficacy measure. The significant correlation of the primary efficacy endpoint to a venous ammonia levels demonstrates the reliability and clinical relevance of the primary efficacy measure in the first study.

TABLE 21

The First Study: Kaplan-Meier Estimates and Statistical Analyses of Time to First Increase in Asterixis Grade (up to 6 Months of Treatment, Day 170) (ITT Population)

| | Placebo (N = 159) | | | | | Rifaximin (N = 140) | | | | |
|---|---|---|---|---|---|---|---|---|---|---|
| Treatment interval (days) | At Risk[a] | Number of events[b] | Cumulative number of events | Event probability (SE)[c] | Probability of no increase in asterixis grade[d] | At Risk[a] | Number of events[b] | Cumulative number of events | Event probability (SE)[c] | Probability of no increase in asterixis grade[d] |
| 0 to <28 | 154 | 20 | 20 | 0.13 (0.03) | 1.0000 | 137 | 13 | 13 | 0.10 (0.03) | 1.0000 |
| 28 to <56 | 120 | 15 | 35 | 0.13 (0.03) | 0.8697 | 116 | 7 | 20 | 0.06 (0.02) | 0.9048 |
| 56 to <84 | 91 | 4 | 39 | 0.04 (0.02) | 0.7610 | 101 | 7 | 27 | 0.07 (0.03) | 0.8499 |
| 84 to <140 | 76 | 6 | 45 | 0.08 (0.03) | 0.7275 | 87 | 3 | 30 | 0.03 (0.02) | 0.7910 |
| 140 to <168 | 61 | 4 | 49 | 0.07 (0.03) | 0.6701 | 74 | 1 | 31 | 0.01 (0.01) | 0.7637 |
| ≥168 | 27 | 1 | 50 | 0.04 (0.04) | 0.6262 | 34 | 1 | 32 | 0.03 (0.03) | 0.7534 |

Abbreviations:
CI = confidence interval;
SE = standard error.
[a]Number of subjects at risk during the treatment interval, estimated using the life table method. Assuming that censored cases were at risk for half of the interval, they only counted for half in figuring the number at risk.
[b]Number of events occurring during the treatment interval.
[c]Estimate of the probability of experiencing an increase in asterixis grade during the treatment interval. Standard error (SE) estimated by using Greenwood's formula.
[d]Estimate of the probability of no increase in asterixis grade until at least the beginning of the next treatment interval.
[e] Hazard ratio estimate (hazard of experiencing an increase in asterixis grade in the rifaximin group compared with the placebo group) determined from the Cox proportional hazards model. P-value based on the Score statistic.

Subjects ranked their level of fatigue by using a 7-point scale from the worst response (1, high degree of fatigue) the best response (7, minimal fatigue). Minimal differences between placebo and rifaximin groups were observed in the changes from baseline in CLDQ fatigue scores. Mean (SD) fatigue scores were 3.34 (1.406) versus 3.28 (1.326) at baseline and 3.51 (1.529) versus 3.57 (1.527) in the placebo and rifaximin groups, respectively. Because of altered mental and neuromotor status, it was not possible for subjects to complete the CLDQ assessment during an overt HE breakthrough episode.

Table 22 summarizes changes from baseline to end of treatment in venous ammonia level by treatment group in the first study.

In the first study, venous ammonia levels were highly variable over the course of the study. However, subjects in the rifaximin group had significantly greater reductions in venous ammonia levels when compared to placebo-treated subjects (p=0.0391). Venous ammonia levels, a quantitative assessment that is associated with the CNS effects underlying overt HE, was shown to be highly predictive of the occurrence of breakthrough overt HE as determined by the

TABLE 22

The First Study: Mean (SD) Changes from Baseline in Venous Ammonia Level by Treatment Group (ITT Population)

| | Placebo N = 159 (μg/dL) | Placebo N = 140 (μg/dL) |
|---|---|---|
| Baseline | n = 146 | n = 132 |
| Mean (SD) ammonia level | 90.3 (52.48) | 87.9 (47.76) |
| End of treatment | n = 141 | n = 132 |
| Mean (SD) ammonia level | 88.4 (45.75) | 83.9 (45.02) |
| Change from baseline to end of treatment | n = 131 | n = 125 |
| Mean (SD) change in ammonia level | −0.3 (58.13) | −5.7 (46.77) |

Note:
Baseline value was the last available value prior to first dose of study drug, and end of treatment value was the last available post-baseline value during the treatment period.

The Second Study

In the second study, Conn scores were generally maintained or improved with rifaximin use up to 18 months. At the last visit, 70.7% of subjects (188 of 266 subjects) had no change and 20.3% (54 of 266) had improvements in Conn scores compared with baseline, indicating that mental status was maintained or improved in the majority of subjects (91%) over the treatment period. Like Conn scores, asterixis grades were generally maintained or improved with rifaximin use up to 18 months. At the last visit, 77.1% of subjects (205 of 266 subjects) had no change and 16.2% (43 of 266) had improvements in asterixis scores compared with baseline, indicating that neuromotor symptoms associated with increasing neurological impairment were maintained in 83.3% of subjects over the treatment period. The last visit for the second study is the last visit recorded for the interim analysis.

Maintenance or improvement in Conn scores were observed for >85% of subjects during rifaximin treatment for up to 840 days; mean (±SD) exposure for all rifaximin experience was 273.8 (160.92) days (exposure results are present in detail in the ISS, Module 5.3.5.3.2). A total of 65.5% of subjects (220 of 337) had no change in Conn score and 21.1% (71 of 337) had improvements in Conn score from baseline to last visit. Similarly, maintenance or improvements in asterixis grades were observed for >90% of subjects during rifaximin treatment. No change from baseline in asterixis grade was reported for 75.2% of subjects (252 of 337), and 17.3% had improvements.

Of the 118 subjects who entered the study with a Conn score of ≥1, e.g., those subjects for whom improvement was possible, 62.2% (71 of 118) showed an improvement from baseline to Conn score 0 at last assessment. Also, of the 99 subjects who entered with an asterixis grade of ≥1, ie those subjects for whom improvement in asterixis grade was possible, 58.6% (58 of 99) showed improvement in asterixis grade from baseline to end of study.

Changes from baseline in Conn scores and asterixis grades to last visit were similar among new rifaximin subjects in the second study (e.g., started rifaximin in 3002), continuing rifaximin subjects (e.g., received rifaximin in the first study and in the second study), and all rifaximin experience subjects (e.g., received rifaximin in the first study or in the second study).

These results support those from the first study, in which treatment with rifaximin was significantly more effective than placebo in the prevention of worsening of Conn score (2.46 times versus placebo, p<0.0001) and in the prevention of worsening of asterixis grade (1.92 times versus placebo, p=0.0262).

Changes from baseline in CFF results (the first study) Increases in CFF results represent improvement in neurological function in patients with HE. Subjects in the rifaximin group had significantly greater increases in CFF results from baseline to end of treatment when compared with placebo (Table 23). Mean changes (±SD) in CFF results were 0.945 (±4.75) in the rifaximin group versus 0.355 (±4.70) in the placebo group (p=0.0320 for between-group difference).

Similar to the correlation for venous ammonia levels, there was a strong correlation between the quantitative assessment of CFF results and the occurrence of breakthrough overt HE.

TABLE 23

Mean (SD) Changes from Baseline in CFF Test Results by Treatment Group (ITT Population)

|  | Placebo N = 159 (Hz) | Rifaximin N = 140 (Hz) |
| --- | --- | --- |
| Baseline | n = 159 | n = 140 |
| Mean (SD) CFF result | 37.41 (6.03) | 36.90 (5.47) |
| End of treatment | n = 155 | n = 139 |
| Mean (SD) CFF result | 37.60 (5.98) | 37.81 (4.88) |
| Change from baseline to end of treatment | n = 155 | n = 139 |
| Mean (SD) change in CFF result | 0.355 (4.70) | 0.945 (4.75) |

Note:
Baseline value was the last available value prior to first dose of study drug, and end of treatment value was the last available post-baseline value during the treatment period.

A retrospective chart review was performed for 145 patients with HE who received lactulose 30 mL twice daily for ≥6 months followed by treatment with rifaximin 400 mg 3 times/day for ≥6 months. Dramatic differences were observed in favor of rifaximin treatment. Compliance of ≥75% was significantly better during rifaximin treatment than during lactulose treatment; 92% versus 31% of patients received ≥75% of scheduled rifaximin and lactulose doses, respectively. Total number of hospitalizations, duration of hospitalizations, HE endpoints, and cost of therapy were compared between the 2 treatment regimens. Significantly fewer hospitalizations (0.5 versus 1.6) and days hospitalized (2.5 versus 7.3 days) were reported for rifaximin treatment versus lactulose treatment (p<0.001), and hospitalization charges per patient were $14,222 compared with $56,635 during rifaximin and lactulose treatments, respectively.

With respect to HE endpoints at the end of the treatment periods, asterixis was reported for 63% (rifaximin) versus 93% (lactulose) of patients (p<0.001), and Conn scores of 3 or 4 were observed for 6% (rifaximin) versus 25% (lactulose) (p<0.001). In addition, significantly more patients had diarrhea, flatulence, and abdominal pain during lactulose therapy than during rifaximin therapy (p<0.001).

Hospitalizations and cost of therapy were analyzed in a chart review of 39 liver transplant patients who presented with HE Conn scores of 2 during the interval from January 2004 to November 2005. Twenty-four patients were treated with lactulose and 15 were treated with rifaximin. Nineteen hospitalizations were reported for the lactulose group and 3 hospitalizations for the rifaximin group. The average length of stay was significantly shorter in the rifaximin group than in the lactulose group (3.5 days [range, 3-4] versus 5.0 days [range, 3 to 10] [p<0.001]). The average annual total cost of treatment (hospitalization, emergency room visit, and drug cost) per patient was $7958 for the rifaximin group and $13,285 for the lactulose group. Although the cost of rifaximin was substantially higher than the cost of lactulose, total cost of treatment (hospitalization plus drug cost) was 1.67-fold higher in patients who were treated with lactulose.

Durability of Rifaximin Treatment Effect

Data from the second study provide information on the long-term durability of rifaximin for the protection against breakthrough overt HE episodes. Rifaximin treated subjects from the first study who were in remission at the end of the first study (6 months treatment) were followed during open-label study the second study (n=60). Time to first breakthrough HE episode is shown for the rifaximin rollover subjects (the first study plus the second study) and the first study placebo subjects in FIG. 15. The incidence of breakthrough overt HE in these rollover rifaximin subjects was compared to placebo subjects in the first study. The incidence of breakthrough HE episode for rifaximin subjects was dramatically lower than the first study placebo group (ratio of rollover rifaximin to placebo was 0.0797 after adjusting for exposure time, p<0.0001 for difference between rifaximin and placebo.

These results demonstrated that rifaximin had a durable protective effect beginning in the first study and continuing in the second study (median exposures to rifaximin were 168 days in the first study and 253 days in the second study).

Note for FIG. 13, the survival distribution estimate on y-axis represents the proportion of subjects without breakthrough overt HE. Dashed lines represents rifaximin treated subjects from the first study who were in remission at the end of the first study (6 months treatment) and were followed during open-label study the second study (n=60), and solid line represents the placebo group in the first study. The vertical line marks the end of the double-blind study and start of the open-label study. Open circles represent censored subjects in the first study placebo group and open triangles represent censored subjects in the continuing rifaximin group. Subjects who discontinued prior to the first breakthrough overt HE episode were censored at the time of discontinuation.

Unlike the first study, in which subjects were discontinued from the study after experiencing their first breakthrough overt HE episode, subjects had the option of continuing rifaximin therapy in the second study after experiencing breakthrough overt HE. Therefore, the incidence of breakthrough overt HE over time during rifaximin therapy was evaluated. Table 24 presents breakthrough overt HE episodes by total number of HE episodes during the course of the study.

In the all rifaximin group, 27.1% of subjects (72 of 266) had ≥1 breakthrough overt HE episode. Of the 72 subjects with breakthrough HE, most had 1 (44 subjects) or 2 (18 subjects) episodes. Ten subjects had 3 or more breakthrough HE episodes in the second study.

TABLE 24 the second study: Breakthrough Overt HE Episodes by Number of Repeat Episodes

|  | New Rifaximin N = 196 n (%) | Continuing Rifaximin N = 70 n (%) | All Rifaximin N = 266 n (%) |
|---|---|---|---|
| Subjects with ≥1 breakthrough overt HE episode | 54 (27.6) | 18 (25.7) | 72 (27.1) |
| Total number of HE episodes[a] during the study: | | | |
| 1 | 34 (17.3) | 10 (14.3) | 44 (16.5) |
| 2 | 12 (6.1) | 6 (8.6) | 18 (6.8) |
| 3 | 4 (2.0) | 0 | 4 (1.5) |
| 4 | 1 (0.5) | 1 (1.4) | 2 (0.8) |
| 5 | 1 (0.5) | 0 | 1 (0.4) |
| 6 | 0 | 1 (1.4) | 1 (0.4) |
| 10 | 2 (1.0) | 0 | 2 (0.8) |

Abbreviation:
HE = hepatic encephalopathy
[a]Number of HE episodes. Subjects were counted only once for each number of overt HE episodes. For example, if a subject experienced 3 episodes, he/she was included in the row showing 3 episodes only, and was not also counted in the rows for 2 and 1 episodes.

Effect of Rifaximin on the Incidence of Overt HE Episodes (HE Burden)

The effect of rifaximin therapy on the incidence of overt HE episodes (e.g., burden of HE), the numbers of HE episodes in the first study or the second study were compared to the numbers of HE episodes in the absence of rifaximin therapy. The 6-month interval prior to the first study or the 12-month interval prior to the second study was compared against rifaximin therapy in either study. The time of participation in the first study did not reflect experience in the absence of rifaximin therapy, therefore, for subjects who rolled over to the second study without an HE episode in the first study, the 12-month interval prior to the second study was used for comparison. Most subjects in the second study (152 of 266) were also in the first study. Overt HE episodes in the second study were combined with the first study because, unlike the first study, subjects in the second study had the option of remaining on rifaximin after experiencing their first breakthrough HE episode. The numbers of overt HE episodes experienced during the 6-month or 12-month intervals prior to the first study or prior to the second study were known. While 30.8% of subjects had >2 HE episodes during the 6-month or 12-month interval prior to rifaximin therapy, only 3.6% of subjects had >2 HE episodes during rifaximin therapy for up to 840 days (median exposure=253 days [~8 months]) in the first study plus the second study. This difference in the incidence of HE episodes while subjects were receiving rifaximin when compared to the absence of rifaximin therapy suggests a strong effect of rifaximin in relieving the burden of overt HE episodes in patients with recurrent, overt HE associated severe liver disease.

Hepatic encephalopathy is a serious, rare, complex, episodic, neuropsychiatric syndrome associated with advanced liver disease. Hepatic encephalopathy is a formidable burden on the patient, his/her family, and the healthcare system. Overt HE episodes are debilitating, render the patient incapable of self-care, and frequently result in hospitalization. Rifaximin has been granted orphan drug status for the HE indication because the disease is serious and chronically debilitating, and there is a low incidence of HE in the general population. Also, there is an unmet medical need for patients with HE because of limitations of the current standard of care.

Without wishing to be bound by any specific scientific theories, it is believed that the mechanism of action of rifaximin depends on the inhibition of DNA-dependent RNA polymerase of the target microorganisms, leading to the suppression of initiation of chain formation in RNA synthesis. Rifaximin has a lower rate of fecal eradication of pathogens compared with other commonly used antibacterial drugs and causes minimal alterations in gut flora suggesting that rifaximin has a different mechanism of action than other commonly used drugs in enteric bacterial infection, such as the fluoroquinolones. The antibacterial properties of rifaximin appear to result from bactericidal activity at rifaximin concentrations greater than or equal to the MIC, and from alterations in bacterial morphology and physiological functioning, which have been observed at sub-MIC concentrations.

It was unexpectedly discovered herein, that the risk of the development of antibiotic resistance is low during chronic treatment with rifaximin when compared to other systemic antibiotics such as neomycin. The low risk of antibiotic resistance during rifaximin therapy is likely due to the fact that resistance to rifaximin is not plasmid-mediated but instead requires a stable mutation in host cell DNA; therefore, dissemination of resistance and cross-resistance to other antibiotics by plasmid-based mechanisms are eliminated. Also, bacteria at sites outside of the GI tract are not exposed to appreciable selective pressure because of negligible systemic concentrations of rifaximin. Additionally, microbiological data from a study of patients with ulcerative colitis who were receiving high doses of rifaximin showed that rifaximin-resistant bacterial colonies generated during in vivo exposure to rifaximin were unstable and susceptibility returned after a brief period of treatment interruption.

Rifaximin treatment results in fewer overt HE episodes that may otherwise incapacitate the patient, may alleviate the burden on family members who are required to care for the patient, and reduces the burden of hospitalization in this patient population and the healthcare system. The following are results from the second study with respect to time to first breakthrough overt HE episode:

The protective effect was reproducible: the time to first breakthrough overt HE episode results were similar between the rifaximin group in the first study and new rifaximin subjects in the second study; and 22% and 27.6% had breakthrough overt HE in the first study rifaximin group and the second study new rifaximin group, respectively. Adjusted for exposure, rates of breakthrough HE episodes were 0.62 events/PEY in the rifaximin group from the first study compared to 0.38 events/PEY for new rifaximin subjects in the second study. These data demonstrate that protection against breakthrough overt HE in subjects who received rifaximin was consistent between the 2 studies. Additionally, when the first study placebo subjects crossed over to rifaximin therapy by entering the second study, a striking protective effect of rifaximin was observed in the comparison of Kaplan-Meier estimates of time to first breakthrough overt HE between placebo experience in the first study and rifaximin experience in the second study. The hazard ratio of rifaximin to placebo was 0.302 (95% CI: 0.166 to 0.549, p<0.0001 for between group difference in relative risk). This result represents 70% reduction in risk of experiencing breakthrough overt HE during rifaximin treatment in the second study when compared with their prior placebo experience in the first study. This reduction took place in spite of the aging and presumably progressing nature of the population with chronic liver disease.

The protective effect was durable: the Kaplan-Meier estimate of time-to-first breakthrough HE demonstrated long-term maintenance of remission from breakthrough HE when rifaximin subjects in remission after participation in the first study were followed in the second study (up to 680 days of rifaximin therapy; median exposure durations were 168 days in the first study and 253 days in the second study). The incidence of breakthrough HE episode for these rifaximin subjects relative to the first study placebo was dramatically low, an indication of fewer breakthrough HE episodes with rifaximin treatment (p<0.0001 for difference in relative risk between rifaximin and placebo).

Results for other efficacy endpoints also demonstrated statistically significant protective effects of rifaximin. In the first study, the analysis of time to first HE-related hospitalization (e.g., hospitalization directly resulting from HE or hospitalization complicated by HE) demonstrated that the reduction in risk of hospitalization due to HE was 50% in the rifaximin group, when compared with placebo, during the 6-month treatment period (p=0.0129 for between-group difference in relative risk). In the first study, the risk of HE-caused hospitalization (e.g., hospitalization directly resulting from HE only) was reduced by 56% (p=0.0064 for between-group difference in relative risk), and the risk of all-cause hospitalization was reduced by 30% in the rifaximin group compared with the placebo group (p=0.0793 for between-group difference in relative risk). In the first study, the risk of all-cause hospitalization rate was reduced by 30% in the rifaximin group when compared to placebo (p=0.0793 for between-group difference in relative risk). The all-cause hospitalization rate was 0.92 events/PEY in the rifaximin group versus 1.31 event/PEY in the placebo group.

In the second study, the low HE-caused hospitalization rate was maintained at rates consistent with those in the first study: HE-caused hospitalization rate was 0.29 event/PEY and all cause hospitalization in the second study was 0.66 event/PEY. The consistently low HE-related/HE-caused hospitalization rate in rifaximin-treated subjects in the first study and in the second study was at least partly a result of maintaining remission from demonstrated HE in subjects with end-stage liver disease. Improved Quality of Life in HE Subjects Administered Rifaximin HE is manifested as a continuum of mental status deterioration, psychomotor dysfunction, impaired memory, increased reaction time, sensory abnormalities, poor concentration, disorientation, and in severe forms, coma. Patients with HE experience symptoms that have adverse consequences for the patient's health-related quality of life, and result in a decreased ability for self care. The Chronic Liver Disease Questionnaire (CLDQ) is a validated instrument for measuring health-related quality of life in subjects with chronic liver disease. The mean change from baseline in CLDQ fatigue domain scores at end of treatment was 1 of 5 key secondary endpoints in this study. Additionally, mean change from baseline in CLDQ scores (overall score and each domain score) at each postbaseline assessment and at end of treatment was one of the tertiary efficacy endpoints prespecified in the study protocol.

The CLDQ was administered at Baseline, Days 28, 56, 84, 112, and 140, and at Day 168 or end of treatment. The CLDQ includes 29 items in the following 6 domains: abdominal symptoms (three items), fatigue (five items), systemic symptoms (five items), activity (three items), emotional function (eight items), and worry (five items). Scores in the fatigue subdomain were highly correlated with liver disease severity as determined by clinical assessments. Therefore, the fatigue subdomain was chosen as a key secondary endpoint for the study.

Subjects ranked their level of fatigue by using a 7-point scale from the worst response (1, high degree of fatigue) the best response (7, minimal fatigue). Other domains and the overall score were also ranked on a 7-point scale with higher scores indicating better quality of life and lower scores reflecting lower quality of life. For example, 1 of the 5 fatigue items was 'How much time have you been fatigued during the last 2 weeks?' Response options were 'all of the time,' 'most of the time,' 'a good bit of the time,' 'some of the time,' 'a little of the time,' 'hardly any of the time,' and 'none of the time.' These were graded as 1 (worst degree of fatigue), 2, 3, 4, 5, 6, and 7 (no fatigue), respectively.

In contrast to the change from baseline analysis, the AUC analysis presented below includes CLDQ results over the subject's complete time of participation in the study.

Area Under the Curve and Time-Weighted Average (Twa) Analysis of Chronic Liver Disease Questionnaire Results In the an original analysis of the study data, minimal differences between placebo and rifaximin groups were observed in the changes from baseline in CLDQ fatigue scores and in other CLDQ domain scores. Mean (SD) fatigue scores were 3.34 (1.406) versus 3.28 (1.326) at baseline and 3.51 (1.529) versus 3.57 (1.527) at last assessment in the placebo and rifaximin groups, respectively.

In this example, CLDQ responses were tracked over time for each subject and an area under the curve (AUC) was determined. For those subjects who had breakthrough HE episodes, CLDQ data reflect experience prior to the breakthrough episode. Because all subjects did not stay in the study for the same length of time, the AUC was normalized by exposure time (T), referred to as Time-weighted average (Twa) as given below:

$$Twa = \frac{AUC}{T},$$

Thus, Twa describes the average CLDQ response from baseline through the course of the trial, normalized to duration of exposure.

Figure 14A:
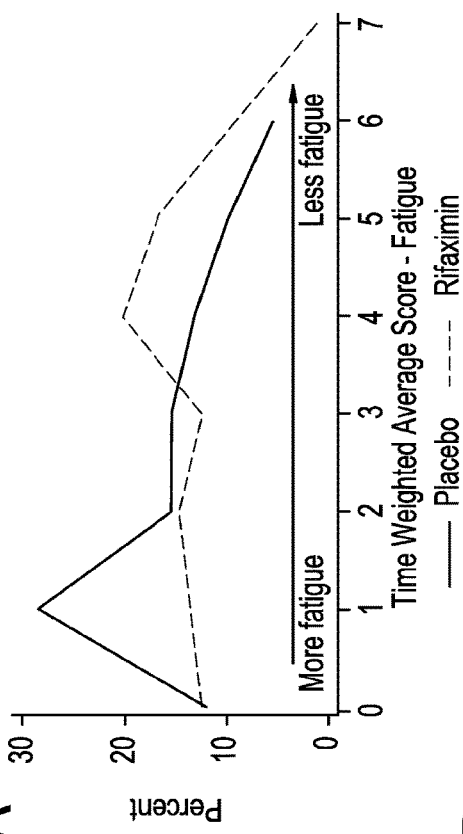
FIGS. 14A-B depict CLDQ results, as measured by Twa, between the rifaximin and placebo groups in the frequency distributions of Twa scores for the fatigue domain and overall domain.
Figure 14B:
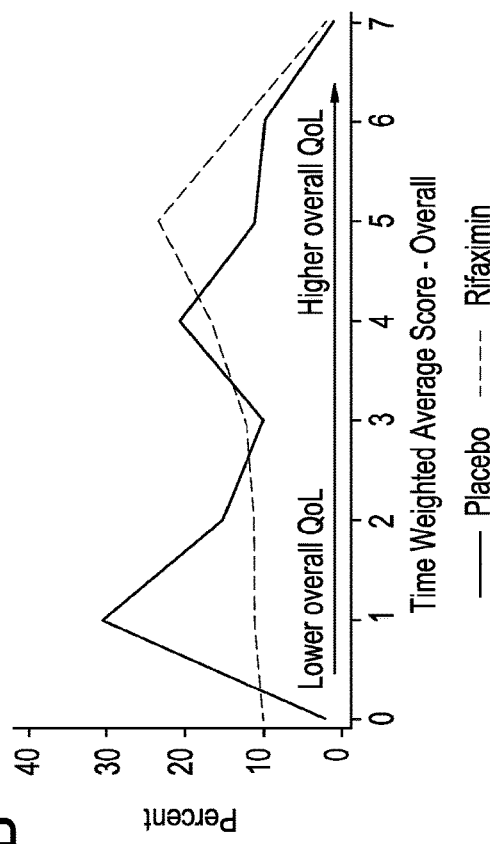

As shown below in FIG. 14A-B, there is a distinct separation in CLDQ results, as measured by Twa, between the rifaximin and placebo groups in the frequency distributions of Twa scores for the fatigue domain and overall domain. The shift in the frequency distribution toward higher scores in the rifaximin subjects indicates better responses; ie, improved overall quality of life results and less fatigue for the rifaximin group when compared with the placebo group. Similar between-group differences favoring the rifaximin group were observed in the frequency distributions for additional CLDQ domains.

Table 25 summarizes Twa results for the CLDQ overall domain scores and CLDQ fatigue domain scores by treatment group in the Intent-to-Treat (ITT) population. Time-weighted average scores for the fatigue domain and overall domain were significantly higher in the rifaximin group than in the placebo group (p=0.0087 [fatigue domain] and p=0.0093 [overall domain] for between-group differences in favor of the rifaximin group). Time-weighted average scores for other CLDQ domains were also significantly higher in the rifaximin group than in the placebo group (p=0.0090 [abdominal symptoms], p=0.0160 [systemic symptoms], p=0.0022 [activity], p=0.0065 [emotional function], and p=0.0436 [worry] for between-group differences in favor of the rifaximin group.

The differences in mean Twa scores between treatment groups (rifaximin minus placebo) were 0.72 for the fatigue domain and 0.75 for the overall domain. A difference of 0.5 points is considered important and a difference of 0.8 points is considered 'large' when using a 7-point scale for quality-of-life measurements.

Pertinent findings from the literature comparing subjects with no cirrhosis, Child-Pugh A, and Child-Pugh C liver disease suggest that differences of 0.5 to 1.0 in CLDQ scores are clinically significant. Mean differences in overall domain scores in subjects with no cirrhosis compared with subjects with Child-Pugh A (no cirrhosis minus Child-Pugh A) were 0.6 in subjects in the United States and 0.3 in a study of subjects in Spain. Greater mean differences in overall domain scores were reported for the transition from no cirrhosis to Child-Pugh C (no cirrhosis minus Child-Pugh C): 1.3 difference in the United States study and 1.0 difference in the Spain study.

TABLE 25

Area Under the Curve and Time-Weighted Average for CLDQ Results (ITT Population)

| CLDQ results parameter | Rifaximin N = 140 | Placebo N = 159 | P-value[a] |
|---|---|---|---|
| Fatigue domain | | | |
| Baseline score | n = 81 | n = 86 | |
| Mean (SD) | 3.37 (1.304) | 3.46 (1.363) | |
| Median (min, max) | 3.40 (1.0, 5.8) | 3.40 (1.4, 6.4) | |
| Twa (score) | n = 82 | n = 86 | |
| Mean (SD) | 3.242 (1.7619) | 2.522 (1.7538) | p = 0.0087 |
| Median (min, max) | 3.600 (0.29, 6.51) | 2.365 (0.27, 6.25) | |
| Overall domain | | | |
| Baseline score | n = 82 | n = 87 | |
| Mean (SD) | 4.18 (1.184) | 4.31 (1.058) | |
| Median (min, max) | 4.25 (1.6, 6.7) | 4.29 (1.7, 6.6) | |
| Twa (score) | n = 83 | n = 87 | |
| Mean (SD) | 3.692 (1.8607) | 2.943 (1.8480) | p = 0.0093 |
| Median (min, max) | 4.249 (0.39, 6.70) | 2.926 (0.46, 6.63) | |

When CLDQ results from the study were analyzed over the duration of exposure to study drug by calculation of Twa, subjects in the rifaximin group had significantly less fatigue and significantly greater overall quality of life than subjects in the placebo group. For example, mean (±SD) Twa fatigue scores were 3.24 (1.76) in the rifaximin group and 2.42 (1.75) in the placebo group (p=0.0087 in favor of the rifaximin group). Significant differences in Twa CLDQ results in favor of the rifaximin group were also observed for the overall CLDQ domain score (p=0.0093), and for each of the other component domains of the CLDQ, including abdominal symptoms (p=0.0090), systemic symptoms (p=0.0160), activity (p=0.0022), emotional function (p=0.0065), and worry (p=0.0436).

Importantly, these data demonstrate that rifaximin treatment resulted in significantly improved quality of life compared to placebo over a 6-month treatment period in subjects with hepatic cirrhosis and recurrent, overt HE, prior to experiencing a new onset overt HE and performed without data impugnation. This demonstrates that the patients in this study reported improvement in every domain relative to the placebo group. The observed statistically significant difference between the rifaximin and placebo groups agrees with the clinically significant differences reported for subjects with increasing severity of liver disease as measured by Child-Pugh score.

Correlation of CFF to Breakthrough Overt HE

As a test of the reliability and clinical relevance of the primary endpoint, the quantitative results for CFF were tested for correlation to the occurrence of breakthrough overt HE (primary efficacy measure), which was determined on the basis of clinical symptoms using Conn score (or a combination of Conn score and asterixis grade).

The CFF values were tracked over time for each subject and it was noted that on average, subjects who experienced a breakthrough HE had lower test values than subjects who did not experience a breakthrough event. And it was further noted that the area under the CFF versus time curve (AUC) could be used to accurately describe the variation in the CFF over time for each subject as a Time-weighted average (twa). Since all subjects did not stay in the study for the same length of time, the twa was normalized by exposure time (T).

The results of the CFF test over time were expressed as:

$$twa = \frac{AUC}{T},$$

where T is the exposure time. Thus, twa describes the average CFF effect through the trial.

The correlation between twa and the presence or absence of breakthrough HE episode was analyzed with analysis of variance and Spearman rank correlation coefficient. Additionally, a ROC curve analysis was performed to evaluate the accuracy of the twa to discriminate between the presence or absence of breakthrough episodes. In a ROC curve, the true positive rate (Sensitivity) is plotted against the false positive rate (1-Specificity). A diagnostic test with perfect discrimination has a ROC plot that passes through the upper left corner (100% sensitivity, 100% specificity). Therefore the closer the ROC plot to the upper left corner, the higher the overall accuracy of the test.

Figure 31:
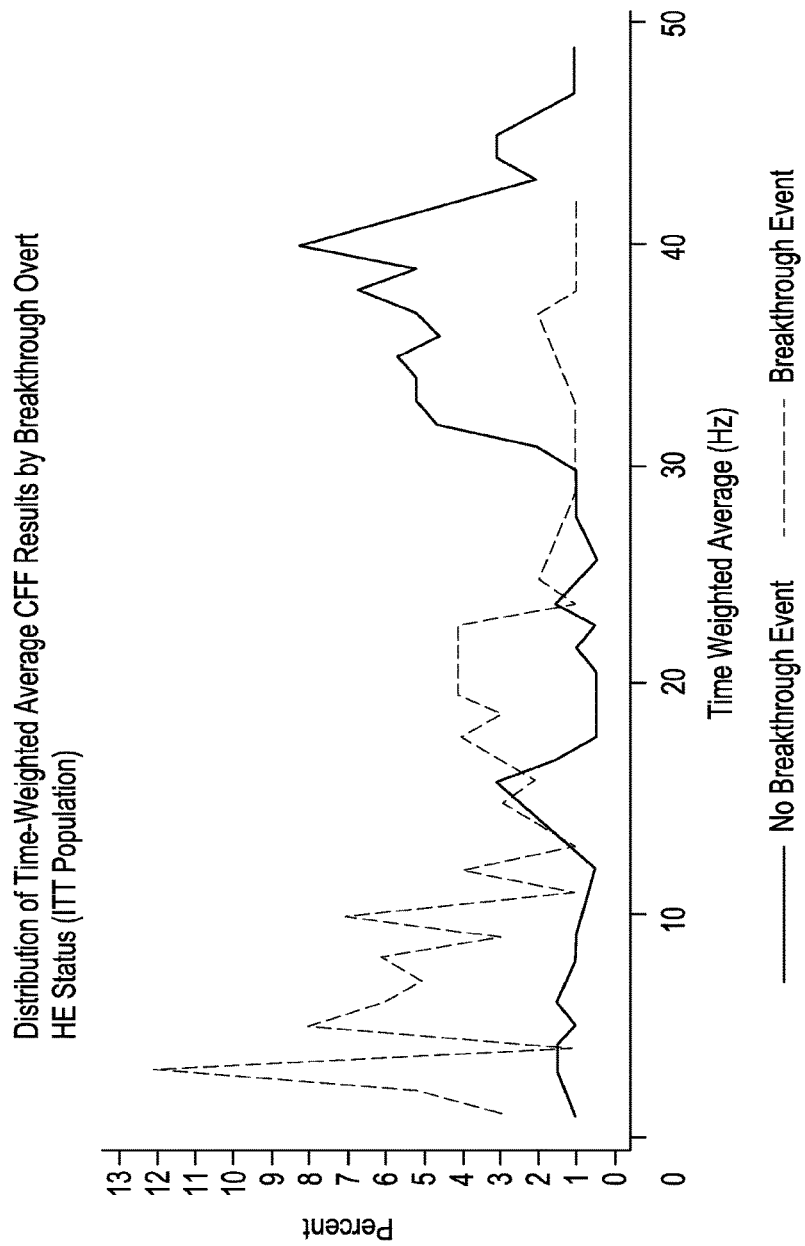
FIG. 31 depicts the distribution of time-weighted average CFF results by breakthrough overt HE status.

FIGS. 31 and 32 and Table 26 demonstrate that the difference between the frequency distributions of twa corresponding to the presence (mean=12.5 Hz) and absence of breakthrough HE events (mean=32.7 Hz) was statistically significant (p<0.0001). Also, mean twa correlated with presence or absence of breakthrough HE episode (Spearman correlation coefficient=−0.62; p<0.0001).

TABLE 26

Area Under the Curve and Time-Weighted Average for CFF Results (ITT Population)

| CFF results parameter | Non-breakthrough HE N = 195 | Breakthrough HE N = 104 | P-Value[a] |
|---|---|---|---|
| $AUC_{(1\text{-}168\ days)}$ (Hz × day) | n = 194 | n = 99 | |
| Mean (SD) | 5455.07 (1918.260) | 2090.24 (1648.022) | |
| Median (min, max) | 6037.0 (137.4, 8189.4) | 1610.2 (175.7, 7092.9) | |
| twa (HZ)[b] | n = 194 | n = 99 | |
| Mean (SD) | 32.67 (11.487) | 12.52 (9.868) | p < 0.0001 |
| Median (min, max) | 36.2 (0.8, 49.0) | 9.6 (1.1, 42.5) | |

CFF: critical flicker frequency;
AUC: area under the ammonia concentration versus time curve;
twa: time-weighted average
[a]p-value calculated using ANCOVA model with effects for treatment and analysis region as covariates.
[b]Spearman's correlation for twa to presence or absence of breakthrough HE equals −0.62;
p < 0.0001

The ROC curve analysis of twa for the diagnosis of breakthrough HE by CFF showed an area under the curve value of 0.88 (95% CI 0.84-0.92). Values close to 1, and the appearance of the ROC plot closer to the upper left corner, are considered diagnostically significant.

Thus, CFF, which is an accepted, physiologically relevant, quantitative measure associated with HE, was shown to be highly predictive of breakthrough HE as defined by as an increase of Conn score to Grade ≥2 (ie, 0 or 1 to ≥2) or an increase in Conn and asterixis score of 1 grade each for those subjects who entered the study with a Conn score of 0. The fact that this quantitative measure discriminates in a highly statistically significant manner demonstrates the reliability and clinical relevance of the primary efficacy measure.

Example 6: Correlation of the Venous Ammonia Levels to HE Breakthrough Events

Subjects administered rifaximin had significantly greater reductions in venous ammonia levels when compared to placebo-treated subjects (p=0.0391, see Table 27). Venous ammonia levels were assessed at Screening, Baseline, Day 28, Day 84, and Day 168/end-of-treatment.

TABLE 27

Mean (SD) Changes from Baseline in Venous Ammonia Level by Treatment Group (ITT Population)

| | Placebo N = 159 (µg/dL) | Rifaximin N = 140 (µg/dL) | P-Value[a] |
|---|---|---|---|
| Baseline | n = 146 | n = 132 | |
| Mean (SD) ammonia level | 90.3 (52.48) | 87.9 (47.76) | |
| End of treatment | n = 141 | n = 132 | |
| Mean (SD) ammonia level | 88.4 (45.75) | 83.9 (45.02) | |
| Change from baseline to end of treatment | n = 131 | n = 125 | |
| Mean (SD) change in ammonia level | −0.3 (58.13) | −5.7 (46.77) | p = 0.0391 |

Note:
Baseline value was the last available value prior to first dose of study drug, and end of treatment value was the last available postbaseline value during the treatment period.
[a]P-value was calculated using analysis of covariance with effects for treatment and analysis region, and baseline as a covariate.

Blood ammonia levels, a quantitative assessment that is associated with the CNS effects underlying overt HE, was found to be highly correlated to the occurrence of breakthrough overt HE as determined by clinical evaluation. This high degree of correlation was consistent with the correlation between CFF results and the occurrence of breakthrough overt HE.

The venous ammonia laboratory values were tracked over time for each subject. To normalize by exposure time, a twa value was calculated similarly to the CFF analysis.

The correlation between the ammonia twa and the presence or absence of breakthrough HE episode was analyzed as described for the CFF.

FIG. 33 and Table 28 show that the difference between the frequency distributions of twa corresponding to the presence (mean=102.4 µmol/L) and absence of breakthrough HE events (mean=85.4 µmol/L) was statistically significant (p=0.0079). Also, mean twa correlated with presence or absence of breakthrough HE episode (Spearman correlation coefficient of 0.22, p=0.0005).

TABLE 28

Area Under the Curve and Time-Weighted Average for Venous Ammonia Concentrations (ITT Population)

| Venous ammonia concentration parameter | Non-breakthrough HE N = 195 | Breakthrough HE N = 104 | P-Value[a] |
|---|---|---|---|
| $AUC_{(1-28\ days)}$ (µmol/L × day) | n = 173 | n = 68 | |
| Mean (SD) | 2304.83 (1211.428) | 2763.93 (1160.357) | |
| Median (min, max) | 2038.5 (499.5, 9153.0) | 2787.8 (999.0, 7681.5) | |
| twa (µmol/L)[b] | n = 173 | n = 68 | p = 0.0079 |
| Mean (SD) | 85.36 (44.87) | 102.37 (42.98) | |
| Median (min, max) | 75.5 (18.5, 339.0) | 103.25 (37.0, 284.5) | |

AUC: area under the ammonia concentration versus time curve;
twa: time-weighted average.
[a]p-value calculated using ANCOVA model with effects for treatment and analysis region as covariates.
[b]Spearman's correlation for twa to presence or absence of breakthrough HE equals 0.22; p = 0.0005

The ROC curve analysis of twa for the diagnosis of breakthrough HE by venous ammonia levels, showed an area under the curve value of 0.64 (95% CI 0.57-0.72) (See FIG. 34). Values close to 1, and the appearance of the ROC plot closer to the upper left corner, are considered diagnostically significant.

Thus, venous ammonia level, which is an accepted physiologically relevant quantitative measure associated with HE, was shown to be highly predictive of breakthrough HE as defined by as an increase of Conn score to Grade ≥2 (ie, 0 or 1 to ≥2) or an increase in Conn and asterixis score of 1 grade each for those subjects who entered the study with a Conn score of 0. The fact that this quantitative measure discriminates in a highly statistically significant manner the presence or absence of breakthrough HE attests to the reliability and clinical relevance of the primary efficacy measure.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of reducing the risk of hospitalization for a subject having hepatic encephalopathy (HE) comprising orally administering between about 1000 mg to about 1200 mg rifaximin daily to the subject for a period of 12 months or longer, thereby reducing the risk of hospitalization.

2. The method of claim 1, wherein the amount of rifaximin is sufficient to reduce the frequency of hospitalization visits by at least 50 percent compared to a subject who is not being administered rifaximin.

3. The method of claim 1, wherein the HE is overt hepatic encephalopathy.

4. The method of claim 1, wherein the subject has a history of recurrent, episodic, and overt hepatic encephalopathy (HE).

5. The method of claim 1, further comprising administering lactulose to the subject.

6. The method of claim 1 comprising orally administering about 1100 mg of rifaximin per day to the subject.

7. The method of claim 6 comprising orally administering about 550 mg of rifaximin twice daily to the subject.

8. The method of claim 1, wherein the subject is at least 18 years old.

9. The method of claim 1, wherein the rifaximin is administered to the subject with or without food.

10. The method of claim 1 comprising administering the rifaximin to the subject for a duration between 12 to 24 months.

11. The method of claim 1 comprising administering the rifaximin to the adult subject for the duration of the subject's life.

12. The method of claim 1, wherein the subject has had two or fewer HE episodes in the 6-month period prior to commencing administration of rifaximin.

13. The method of claim 1, wherein the subject has had two or more HE episodes in the 6-month period prior to commencing administration of rifaximin.

* * * * *